(12) United States Patent
Galley et al.

(10) Patent No.: US 9,029,370 B2
(45) Date of Patent: May 12, 2015

(54) SUBSTITUTED BENZAMIDE DERIVATIVES

(75) Inventors: Guido Galley, Rheinfelden (DE); Roger Norcross, Olsberg (CH); Philippe Pflieger, Schwoben (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/485,993

(22) Filed: Jun. 1, 2012

(65) Prior Publication Data

US 2012/0316165 A1     Dec. 13, 2012

(30) Foreign Application Priority Data

Jun. 10, 2011 (EP) .................................. 11169441

(51) Int. Cl.
*C07D 401/12* (2006.01)
*C07D 413/14* (2006.01)
*C07D 265/30* (2006.01)
*C07D 413/12* (2006.01)

(52) U.S. Cl.
CPC ............ *C07D 413/14* (2013.01); *C07D 265/30* (2013.01); *C07D 401/12* (2013.01); *C07D 413/12* (2013.01)

(58) Field of Classification Search
CPC .................................................... C07D 401/12
USPC ........................................ 544/111; 514/231.5
See application file for complete search history.

(56) References Cited

U.S. PATENT DOCUMENTS

| 2009/0036420 A1 | 2/2009 | Galley et al. |
| 2011/0152245 A1 | 6/2011 | Groebke Zbinden |

FOREIGN PATENT DOCUMENTS

| WO | 97/12874 | 4/1997 |
| WO | 99/28300 | 6/1999 |
| WO | 02/076950 | 10/2002 |
| WO | 2008026046 | 6/2008 |
| WO | 2008/086047 | 7/2008 |
| WO | 2008/092930 | 8/2008 |
| WO | 2011/023795 | 3/2011 |
| WO | 2011/029046 | 3/2011 |
| WO | 2011057973 | 5/2011 |
| WO | 2011/076678 | 6/2011 |
| WO | 2012/016879 | 2/2012 |
| WO | 2012/168260 | 12/2012 |

OTHER PUBLICATIONS

The Taiwanese Office Action, issued on Dec. 6, 2013, in the corresponding Taiwanese Application No. 101120551.
(International Search Report in Corres PCT/EP2012/060637 Jul. 17, 2012).
Branchek et al., "Curr Opin Pharmacol" 3:90-97 ( 2003).
Lindemann et al., "Trends in Pharmacol. Sci." 26:274-281 ( 2005).
Usdin et al., "Psychopharmacology Series" (Trace Amines and the Brain), 1:1-281 ( 1976).
Premont et al., "Proc. Natl. Acad. Sci. USA" 98:9474-9475 ( 2001).
Tuite et al., "Expert Opin. Investig. Drugs" 12:1335-1352 ( 2003).
McCormack et al., "J. Neurosci." 6:94-101 ( 1986).
Mosseau et al., "Prog. Brain res." 106:285-291 ( 1995).
Castellanos et al., "Nat. Rev. Neurosci." 3:617-628 ( 2002).
Parker et al., "J. Pharmacol. Exp. Ther." 245:199-210 ( 1988).
Dyck, L. E., "Life Sci." 44:1149-1156 ( 1989).
Deutch et al. Neurotransmitters in Fundamental Neuroscience 2nd edition,Academic Press,:193-234 ( 1999).
Carlsson et al., "Annu. Rev. Pharmacol. Toxicol." 41:237-260 ( 2001).
Lindemann et al., "Genomics" 85:372-385 ( 2005).
Wong et al., "Nat. Rev. Neurosci." 2:343-351 ( 2001).
The letter of opposition in the corresponding Costa Rican Application No. 2013-0557, which was notified by the Costa Rican Patent Office on Mar. 12, 2014.
The English translation of the Japanese Office Action, issued on Jan. 20, 2015, in the related Japanese application No. 2014-514044.

*Primary Examiner* — Shawquia Jackson

(57) ABSTRACT

The present invention relates to compounds of formula

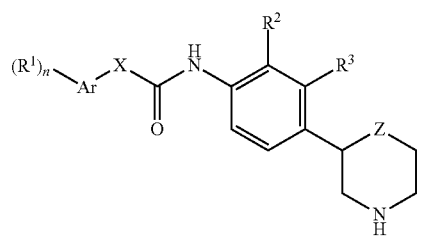

wherein $R^1$, $R^2$, $R^3$, X, Z, Ar, and n are as described in the claims,
Ar is phenyl or heteroaryl, selected from the group consisting of 1H-indazole-3yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or to a pharmaceutically suitable acid addition salt thereof, which may be used for the treatment of depression, anxiety disorders, bipolar disorder, attention deficit hyperactivity disorder (ADHD), stress-related disorders, psychotic disorders, schizophrenia, neurological diseases, Parkinson's disease, neurodegenerative disorders, Alzheimer's disease, epilepsy, migraine, hypertension, substance abuse, metabolic disorders, eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

13 Claims, No Drawings

SUBSTITUTED BENZAMIDE DERIVATIVES

PRIORITY TO RELATED APPLICATION(S)

This application claims the benefit of European Patent Application No. 11169441.0, filed Jun. 10, 2011, which is hereby incorporated by reference in its entirety.

BACKGROUND OF THE INVENTION

Some of the physiological effects (i.e. cardiovascular effects, hypotension, induction of sedation) which have been reported for compounds which may bind to adrenergic receptors (WO02/076950, WO97/12874 or EP 0717 037) may be considered to be undesirable side effects in the case of medicaments aimed at treating diseases of the central nervous system as described above. Therefore it is desirable to obtain medicaments having selectivity for the TAAR1 receptor vs adrenergic receptors. Compounds of the present invention show selectivity for TAAR1 receptor over adrenergic receptors, in particular good selectivity vs the human and rat alpha1 and alpha2 adrenergic receptors.

The classical biogenic amines (serotonin, norepinephrine, epinephrine, dopamine, histamine) play important roles as neurotransmitters in the central and peripheral nervous system [1]. Their synthesis and storage, as well as their degradation and reuptake after release are tightly regulated. An imbalance in the levels of biogenic amines is known to be responsible for the altered brain function under many pathological conditions [2-5]. A second class of endogenous amine compounds, the so-called trace amines (TAs) significantly overlaps with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines [6].

Their dysregulation has been linked to various psychiatric diseases like schizophrenia and depression [7] and for other conditions like attention deficit hyperactivity disorder, migraine headache, Parkinson's disease, substance abuse and eating disorders [8,9].

For a long time, TA-specific receptors had only been hypothesized based on anatomically discrete high-affinity TA binding sites in the CNS of humans and other mammals [10,11]. Accordingly, the pharmacological effects of TAs were believed to be mediated through the well known machinery of classical biogenic amines, by either triggering their release, inhibiting their reuptake or by "crossreacting" with their receptor systems [9,12,13]. This view changed significantly with the recent identification of several members of a novel family of GPCRs, the trace amine associated receptors (TAARs) [7,14]. There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies [7,14]. TAAR1 is in the first subclass of four genes (TAAR1-4) highly conserved between human and rodents. TAs activate TAAR1 via Gαs. Dysregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

Therefore, there is a broad interest to increase the knowledge about trace amine associated receptors.

REFERENCES USED

1 Deutch, A. Y. and Roth, R. H. (1999) Neurotransmitters. In *Fundamental Neuroscience* ($2^{nd}$ edn) (Zigmond, M. J., Bloom, F. E., Landis, S. C., Roberts, J. L, and Squire, L. R., eds.), pp. 193-234, Academic Press;

2 Wong, M. L. and Licinio, J. (2001) Research and treatment approaches to depression. *Nat. Rev. Neurosci.* 2, 343-351;

3 Carlsson, A. et al. (2001) Interactions between monoamines, glutamate, and GABA in schizophrenia: new evidence. *Annu. Rev. Pharmacol. Toxicol.* 41, 237-260;

4 Tuite, P. and Riss, J. (2003) Recent developments in the pharmacological treatment of Parkinson's disease. *Expert Opin. Investig. Drugs* 12, 1335-1352, 5 Castellanos, F. X. and Tannock, R. (2002) Neuroscience of attention-deficit/hyperactivity disorder: the search for endophenotypes. *Nat. Rev. Neurosci.* 3, 617-628;

6 Usdin, Earl; Sandler, Merton; Editors. *Psychopharmacology Series, Vol. 1: Trace Amines and the Brain. [Proceedings of a Study Group at the 14th Annual Meeting of the American College of Neuropsychopannacology*, San Juan, Puerto Rico] (1976);

7 Lindemann, L. and Hoener, M. (2005) A renaissance in trace amines inspired by a novel GPCR family. *Trends in Pharmacol. Sci.* 26, 274-281;

8 Branchek, T. A. and Blackburn, T. P. (2003) Trace amine receptors as targets for novel therapeutics: legend, myth and fact. *Curr. Opin. Pharmacol.* 3, 90-97;

9 Premont, R. T. et al. (2001) Following the trace of elusive amines. *Proc. Natl. Acad. Sci. U.S.A.* 98, 9474-9475;

10 Mousseau, D. D. and Butterworth, R. F. (1995) A high-affinity [3H] tryptamine binding site in human brain. *Prog. Brain Res.* 106, 285-291;

11 McCormack, J. K. et al. (1986) Autoradiographic localization of tryptamine binding sites in the rat and dog central nervous system. *J. Neurosci.* 6, 94-101;

12 Dyck, L. E. (1989) Release of some endogenous trace amines from rat striatal slices in the presence and absence of a monoamine oxidase inhibitor. *Life Sci.* 44, 1149-1156;

13 Parker, E. M. and Cubeddu, L. X. (1988) Comparative effects of amphetamine, phenylethylamine and related drugs on dopamine efflux, dopamine uptake and mazindol binding. *J. Pharmacol. Exp. Ther.* 245, 199-210;

14 Lindemann, L. et al. (2005) Trace amine associated receptors form structurally and functionally distinct subfamilies of novel G protein-coupled receptors. *Genomics* 85, 372-385.

SUMMARY OF THE INVENTION

The present invention provides new compounds of formula I and their pharmaceutically acceptable salts and pharmaceutical compositions containing them. The invention further provides methods for the manufacture of the compounds and compositions of the invention. The invention provides for the treatment of diseases related to the biological function of the trace amine associated receptors, e.g. for the control or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The present invention provides compounds of formula

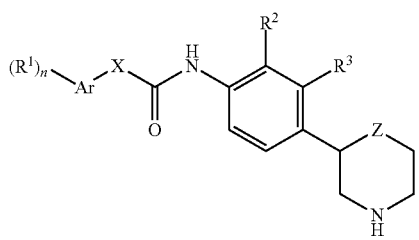

I wherein
R$^1$ is hydrogen,
  halogen,
  cyano,
  lower alkyl,
  lower alkyl substituted by halogen,
  lower alkoxy,
  lower alkoxy substituted by halogen or C(O)NH$_2$,
  phenyl optionally substituted by halogen, cyano or lower alkoxy substituted by halogen,
  2,2-difluorobenzo[d][1,3]dioxol-5-yl,
  6-(trifluoromethyl)pyrazin-2-yl,
  5-(trifluoromethyl)pyrazin-2-yl,
  6-(trifluoromethyl)pyrimidin-4-yl,
  6-(trifluoromethyl)pyridin-3-yl,
  5-cyanopyrazin-2-yl or
  2-(trifluoromethyl)pyrimidin-4-yl;
  n is 1 or 2;
R$^2$ is halogen, lower alkyl or cyano and R$^3$ is hydrogen, or
R$^2$ is hydrogen and R$^3$ is halogen, lower alkyl or cyano;
X is a bond, —NR'—, —CH$_2$NH— or —CHR'—;
R' is hydrogen or lower alkyl;
Z is a bond, —CH$_2$— or —O—;
Ar is phenyl or heteroaryl selected from the group consisting of 1H-indazole-3yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or to a pharmaceutically suitable acid addition salt thereof.

The invention includes all racemic mixtures, all their corresponding enantiomers and/or optical isomers. In addition, all tautomeric forms of compounds of formula I are also encompassed by the present invention.

Compounds of formulas I have a good affinity to the trace amine associated receptors (TAARs), especially for TAAR1.

The compounds can be used for the treatment of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders.

The preferred indications using the compounds of the present invention are depression, psychosis, Parkinson's disease, anxiety, attention deficit hyperactivity disorder (ADHD) and diabetes.

DETAILED DESCRIPTION OF THE INVENTION

As used herein, the term "lower alkyl" denotes a saturated straight- or branched-chain group containing from 1 to 7 carbon atoms, for example, methyl, ethyl, propyl, isopropyl, n-butyl, i-butyl, 2-butyl, t-butyl and the like. Preferred alkyl groups are groups with 1-4 carbon atoms.

As used herein, the term "lower alkoxy" denotes a group wherein the alkyl residue is as defined above, which is attached via an oxygen atom.

The term "halogen" denotes chlorine, iodine, fluorine and bromine.

As used herein, the term "lower alkyl substituted by halogen" denotes a saturated straight- or branched-chain group containing from 1 to 7 carbon atoms as defined for the term "lower alkyl", wherein at least one hydrogen atom is replaced by a halogen atom. A preferred halogen atom is fluoro. Examples of such groups are CF$_3$, CHF$_2$, CH$_2$F, CH$_2$CF$_3$ and CH$_2$CHF$_2$.

As used herein, the term "lower alkoxy substituted by halogen" denotes an alkoxy group as defined above and wherein on or more hydrogen atoms are replaced by halogen, for example OCH$_3$, OCHF$_2$, OCH$_2$F, OCH$_2$CF$_3$ and OCH$_2$CHF$_2$.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluene-sulfonic acid and the like.

The terms "pharmaceutically acceptable carrier" and "pharmaceutically acceptable auxiliary substance" refer to carriers and auxiliary substances such as diluents or excipients that are compatible with the other ingredients of the formulation.

"Therapeutically effective amount" means an amount of a compound that, when administered to a subject for treating a disease state, is sufficient to effect such treatment for the disease state. The "therapeutically effective amount" will vary depending on the compound, disease state being treated, the severity or the disease treated, the age and relative health of the subject, the route and form of administration, the judgment of the attending medical or veterinary practitioner, and other factors.

One embodiment of the invention is compounds of formula IA

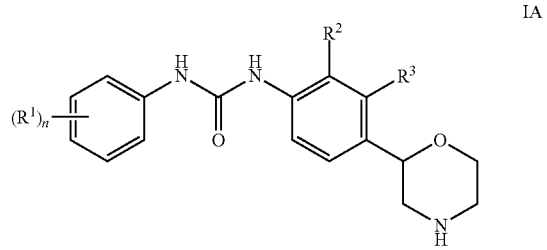

IA

R$^1$ is hydrogen,
  halogen,
  cyano, lower alkyl,
lower alkyl substituted by halogen,
lower alkoxy,
lower alkoxy substituted by halogen or C(O)NH$_2$,
phenyl optionally substituted by halogen, cyano or lower alkoxy substituted by halogen,
2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl,
5-cyanopyrazin-2-yl,
or 2-(trifluoromethyl)pyrimidin-4-yl;
n is 1 or 2;
R$^2$ is halogen, lower alkyl or cyano and R$^3$ is hydrogen, or
R$^2$ is hydrogen and R$^3$ is halogen, lower alkyl or cyano;
or a pharmaceutically suitable acid addition salt thereof, for example the following compounds:
1-(3-cyano-phenyl)-3-((R)-2-fluoro-4-morpholin-2-yl-phenyl)-urea;
1-(3-cyano-phenyl)-3-((S)-2-fluoro-4-morpholin-2-yl-phenyl)-urea;
(RS)-1-(2-chloro-4-(morpholin-2-yl)phenyl)-3-(3-cyanophenyl)urea;
(S)-1-(2-chloro-4-(morpholin-2-yl)phenyl)-3-(3-cyanophenyl)urea;
(R)-1-(2-chloro-4-(morpholin-2-yl)phenyl)-3-(3-cyanophenyl)urea;
1-(3-cyano-5-fluoro-phenyl)-3-((S)-2-fluoro-4-morpholin-2-yl-phenyl)-urea;
1-(3-cyano-4-fluoro-phenyl)-3-((S)-2-fluoro-4-morpholin-2-yl-phenyl)-urea;
(S)-1-(5-cyano-2-methoxyphenyl)-3-(2-fluoro-4-(morpholin-2-yl)phenyl)urea;
(R)-1-(5-cyano-2-methoxyphenyl)-3-(2-fluoro-4-(morpholin-2-yl)phenyl)urea;
(R)-1-(2-chloro-4-(morpholin-2-yl)phenyl)-3-(5-cyano-2-methoxyphenyl)urea;
(S)-1-(2-chloro-4-(morpholin-2-yl)phenyl)-3-(5-cyano-2-methoxyphenyl)urea;
(R)-1-(2-chloro-4-(morpholin-2-yl)phenyl)-3-(5-cyano-2-(difluoromethoxy)phenyl)urea;
(S)-1-(2-chloro-4-(morpholin-2-yl)phenyl)-3-(5-cyano-2-(difluoromethoxy)phenyl)urea;
1-(5-cyano-2-fluoro-phenyl)-3-((R)-2-fluoro-4-morpholin-2-yl-phenyl)-urea;
1-((R)-2-bromo-4-morpholin-2-yl-phenyl)-3-(5-cyano-2-methoxy-phenyl)-urea;
1-((S)-2-bromo-4-morpholin-2-yl-phenyl)-3-(5-cyano-2-methoxy-phenyl)-urea;
1-(3-cyano-5-fluoro-phenyl)-3-((R)-2-fluoro-4-morpholin-2-yl-phenyl)-urea;
1-((R)-2-bromo-4-morpholin-2-yl-phenyl)-3-(5-cyano-2-difluoromethoxy-phenyl)-urea;
1-((S)-2-bromo-4-morpholin-2-yl-phenyl)-3-(5-cyano-2-difluoromethoxy-phenyl)-urea;
(R)-1-(3-cyano-2-fluorophenyl)-3-(2-fluoro-4-(morpholin-2-yl)phenyl)urea;
(R)-1-(3-cyano-4-fluorophenyl)-3-(2-fluoro-4-(morpholin-2-yl)phenyl)urea;
1-(5-cyano-2-difluoromethoxy-phenyl)-3-((S)-2-fluoro-4-morpholin-2-yl-phenyl)-urea;
1-(5-cyano-2-difluoromethoxy-phenyl)-3-((R)-2-fluoro-4-morpholin-2-yl-phenyl)-urea;
(S)-1-(5-cyano-2-ethoxyphenyl)-3-(2-fluoro-4-(morpholin-2-yl)phenyl)urea; and
(R)-1-(5-cyano-2-ethoxyphenyl)-3-(2-fluoro-4-(morpholin-2-yl)phenyl)urea.

One further embodiment of the invention is compounds of formula IB

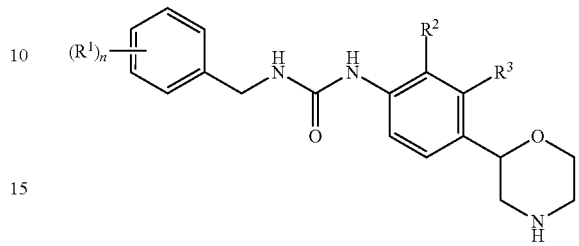

wherein
R$^1$ is hydrogen,
halogen,
cyano,
lower alkyl,
lower alkyl substituted by halogen,
lower alkoxy,
lower alkoxy substituted by halogen or C(O)NH$_2$,
phenyl optionally substituted by halogen, cyano or lower alkoxy substituted by halogen,
2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl,
5-cyanopyrazin-2-yl, or
2-(trifluoromethyl)pyrimidin-4-yl;
n is 1 or 2;
R$^2$ is halogen, lower alkyl or cyano and R$^3$ is hydrogen, or
R$^2$ is hydrogen and R$^3$ is halogen, lower alkyl or cyano;
or a pharmaceutically suitable acid addition salt thereof, for example the following compounds:
1-(3-cyano-benzyl)-3-((R)-2-fluoro-4-morpholin-2-yl-phenyl)-urea;
1-(3-cyano-benzyl)-3-((S)-2-fluoro-4-morpholin-2-yl-phenyl)-urea;
(R)-1-(3-(difluoromethoxy)benzyl)-3-(2-fluoro-4-(morpholin-2-yl)phenyl)urea; and
(S)-1-(3-(difluoromethoxy)benzyl)-3-(2-fluoro-4-(morpholin-2-yl)phenyl)urea.

One further embodiment of the invention is compounds of formula IC

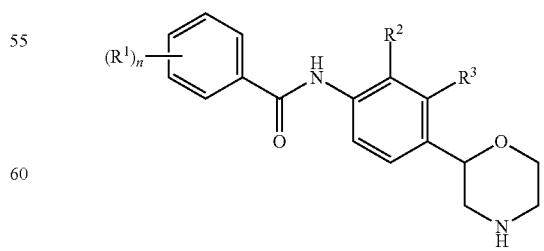

wherein
R$^1$ is hydrogen,
halogen, cyano,
lower alkyl,
lower alkyl substituted by halogen,
lower alkoxy,
lower alkoxy substituted by halogen or C(O)NH$_2$,
phenyl optionally substituted by halogen, cyano or lower alkoxy substituted by halogen,
2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl, 5-cyanopyrazin-2-yl, or
2-(trifluoromethyl)pyrimidin-4-yl;
n is 1 or 2;
R$^2$ is halogen, lower alkyl or cyano and R$^3$ is hydrogen, or
R$^2$ is hydrogen and R$^3$ is halogen, lower alkyl or cyano;
or a pharmaceutically suitable acid addition salt thereof for example the following compound:
(S)-4-chloro-N-(2-chloro-4-(morpholin-2-yl)phenyl)benzamide.

One further embodiment of the invention is compounds of formula ID

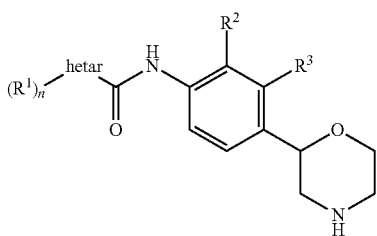

ID wherein
R$^1$ is hydrogen,
halogen,
cyano,
lower alkyl,
lower alkyl substituted by halogen,
lower alkoxy,
lower alkoxy substituted by halogen or C(O)NH$_2$,
phenyl optionally substituted by halogen, cyano or lower alkoxy substituted by halogen,
2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl,
5-cyanopyrazin-2-yl,
or 2-(trifluoromethyl)pyrimidin-4-yl;
n is 1 or 2;
R$^2$ is halogen, lower alkyl or cyano and R$^3$ is hydrogen, or
R$^2$ is hydrogen and R$^3$ is halogen, lower alkyl or cyano;
Hetar is selected from the group consisting of 1H-indazole-3yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or a pharmaceutically suitable acid addition salt thereof, for example the following compounds
6-fluoro-1H-indazole-3-carboxylic acid ((R)-2-fluoro-4-morpholin-2-yl-phenyl)-amide;
6-fluoro-1H-indazole-3-carboxylic acid ((S)-2-fluoro-4-morpholin-2-yl-phenyl)-amide;
1-(4-fluoro-phenyl)-1H-pyrazole-3-carboxylic acid ((R)-2-fluoro-4-morpholin-2-yl-phenyl)-amide;
1-(4-fluoro-phenyl)-1H-pyrazole-3-carboxylic acid ((S)-2-fluoro-4-morpholin-2-yl-phenyl)-amide;
2-methyl-5-phenyl-2H-pyrazole-3-carboxylic acid ((S)-2-fluoro-4-morpholin-2-yl-phenyl)-amide;
(RS)—N-(2-chloro-4-(morpholin-2-yl)phenyl)-1-(4-fluorophenyl)-1H-pyrazole-4-carboxamide;
(R)—N-(2-fluoro-4-(morpholin-2-yl)phenyl)-1-(4-fluorophenyl)-1H-pyrazole-4-carboxamide;
(S)—N-(2-fluoro-4-(morpholin-2-yl)phenyl)-1-(4-fluorophenyl)-1H-pyrazole-4-carboxamide;
2-methyl-5-phenyl-2H-pyrazole-3-carboxylic acid ((R)-2-fluoro-4-morpholin-2-yl-phenyl)-amide;
2-chloro-N—((R)-2-fluoro-4-morpholin-2-yl-phenyl)-6-methoxy-isonicotinamide;
2-chloro-N—((S)-2-fluoro-4-morpholin-2-yl-phenyl)-6-methoxy-isonicotinamide;
(RS)—N-(2-cyano-4-(morpholin-2-yl)phenyl)-1-(4-fluorophenyl)-1H-pyrazole-3-carboxamide;
(S)—N-(2-chloro-4-(morpholin-2-yl)phenyl)-1-(4-fluorophenyl)-1H-pyrazole-3-carboxamide;
(R)—N-(2-chloro-4-(morpholin-2-yl)phenyl)-1-(4-fluorophenyl)-1H-pyrazole-3-carboxamide;
(S)—N-(2-chloro-4-(morpholin-2-yl)phenyl)-1-(4-fluorophenyl)-1H-pyrazole-4-carboxamide;
(R)—N-(2-chloro-4-(morpholin-2-yl)phenyl)-1-(4-fluorophenyl)-1H-pyrazole-4-carboxamide;
(R)-6-chloro-N-(2-chloro-4-(morpholin-2-yl)phenyl)nicotinamide;
(S)-6-chloro-N-(2-chloro-4-(morpholin-2-yl)phenyl)nicotinamide;
6-chloro-N—((R)-2-methyl-4-morpholin-2-yl-phenyl)-nicotinamide;
(S)-1-(3-(difluoromethoxy)phenyl)-N-(2-fluoro-4-(morpholin-2-yl)phenyl)-1H-pyrazole-4-carboxamide;
(S)-1-(4-(difluoromethoxy)phenyl)-N-(2-fluoro-4-(morpholin-2-yl)phenyl)-1H-pyrazole-4-carboxamide;
(S)-4-cyano-N-(2-fluoro-4-(morpholin-2-yl)phenyl)picolinamide;
(R)-4-cyano-N-(2-fluoro-4-(morpholin-2-yl)phenyl)picolinamide;
(S)-6-cyano-N-(2-fluoro-4-(morpholin-2-yl)phenyl)picolinamide;
(S)-1-(2,2-difluorobenzo[d][1,3]dioxol-5-yl)-N-(2-fluoro-4-(morpholin-2-yl)phenyl)-1H-pyrazole-4-carboxamide;
(R)—N-(3-fluoro-4-(morpholin-2-yl)phenyl)-2-(trifluoromethyl)isonicotinamide;
(R)-2-ethoxy-N-(3-fluoro-4-(morpholin-2-yl)phenyl)isonicotinamide;
(R)-6-ethoxy-N-(3-fluoro-4-(morpholin-2-yl)phenyl)nicotinamide;
(R)-1-(4-(difluoromethoxy)phenyl)-N-(3-fluoro-4-(morpholin-2-yl)phenyl)-1H-pyrazole-4-carboxamide;
(S)—N-(3-fluoro-4-(morpholin-2-yl)phenyl)-2-(trifluoromethyl)isonicotinamide;
(S)-2-ethoxy-N-(3-fluoro-4-(morpholin-2-yl)phenyl)isonicotinamide;
(S)-6-ethoxy-N-(3-fluoro-4-(morpholin-2-yl)phenyl)nicotinamide;
(S)-1-(4-(difluoromethoxy)phenyl)-N-(3-fluoro-4-(morpholin-2-yl)phenyl)-1H-pyrazole-4-carboxamide;
(R)—N-(3-chloro-4-(morpholin-2-yl)phenyl)-2-ethoxyisonicotinamide;
(R)—N-(3-chloro-4-(morpholin-2-yl)phenyl)-6-ethoxynicotinamide;
(R)—N-(3-chloro-4-(morpholin-2-yl)phenyl)-1-(4-(difluoromethoxy)phenyl)-1H-pyrazole-4-carboxamide;

(S)—N-(3-chloro-4-(morpholin-2-yl)phenyl)-2-ethoxy-isonicotinamide;
(S)—N-(3-chloro-4-(morpholin-2-yl)phenyl)-6-ethoxynicotinamide;
(S)—N-(3-chloro-4-(morpholin-2-yl)phenyl)-1-(4-(difluoromethoxy)phenyl)-1H-pyrazole-4-carboxamide;
(R)—N-(2-chloro-4-(morpholin-2-yl)phenyl)-6-cyanopicolinamide;
(S)—N-(2-chloro-4-(morpholin-2-yl)phenyl)-6-cyanopicolinamide;
(S)—N-(2-chloro-4-(morpholin-2-yl)phenyl)-5-cyanopicolinamide;
(R)—N-(2-chloro-4-(morpholin-2-yl)phenyl)-5-cyanopicolinamide;
(S)—N-(2-chloro-4-(morpholin-2-yl)phenyl)-6-cyanonicotinamide;
(R)—N-(2-chloro-4-(morpholin-2-yl)phenyl)-6-cyanonicotinamide;
(S)—N-(2-chloro-4-(morpholin-2-yl)phenyl)-1-(4-cyanophenyl)-1H-pyrazole-4-carboxamide;
(S)-1-(4-(difluoromethoxy)phenyl)-N-(2-fluoro-4-(morpholin-2-yl)phenyl)-1H-1,2,3-triazole-4-carboxamide;
(S)—N-(3-chloro-4-(morpholin-2-yl)phenyl)-1-(4-cyanophenyl)-1H-pyrazole-4-carboxamide;
(S)-4-chloro-6-cyano-N-(2-fluoro-4-(morpholin-2-yl)phenyl)picolinamide;
(S)-2-cyano-N-(3-fluoro-4-(morpholin-2-yl)phenyl)-6-methoxyisonicotinamide;
(S)-1-(4-cyano-2-fluorophenyl)-N-(3-fluoro-4-(morpholin-2-yl)phenyl)-1H-pyrazole-4-carboxamide;
(S)—N-(3-chloro-4-(morpholin-2-yl)phenyl)-1-(4-cyano-2-fluorophenyl)-1H-pyrazole-4-carboxamide;
(S)-1-(4-cyano-2-fluorophenyl)-N-(2-fluoro-4-(morpholin-2-yl)phenyl)-1H-pyrazole-4-carboxamide;
(S)-1-(4-cyanophenyl)-N-(2-fluoro-4-(morpholin-2-yl)phenyl)-1H-pyrazole-4-carboxamide;
(S)—N-(3-chloro-4-(morpholin-2-yl)phenyl)-2-cyano-6-methylisonicotinamide;
(S)-2-cyano-N-(2-fluoro-4-(morpholin-2-yl)phenyl)-6-methylisonicotinamide;
(S)—N4-(3-fluoro-4-(morpholin-2-yl)phenyl)-6-methylpyridine-2,4-dicarboxamide;
(S)-2-cyano-N-(3-fluoro-4-(morpholin-2-yl)phenyl)-6-methylisonicotinamide;
(S)-6-chloro-N4-(3-fluoro-4-(morpholin-2-yl)phenyl)pyridine-2,4-dicarboxamide;
(S)-6-ethyl-N4-(3-fluoro-4-(morpholin-2-yl)phenyl)pyridine-2,4-dicarboxamide;
(S)—N4-(3-chloro-4-(morpholin-2-yl)phenyl)-6-methylpyridine-2,4-dicarboxamide;
(S)—N4-(2-fluoro-4-(morpholin-2-yl)phenyl)-6-methylpyridine-2,4-dicarboxamide;
(S)—N4-(2-fluoro-4-(morpholin-2-yl)phenyl)-6-methoxypyridine-2,4-dicarboxamide;
(S)-2-cyano-N-(2-fluoro-4-(morpholin-2-yl)phenyl)-6-methoxyisonicotinamide;
(S)—N4-(2-chloro-4-(morpholin-2-yl)phenyl)-6-methylpyridine-2,4-dicarboxamide;
(S)—N-(2-chloro-4-(morpholin-2-yl)phenyl)-2-cyano-6-methylisonicotinamide;
(S)—N-(2-chloro-4-(morpholin-2-yl)phenyl)-2-cyano-6-methoxyisonicotinamide;
(S)—N-(2-fluoro-4-(morpholin-2-yl)phenyl)-1-(6-(trifluoromethyl)pyrazin-2-yl)-1H-pyrazole-4-carboxamide;
(S)—N-(2-chloro-4-(morpholin-2-yl)phenyl)-1-(6-(trifluoromethyl)pyrazin-2-yl)-1H-pyrazole-4-carboxamide;
(S)—N-(3-fluoro-4-(morpholin-2-yl)phenyl)-1-(6-(trifluoromethyl)pyrazin-2-yl)-1H-pyrazole-4-carboxamide;
(S)—N-(3-chloro-4-(morpholin-2-yl)phenyl)-1-(6-(trifluoromethyl)pyrazin-2-yl)-1H-pyrazole-4-carboxamide;
(S)—N-(3-fluoro-4-(morpholin-2-yl)phenyl)-1-(6-(trifluoromethyl)pyrimidin-4-yl)-1H-pyrazole-4-carboxamide;
(S)—N-(3-fluoro-4-(morpholin-2-yl)phenyl)-1-(6-(trifluoromethyl)pyridin-3-yl)-1H-pyrazole-4-carboxamide;
(S)-1-(5-cyanopyrazin-2-yl)-N-(3-fluoro-4-(morpholin-2-yl)phenyl)-1H-pyrazole-4-carboxamide;
(S)—N-(3-fluoro-4-(morpholin-2-yl)phenyl)-1-(2-(trifluoromethyl)pyrimidin-4-yl)-1H-pyrazole-4-carboxamide;
(S)-4-chloro-6-cyano-N-(3-fluoro-4-(morpholin-2-yl)phenyl)picolinamide;
(S)—N-(3-fluoro-4-(morpholin-2-yl)phenyl)-1-(5-(trifluoromethyl)pyrazin-2-yl)-1H-pyrazole-4-carboxamide;
(S)-5-cyano-N-(2-fluoro-4-(morpholin-2-yl)phenyl)-6-methylpicolinamide;
(S)-5-cyano-N-(3-fluoro-4-(morpholin-2-yl)phenyl)-6-methylpicolinamide;
(S)—N-(3-fluoro-4-(morpholin-2-yl)phenyl)-5-(trifluoromethyl)pyrazine-2-carboxamide and
(S)-6-ethoxy-N-(2-fluoro-4-(morpholin-2-yl)phenyl)nicotinamide.

One further embodiment of the invention is compounds of formula IE

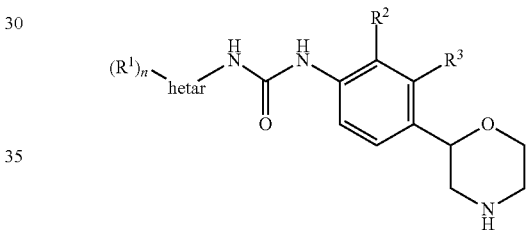

IE wherein
R¹ is hydrogen,
  halogen,
  cyano,
  lower alkyl,
  lower alkyl substituted by halogen,
  lower alkoxy,
  lower alkoxy substituted by halogen or C(O)NH₂,
  phenyl optionally substituted by halogen, cyano or lower alkoxy substituted by halogen,
  2,2-difluorobenzo[d][1,3]dioxol-5-yl,
  6-(trifluoromethyl)pyrazin-2-yl,
  5-(trifluoromethyl)pyrazin-2-yl,
  6-(trifluoromethyl)pyrimidin-4-yl,
  6-(trifluoromethyl)pyridin-3-yl,
  5-cyanopyrazin-2-yl,
  or 2-(trifluoromethyl)pyrimidin-4-yl;
n is 1 or 2;
R² is halogen, lower alkyl or cyano and R³ is hydrogen, or
R² is hydrogen and R³ is halogen, lower alkyl or cyano;
Hetar is selected from the group consisting of 1H-indazole-3yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or a pharmaceutically suitable acid addition salt thereof, for example the following compounds
1-(6-chloro-pyridin-3-yl)-3-((R)-2-fluoro-4-morpholin-2-yl-phenyl)-urea;

1-(6-chloro-pyridin-3-yl)-3-((S)-2-fluoro-4-morpholin-2-yl-phenyl)-urea;

1-((R)-2-fluoro-4-morpholin-2-yl-phenyl)-3-(6-trifluoromethyl-pyridin-3-yl)-urea;

1-((S)-2-fluoro-4-morpholin-2-yl-phenyl)-3-(6-trifluoromethyl-pyridin-3-yl)-urea;

(RS)-1-(2-chloro-4-morpholin-2-yl-phenyl)-3-(6-chloro-pyridin-3-yl)-urea;

(S)-1-(2-chloro-4-morpholin-2-yl-phenyl)-3-(6-chloro-pyridin-3-yl)-urea;

(R)-1-(2-chloro-4-morpholin-2-yl-phenyl)-3-(6-chloro-pyridin-3-yl)-urea;

(RS)-1-(2-bromo-4-(morpholin-2-yl)phenyl)-3-(6-chloropyridin-3-yl)urea;

(RS)-1-(6-chloro-pyridin-3-yl)-3-(2-chloro-4-pyrrolidin-3-yl-phenyl)-urea;

(R)-1-(6-chloropyridin-3-yl)-3-(2-methyl-4-(morpholin-2-yl)phenyl)urea;

(R)-1-(2-chloro-4-(morpholin-2-yl)phenyl)-3-(6-(trifluoromethyl)pyridin-3-yl)urea;

(S)-1-(2-chloro-4-(morpholin-2-yl)phenyl)-3-(6-(trifluoromethyl)pyridin-3-yl)urea;

1-((S)-2-chloro-4-morpholin-2-yl-phenyl)-3-(2-trifluoromethyl-pyrimidin-5-yl)-urea;

1-((R)-2-chloro-4-morpholin-2-yl-phenyl)-3-(2-trifluoromethyl-pyrimidin-5-yl)-urea;

(S)-1-(2-chloro-4-(morpholin-2-yl)phenyl)-3-(5-(trifluoromethyl)pyridin-2-yl)urea;

(R)-1-(2-chloro-4-(morpholin-2-yl)phenyl)-3-(5-(trifluoromethyl)pyridin-2-yl)urea;

(R)-1-(2-chloro-4-(morpholin-2-yl)phenyl)-3-(5-chloropyridin-2-yl)urea;

(S)-1-(2-chloro-4-(morpholin-2-yl)phenyl)-3-(5-chloropyridin-2-yl)urea;

(R)-1-(2-bromo-4-(morpholin-2-yl)phenyl)-3-(6-cyanopyridin-3-yl)urea;

(S)-1-(2-bromo-4-(morpholin-2-yl)phenyl)-3-(6-cyanopyridin-3-yl)urea;

1-((R)-2-bromo-4-morpholin-2-yl-phenyl)-3-(6-chloro-pyridin-3-yl)-urea;

1-((S)-2-bromo-4-morpholin-2-yl-phenyl)-3-(6-chloro-pyridin-3-yl)-urea;

1-((S)-2-bromo-4-morpholin-2-yl-phenyl)-3-(2-trifluoromethyl-pyrimidin-5-yl)-urea; and 1-((R)-2-bromo-4-morpholin-2-yl-phenyl)-3-(2-trifluoromethyl-pyrimidin-5-yl)-urea.

Further embodiments of the present invention are compounds of formula I, wherein Z is a bond or —CH₂—, for example the following compounds (RS)-1-(6-chloro-pyridin-3-yl)-3-(2-chloro-4-pyrrolidin-3-yl-phenyl)-urea;

(RS)-1-(2-chloro-4-(piperidin-3-yl)phenyl)-3-(6-chloropyridin-3-yl)urea and (RS)-6-chloro-N-(2-chloro-4-piperidin-3-yl-phenyl)-nicotinamide.

A further embodiment of the invention is compounds if formula

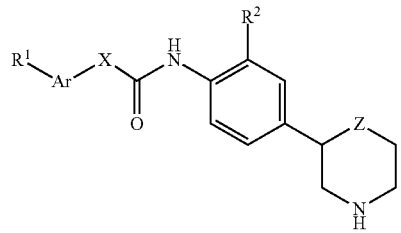

wherein
R¹ is hydrogen,
    halogen,
    cyano,
    lower alkyl,
    lower alkyl substituted by halogen,
    lower alkoxy, or
    phenyl optionally substituted by halogen;
R² is halogen, lower alkyl or cyano;
X is a bond, —NR'—, —CH₂NH— or —CHR'—;
R' is hydrogen or lower alkyl;
Z is a bond, —CH₂— or —O—;
Ar is phenyl or heteroaryl selected from the group consisting of 1H-indazole-3yl, pyridine-3-yl, pyridine-4-yl, 1H-pyrazole-3-yl, 1H-pyrazole-4-yl and 1H-pyrazole-5-yl;
or a pharmaceutically suitable acid addition salt thereof.

The present compounds of formula I and their pharmaceutically acceptable salts can be prepared by methods known in the art, for example, by processes described below, which process comprises a) cleaving off the N-protecting group from compounds of formula

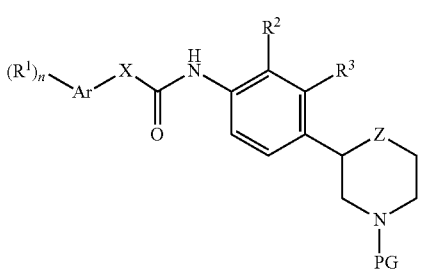

to form a compound of formula

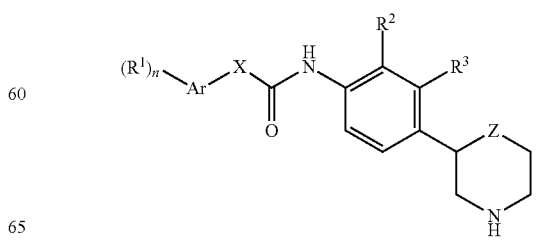

wherein PG is a N-protecting group selected from —C(O)O-tert-butyl and the other definitions are as described above, and, if desired, converting the compounds obtained into pharmaceutically acceptable acid addition salts.

The preparation of compounds of formula I of the present invention can be carried out in sequential or convergent synthetic routes. Syntheses of the compounds of the invention are shown in the following schemes 1-7 and in the description of 138 specific examples. The skills required for carrying out the reaction and purification of the resulting products are known to those skilled in the art. The substituents and indices used in the following description of the processes have the significance given herein before unless indicated to the contrary.

In more detail, the compounds of formula I can be manufactured by the methods given below, by the methods given in the examples or by analogous methods. Appropriate reaction conditions for the individual reaction steps are known to a person skilled in the art. The reaction sequence is not limited to the one displayed in schemes 1-7, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

General Procedure

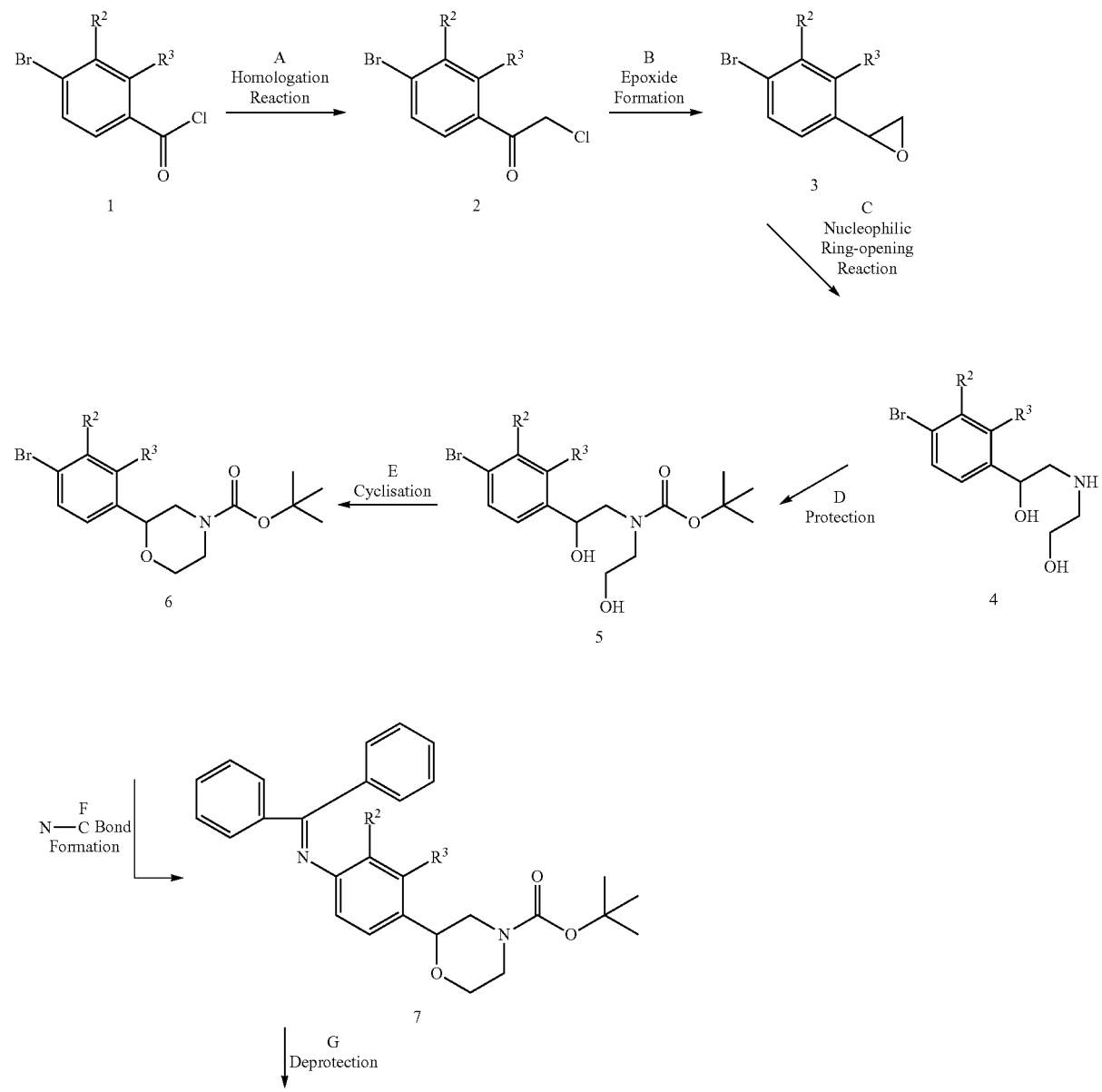

-continued

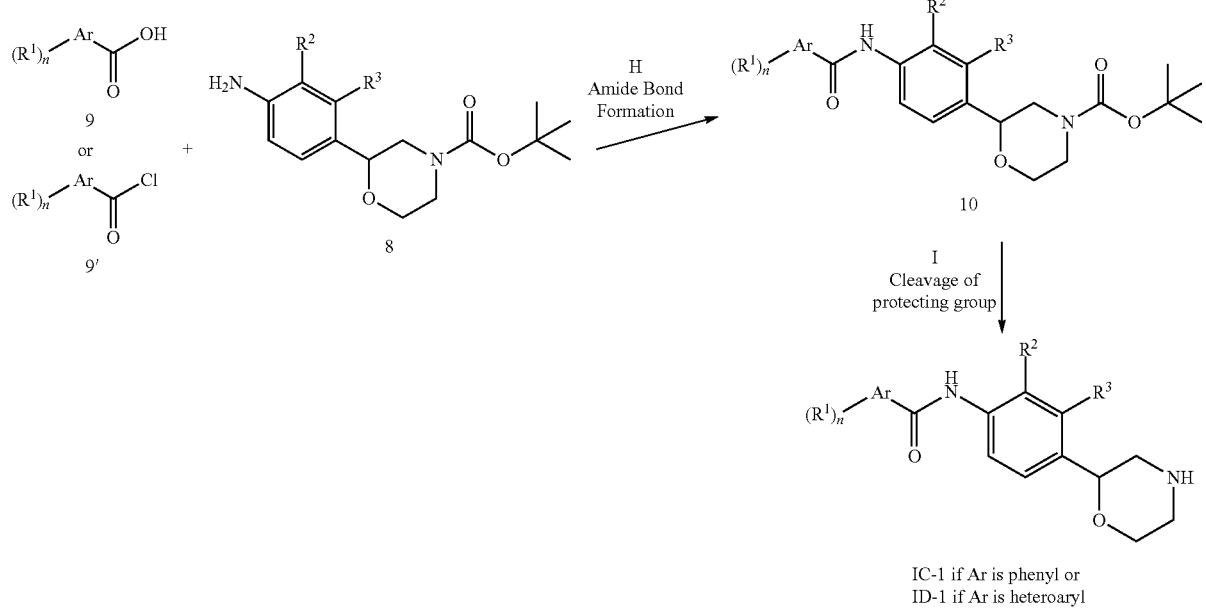

IC-1 if Ar is phenyl or
ID-1 if Ar is heteroaryl

The substituents are as described above and $R^2$ is F or Cl and $R^3$ is hydrogen or $R^2$ is hydrogen and $R^3$ is F or Cl.

Step A:

Alpha-chloro ketone 2 can be obtained by a homologation reaction of acyl chloride 1 involving sequential treatment first with (trimethylsilyl)diazomethane and then treatment with concentrated hydrochloric acid. The reaction is carried out using a mixture of acetonitrile, THF and diethyl ether as solvent at temperatures between 0° C. and room temperature.

Preferred conditions are mixing of reactants at 0-5° C. followed by allowing to react for 30 minutes at room temperature for the first step, and mixing of reactants at 0-5° C. followed by allowing to react for 30 minutes at room temperature for the second step.

Step B:

Epoxide formation can be accomplished by a stepwise process involving reduction of alpha-chloro ketone 2 by treatment with a reducing agent such as $NaBH_4$ or $LiBH_4$ in a solvent such as MeOH, EtOH, THF, dioxane, followed by cyclisation of the ensuing alpha-chloro alcohol by treatment with a base such as sodium methoxide, sodium ethoxide, potassium tert-butoxide or caesium carbonate in the same solvent.

Preferred conditions are $NaBH_4$ in ethanol at 5° C. to room temperature for 1 hour followed by treatment with sodium methoxide at room temperature for 16 hours and then at 40° C. for 1 hour.

Step C:

Nucleophilic ring-opening can be accomplished by treatment of epoxide 3 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:

Selective protection of the amino group of amino alcohol 4 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are dichloromethane in the absence of a base at room temperature for 16 hours.

Step E:

Cyclisation can be accomplished by a stepwise process involving sulphonate ester formation by treatment of diol 5 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 30 minutes at room temperature, then removal of the by-product triethylamine hydrochloride by filtration. Preferred conditions for the second step are potassium 2-methyl-2-butoxide in THF mixing the reactants at 0-5° C. and then allowing to react for 1 hour at room temperature.

Step F:

C—N bond formation can be accomplished by treatment of 6 with benzophenone imine in the presence of a palladium or copper catalyst, a ligand and a base in solvents such as dioxane, DME, THF, toluene, DMF and DMSO at elevated temperatures, for instance using a palladium-catalysed Buchwald-Hartwig reaction.

Preferred conditions are catalytic tris(dibenzylidineacetone)dipalladium(0), catalytic (R)-(+)-2,2'-bis(diphenylphosphino)-1,1'-binaphthyl and sodium tert-butoxide in dioxane at 100° C. for 1 hour.

Step G:

Removal of the nitrogen protecting group of 7 can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, H$_2$O, dioxane, THF, HOAc, EtOAc CH$_2$Cl$_2$, CHCl$_3$, DMF or mixtures thereof.

Preferred conditions are ammonium formate in the presence of palladium on charcoal in MeOH at 60° C. for 1 hour.

If desired, the racemic mixture of chiral amine 8 can be separated into its constituent enantiomers by using chiral HPLC.

Step H:

Amide bond formation can be accomplished by a coupling reaction between amine 8 and a carboxylic acid compound 9 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME.

Preferred conditions are TBTU with N-methylmorpholine in THF at 50-60° C. for 18-48 hours.

Alternatively, amide bond formation can be accomplished by a coupling reaction between amine 8 and an acyl chloride compound 9' in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine.

Preferred conditions are triethylamine in THF at room temperature for 18 hours.

If desired, the acyl chloride compound 9' can be prepared in situ from the corresponding carboxylic acid 9 by treatment with oxalyl chloride in halogenated solvents such as dichloromethane or 1,2-dichloroethane or ethereal solvents such as diethyl ether, dioxane, THF, DME or TBME in the presence of a catalyst such as DMF.

Preferred conditions are dichloroethane at room temperature for 1 hour.

Step I:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 5 hours or 4 N HCl in dioxane and THF at 60° C. for 16 hours.

If desired, the racemic mixture of morpholine compounds IC-1 or ID-1 can be separated into its constituent enantiomers by using chiral HPLC.

Scheme 2

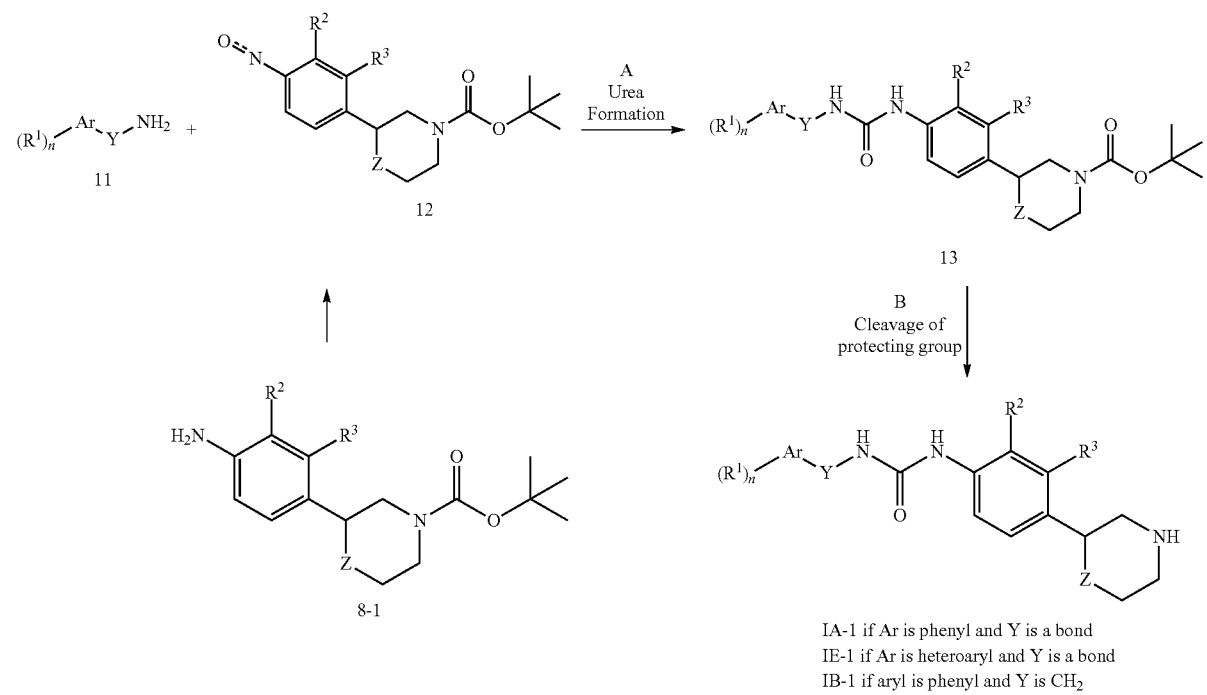

IA-1 if Ar is phenyl and Y is a bond
IE-1 if Ar is heteroaryl and Y is a bond
IB-1 if aryl is phenyl and Y is CH$_2$ The substituents are as described above and R$^2$ is F or Cl and R$^3$ is hydrogen or R$^2$ is hydrogen and R$^3$ is F or Cl. and Y is a bond or —CH$_2$—.

Step A:

Urea formation can be accomplished by a two-step one-pot procedure involving first converting amine 8-1 to the corresponding isocyanate 12 followed by reacting this isocyanate in situ with an amine compound 11.

The isocyanate formation can be accomplished by treatment of amine 8-1 with triphosgene, diphosgene or phosgene in halogenated solvents such as dichloromethane or 1,2-dichloroethane in the presence of an organic base such as triethylamine or N,N-diisopropylethylamine or an inorganic base such as sodium carbonate or potassium carbonate.

Preferred conditions for formation of isocyanate 12 are triphosgene and sodium carbonate in mixture of dichloromethane and water at room temperature for 2-3 hours, followed by treatment with the amine 11 in the same solvent mixture at room temperature for 2 hours.

Step B:

Removal of the BOC N-protecting group can be effected with mineral acids such as HCl, H$_2$SO$_4$ or H$_3$PO$_4$ or organic acids such as CF₃COOH, CHCl₂COOH, HOAc or p-toluenesulfonic acid in solvents such as CH₂Cl₂, CHCl₃, THF, MeOH, EtOH or H₂O at 0 to 80° C.

Preferred conditions are CF₃COOH in aqueous acetonitrile at 80° C. for 3 hours or 4 N HCl in dioxane and THF at 60° C. for 16 hours.

If desired, the racemic mixture of morpholine compounds IA-1, IE-1 or IB-1 can be separated into its constituent enantiomers by using chiral HPLC.

TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME.

Preferred conditions are TBTU with N-methylmorpholine in THF at 50-60° C. for 18-48 hours.

Alternatively, amide bond formation can be accomplished by a coupling reaction between amine 15 and an acyl chloride

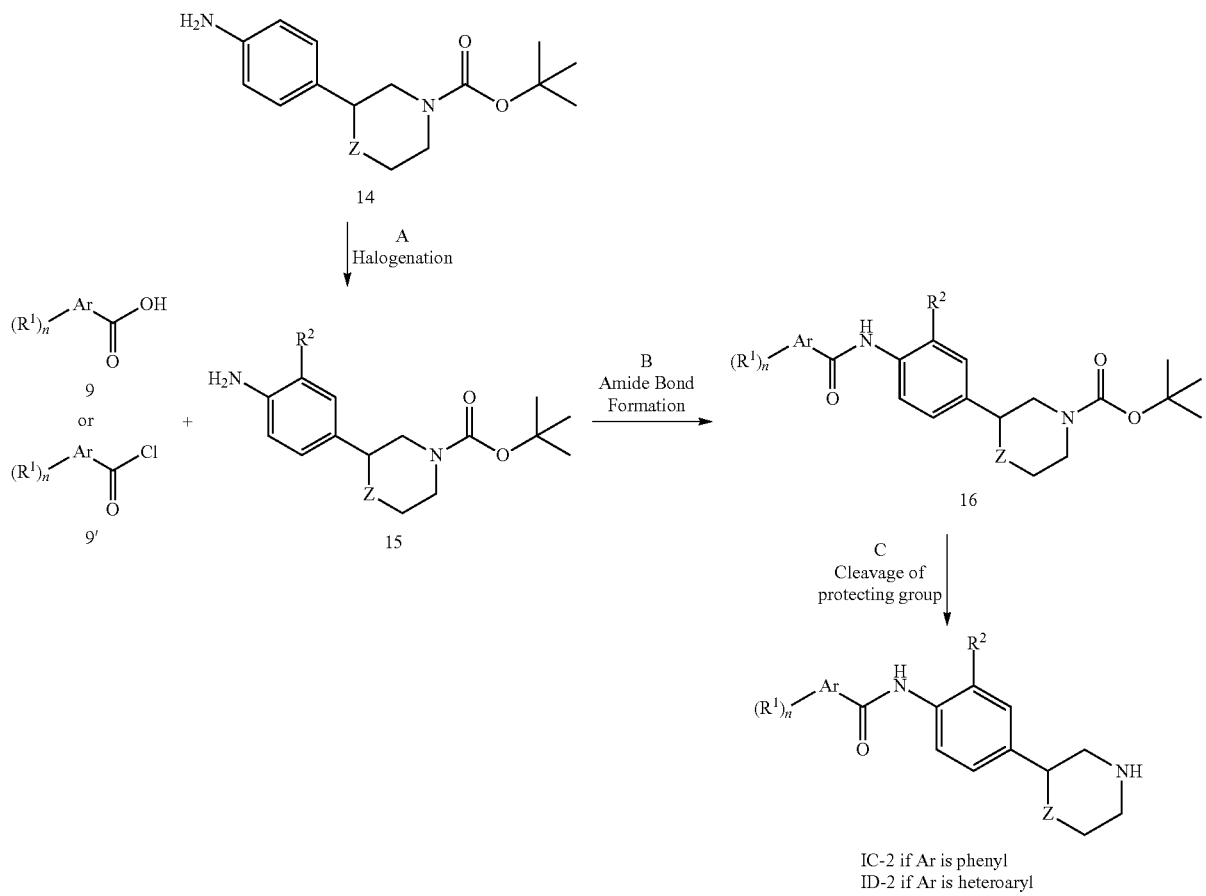

Scheme 3

The substituents are as described above, R² is Cl, Br or I and Z is a bond, —CH₂— or O.

Step A:

Aniline compounds 14 can regioselectively halogenated by reaction with one equivalent of halogenating agents such as N-chlorosuccinimide, N-bromosuccinimide or N-iodosuccinimide. Examples of appropriate anilines 14 include pyrrolidine derivatives where Z is a bond [CAS 908334-28-1], piperidine derivatives where Z is —CH₂— [CAS 875798-79-1], and morpholine derivatives where Z is O [CAS 1002726-96-6].

The reaction is carried out in non-protic polar organic solvents such as DMF or NMP.

Preferred conditions are NBS in DMF at room temperature for 15 minutes or NCS in DMF at 70° C. for 1 hour.

Step B:

Amide bond formation can be accomplished by a coupling reaction between amine 15 and a carboxylic acid compound 9 in the presence of a coupling reagent such as DCC, EDC, compound 9' in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine Preferred conditions are triethylamine in THF at room temperature for 18 hours.

If desired, the acyl chloride compound 9' can be prepared in situ from the corresponding carboxylic acid 9 by treatment with oxalyl chloride in halogenated solvents such as dichloromethane or 1,2-dichloroethane or ethereal solvents such as diethyl ether, dioxane, THF, DME or TBME in the presence of a catalyst such as DMF.

Preferred conditions are dichloroethane at room temperature for 1 hour.

Step C:

Removal of the BOC N-protecting group can be effected with mineral acids such as HCl, H₂SO₄ or H₃PO₄ or organic acids such as CF₃COOH, CHCl₂COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 5 hours or 4 N HCl in dioxane and THF at 60° C. for 16 hours.

If desired, the racemic mixture of morpholine compounds IC-2 or ID-2 can be separated into its constituent enantiomers by using chiral HPLC.

1,2-dichloroethane or ethereal solvents such as diethyl ether, dioxane, THF, DME or TBME.

Preferred conditions are TBTU with N-methylmorpholine in THF at 50-60° C. for 18-48 hours.

Alternatively, amide bond formation can be accomplished by a coupling reaction between amine 17 and an acyl chloride compound 9' in halogenated solvents such as dichloromethane or 1,2-dichloroethane or ethereal solvents such as Scheme 4

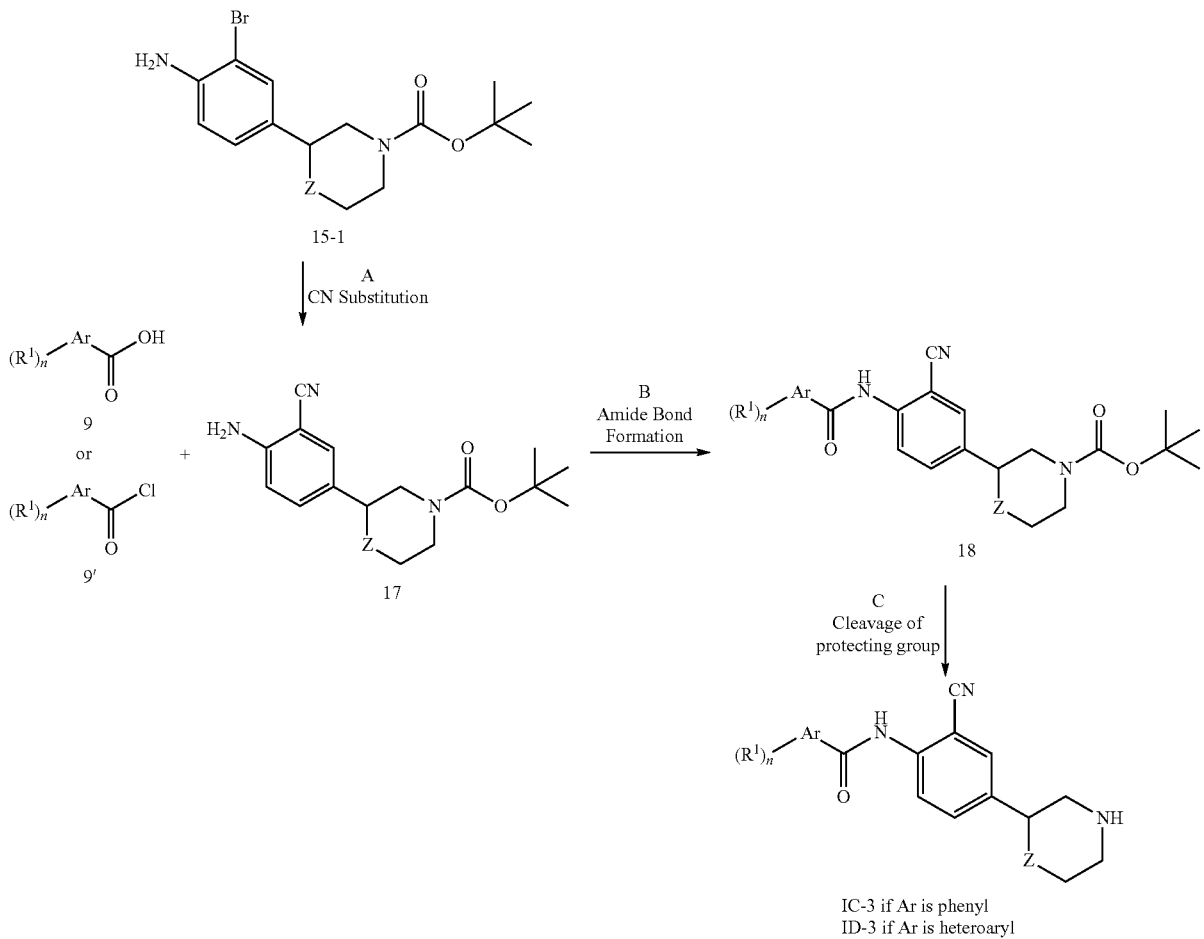

IC-3 if Ar is phenyl
ID-3 if Ar is heteroaryl

The substituents are as described above, R$^2$ is CN and Z is a bond, —CH$_2$— or O.

Step A:

Aromatic nitrile compounds 17 can be prepared by reaction of aromatic bromine compounds 15-1 with metal cyanide salts such as potassium cyanide, sodium cyanide or copper(I) cyanide, optionally in the presence of a palladium catalyst.

The reaction is carried out in non-protic polar organic solvents such as DMF or NMP at elevated temperatures.

Preferred conditions are CuCN in NMP at 160° C. for 5 hours.

Step B:

Amide bond formation can be accomplished by a coupling reaction between amine 17 and a carboxylic acid compound 9 in the presence of a coupling reagent such as DCC, EDC, TBTU or HATU in the presence of an organic base such as triethylamine, N,N-diisopropylethylamine or N-methylmorpholine in halogenated solvents such as dichloromethane or diethyl ether, dioxane, THF, DME or TBME, in the presence of an organic base such as triethylamine or N,N-diisopropylethylamine Preferred conditions are triethylamine in THF at room temperature for 2 hours.

If desired, the acyl chloride compound 9' can be prepared in situ from the corresponding carboxylic acid 9 by treatment with oxalyl chloride in halogenated solvents such as dichloromethane or 1,2-dichloroethane or ethereal solvents such as diethyl ether, dioxane, THF, DME or TBME in the presence of a catalyst such as DMF.

Preferred conditions are dichloroethane at room temperature for 1 hour.

Step C:

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 5 hours or 4 N HCl in dioxane and THF at 60° C. for 16 hours.

If desired, the racemic mixture of morpholine compounds IC-3 and ID-3 can be separated into its constituent enantiomers by using chiral HPLC.

Preferred conditions for formation of isocynate 19 are triphosgene and sodium carbonate in mixture of dichloromethane and water at room temperature for 3 hours, followed by treatment with the amine 11 in the same solvent mixture at room temperature for 24-48 hours.

Step B:

Scheme 5

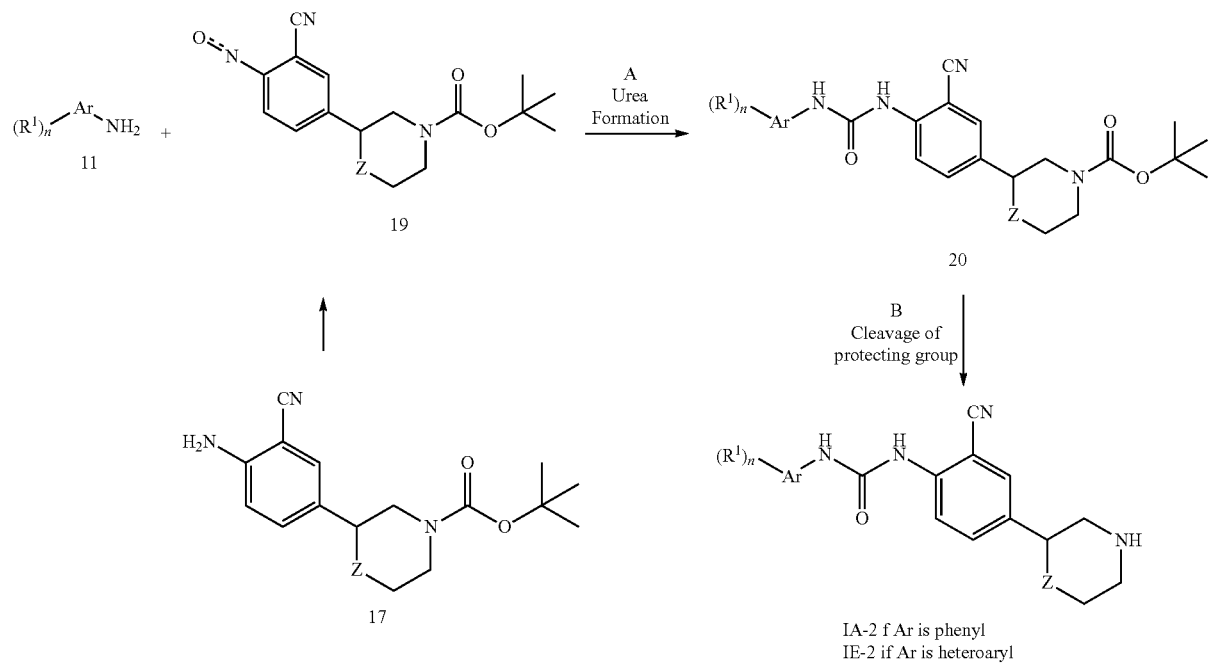

The substituents are as described above, Z is a bond, —CH$_2$— or O.

Step A:

Urea formation can be accomplished by a two-step one-pot procedure involving first converting amine 17 to the corresponding isocynate 19 followed by reacting this isocyanate in situ with an amine compound 11.

The isocyanate formation can be accomplished by treatment of amine 17 with triphosgene, diphosgene or phosgene in halogenated solvents such as dichloromethane or 1,2-dichloroethane in the presence of an organic base such as triethylamine or N,N-diisopropylethylamine or an inorganic base such as sodium carbonate or potassium carbonate.

Removal of the BOC N-protecting group can be effected with mineral acids such as HCl, H$_2$SO$_4$ or H$_3$PO$_4$ or organic acids such as CF$_3$COOH, CHCl$_2$COOH, HOAc or p-toluenesulfonic acid in solvents such as CH$_2$Cl$_2$, CHCl$_3$, THF, MeOH, EtOH or H$_2$O at 0 to 80° C.

Preferred conditions are CF$_3$COOH in aqueous acetonitrile at 80° C. for 4 hours or 4 N HCl in dioxane and THF at 60° C. for 16 hours.

If desired, the racemic mixture of morpholine compounds IA-2 nd IE-2 can be separated into its constituent enantiomers by using chiral HPLC.

Scheme 6

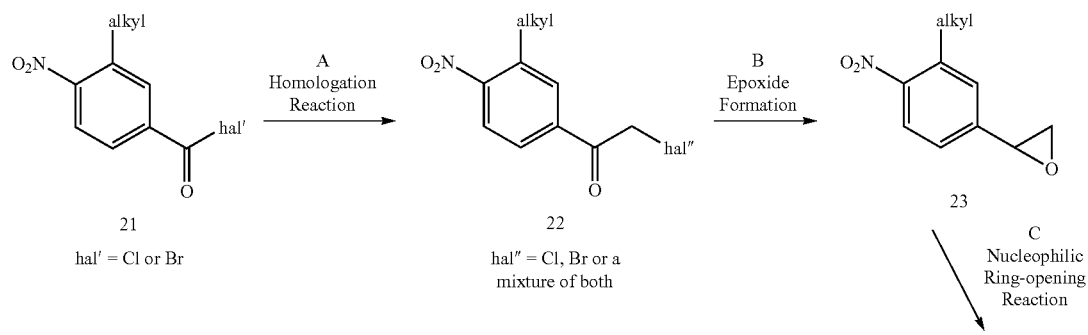

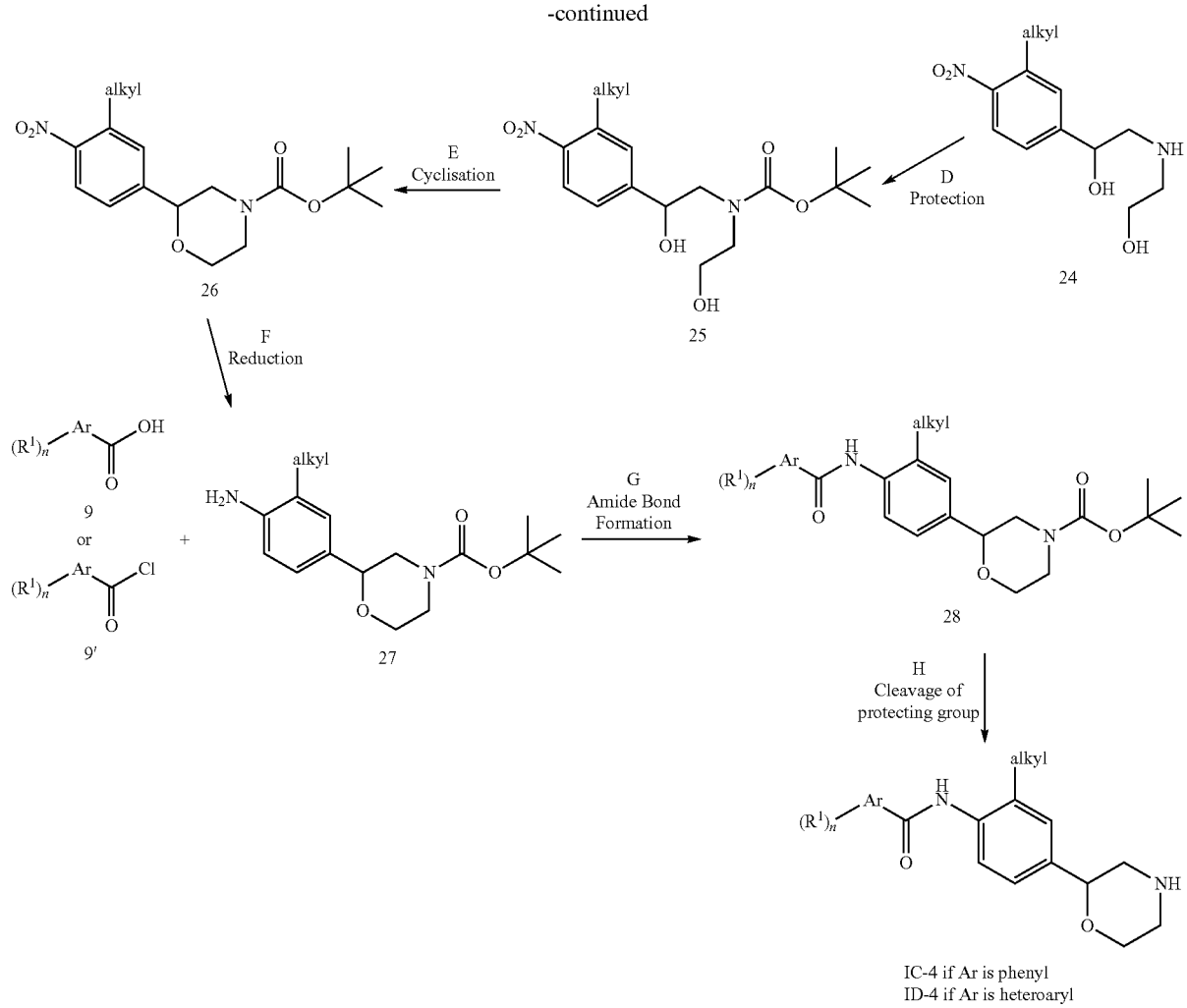

IC-4 if Ar is phenyl
ID-4 if Ar is heteroaryl

The substituents are as described above.

Step A:
Alpha-halo ketones 22 can be obtained by a homologation reaction of an acyl halide 21 [e.g. hal'=chloro and alkyl=methyl, CAS 35675-46-8] involving sequential treatment first with (trimethylsilyl)diazomethane and then treatment with concentrated hydrobromic acid or hydrochloric acid. The reaction is carried out using a mixture of acetonitrile, THF and hexane as solvent at temperatures between 0° C. and room temperature.

Preferred conditions are mixing of reactants at 0-5° C. followed by allowing to react for 1 hour at room temperature for the first step, and mixing of reactants at 0-5° C. followed by allowing to react for 30 minutes at room temperature for the second step.

Step B:
Epoxide formation can be accomplished by a stepwise process involving reduction of alpha-halo ketones 22 by treatment with a reducing agent such as NaBH$_4$ or LiBH$_4$ in a solvent such as MeOH, EtOH, THF, dioxane, followed by cyclisation of the ensuing alpha-halo alcohol by treatment with a base such as sodium methoxide, sodium ethoxide, potassium tert-butoxide or caesium carbonate in the same solvent.

Preferred conditions are NaBH$_4$ in ethanol at 5° C. to room temperature for 1 hour followed by treatment with sodium methoxide at room temperature for 16 hours.

Step C:
Nucleophilic ring-opening can be accomplished by treatment of epoxide 23 with 2-aminoethanol, optionally in the presence of an organic base such as triethylamine, N,N-diisopropylethylamine or N-methylmorpholine in a non-protic polar organic solvent such as ether, THF, dioxane or TBME.

Preferred conditions are using excess 2-aminoethanol as base in THF at room temperature for 16 hours.

Step D:
Selective protection of the amino group of amino alcohol 24 can be effected by treatment with di-tert-butyl carbonate, optionally in the presence of an organic base such as triethylamine, N,N-diisopropylethylamine or N-methylmorpholine, in halogenated solvents such as dichloromethane or 1,2-dichloroethane or ethereal solvents such as diethyl ether, dioxane, THF or TBME.

Preferred conditions are THF in the absence of a base at room temperature for 16 hours.

Step E:
Cyclisation can be accomplished by a stepwise process involving sulphonate ester formation by treatment of diol 25 with one equivalent of methanesulfonyl chloride in the presence of an organic base such as triethylamine, N,N-diisopropylethylamine or N-methylmorpholine in ethereal solvents such as diethyl ether, dioxane, THF or TBME, followed by cyclisation by treatment with a non-nucleophilic base such as potassium tert-butoxide or potassium 2-methyl-2-butoxide in ethereal solvents such as diethyl ether, dioxane, THF or TBME.

Preferred conditions for the first step are triethylamine in THF mixing the reactants at 0-5° C. and then allowing to react for 1 hour at room temperature, then removal of the by-product triethylamine hydrochloride by filtration. Preferred conditions for the second step are potassium 2-methyl-2-butoxide in THF mixing the reactants at 0-5° C. and then allowing to react for 30 minutes at room temperature.

Step F:

Reduction of the nitro group of 26 can be effected by hydrogenation with hydrogen under normal or elevated pressure or by transfer hydrogenation using ammonium formate or cyclohexadiene as hydrogen source with a catalyst such as $PtO_2$, Pd—C or Raney nickel in solvents such as MeOH, EtOH, $H_2O$, dioxane, THF, HOAc, EtOAc $CH_2Cl_2$, $CHCl_3$, DMF or mixtures thereof.

Preferred conditions are ammonium formate in the presence of palladium on charcoal in MeOH at 60° C. for 1 hour.

Step G:

Amide bond formation can be accomplished by a coupling reaction between amine 27 and a carboxylic acid compound 9 in the presence of a coupling reagent such as DCC, EDC, TBTU or HATU in the presence of an organic base such as triethylamine, N,N-diisopropylethylamine or N-methylmorpholine in halogenated solvents such as dichloromethane or 1,2-dichloroethane or ethereal solvents such as diethyl ether, dioxane, THF, DME or TBME.

Preferred conditions are TBTU with N-methylmorpholine in THF at 50-60° C. for 18-48 hours.

Alternatively, amide bond formation can be accomplished by a coupling reaction between amine 27 and an acyl chloride compound 9' in halogenated solvents such as dichloromethane or 1,2-dichloroethane or ethereal solvents such as diethyl ether, dioxane, THF, DME or TBME, in the presence of an organic base such as triethylamine or N,N-diisopropylethylamine. Preferred conditions are triethylamine in THF at room temperature for 2 hours.

If desired, the acyl chloride compound 9 can be prepared in situ from the corresponding carboxylic acid 9 by treatment with oxalyl chloride in halogenated solvents such as dichloromethane or 1,2-dichloroethane or ethereal solvents such as diethyl ether, dioxane, THF, DME or TBME in the presence of a catalyst such as DMF. Preferred conditions are dichloroethane at room temperature for 1 hour.

Step H:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 4 hours or 4 N HCl in dioxane and THF at 60° C. for 16 hours.

If desired, the racemic mixture of morpholine compounds IC-4 and ID-4 can be separated into its constituent enantiomers by using chiral HPLC.

Scheme 7

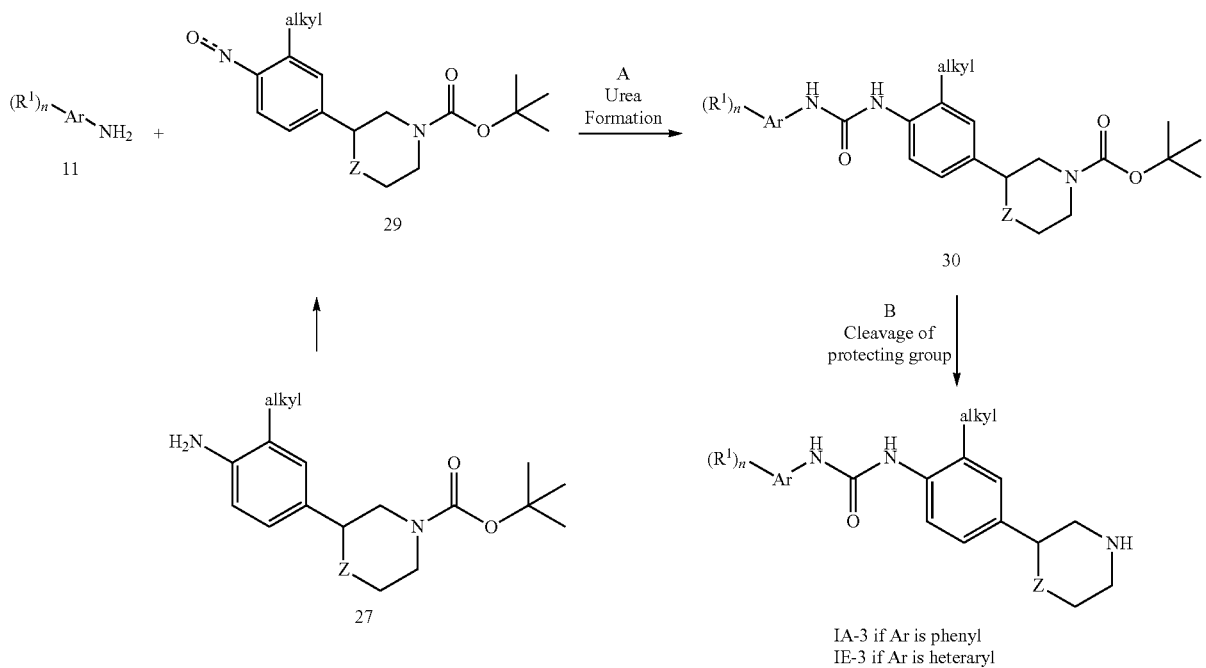

IA-3 if Ar is phenyl
IE-3 if Ar is heteraryl

The substituents are as described above and X is NH, $R^2$ is alkyl and Z is O.

Step A:

Urea formation can be accomplished by a two-step one-pot procedure involving first converting amine 27 to the corresponding isocynate 29 followed by reacting this isocyanate in situ with an amine compound 11.

The isocyanate formation can be accomplished by treatment of amine 27 with triphosgene, diphosgene or phosgene in halogenated solvents such as dichloromethane or 1,2-dichloroethane in the presence of an organic base such as triethylamine or N,N-diisopropylethylamine or an inorganic base such as sodium carbonate or potassium carbonate.

Preferred conditions for formation of isocynate 29 are triphosgene and sodium carbonate in mixture of dichloromethane and water at room temperature for 2-3 hours, followed by treatment with the amine 11 in the same solvent mixture at room temperature for 2 hours.

Step B:

Removal of the BOC N-protecting group can be effected with mineral acids such as HCl, $H_2SO_4$ or $H_3PO_4$ or organic acids such as $CF_3COOH$, $CHCl_2COOH$, HOAc or p-toluenesulfonic acid in solvents such as $CH_2Cl_2$, $CHCl_3$, THF, MeOH, EtOH or $H_2O$ at 0 to 80° C.

Preferred conditions are $CF_3COOH$ in aqueous acetonitrile at 80° C. for 3 hours or 4 N HCl in dioxane and THF at 60° C. for 16 hours.

If desired, the racemic mixture of morpholine compounds IA-3 and IE-3 can be separated into its constituent enantiomers by using chiral HPLC.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC. Racemic mixtures of chiral synthetic intermediates can also be separated using chiral HPLC.

Salts of Compounds of Formula I

The compounds of formula I are basic and can be converted to a corresponding acid addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or can be brought out of solution with a less polar solvent.

Example 1

6-Fluoro-1H-indazole-3-carboxylic acid ((R)-2-fluoro-4-morpholin-2-yl-phenyl)-amide

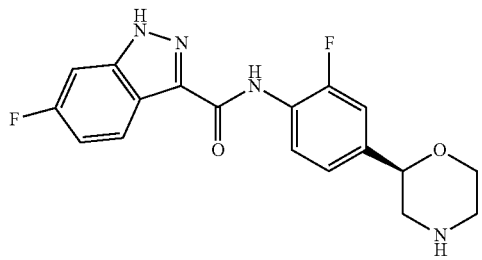 [SMILES: O=C(Nc1ccc([C@@H]2CNCCO2)cc1F)c1n[nH]c2cc(F)ccc12]

a) 2-Chloro-1-(4-bromo-3-fluoro-phenyl)-ethanone

To a stirred solution of 4-bromo-3-fluorobenzoyl chloride (5.6 g, CAS 695188-21-7) in acetonitrile (30 ml) and THF (30 ml) at 0-5° C. was added dropwise (trimethylsilyl)diazomethane (13.7 ml, 2 M solution in diethyl ether). The reaction mixture was stirred at room temperature for 30 min TLC analysis showed the reaction was complete. Hydrochloric acid (3.81 ml, 37% aq.) was then added dropwise at 0-5° C. over 10 minutes and the reaction mixture was then stirred at room temperature for a further 20 minutes. The reaction mixture was poured into EtOAc and extracted sequentially with aq. $Na_2CO_3$ solution, water and saturated brine. The organic layer was then dried over $Na_2SO_4$ and concentrated in vacuo to afford 2-chloro-1-(4-bromo-3-fluoro-phenyl)-ethanone (5.67 g) as a yellow solid which was used in the next step without further purification. MS (EI): 203 ([$\{^{81}Br\}$M-$CH_2Cl$]$^+$), 201 ([$\{^{79}Br\}$M-$CH_2Cl$]$^+$), 175 ([$\{^{81}Br\}$M-$CH_2Cl$—CO]$^+$), 173 ([$\{^{79}Br\}$M-$CH_2Cl$—CO]$^+$).

b) (RS)-2-(4-Bromo-3-fluoro-phenyl)-oxirane

To a stirred solution of 2-chloro-1-(4-bromo-3-fluoro-phenyl)-ethanone (6.16 g) in ethanol (100 ml) at 5° C. was added portionwise over 5 min $NaBH_4$ (788 mg). The reaction mixture was then stirred at room temperature for 1 hour to afford a light yellow solution. TLC analysis showed the reaction was complete. Sodium methoxide (562 mg) was then added and the reaction mixture was stirred at room temperature overnight. TLC analysis showed a small amount of starting material remaining and so the reaction mixture was stirred at 40° C. for 1 h. The reaction mixture was then poured into water and extracted twice with EtOAc. The combined organic layers were washed with saturated brine, then dried over $Na_2SO_4$ and concentrated in vacuo to afford (RS)-2-(4-bromo-3-fluoro-phenyl)-oxirane (4.69 g) as a yellow oil which was used in the next step without further purification.

c) (RS)-1-(4-Bromo-3-fluoro-phenyl)-2-(2-hydroxy-ethylamino)-ethanol

To a stirred solution of (RS)-2-(4-bromo-3-fluoro-phenyl)-oxirane (4.69 g) in THF (11 ml) was added 2-aminoethanol (13.2 ml) and the mixture was stirred at room temperature overnight. The reaction mixture was then poured into brine and extracted twice with EtOAc. The combined organic layers was dried over $Na_2SO_4$ and concentrated in vacuo to afford (RS)-1-(4-bromo-3-fluoro-phenyl)-2-(2-hydroxy-ethylamino)-ethanol (5.37 g) as a yellow viscous oil which was used in the next step without further purification. MS (ISP): 280.2 ([$\{^{81}Br\}$M+H]$^+$), 278.1 ([$\{^{79}Br\}$M+H]$^+$).

d) (RS)-[2-(4-Bromo-3-fluoro-phenyl)-2-hydroxy-ethyl]-(2-hydroxy-ethyl)-carbamic acid tert-butyl ester To a stirred solution of (RS)-1-(4-bromo-3-fluoro-phenyl)-2-(2-hydroxy-ethylamino)-ethanol (5.37 g) in dichloromethane (60 ml) was added $Boc_2O$ (4.00 g) and the mixture was stirred at room temperature overnight. The reaction mixture was then poured into water and extracted with dichloromethane. The organic layer was washed sequentially with 1 M aq. HCl, sat. aq. $NaHCO_3$ solution and saturated brine, then dried over Na2SO4 and concentrated in vacuo. The residue was purified by flash column chromatography (silica gel; gradient: 0% to 10% MeOH in dichloromethane) to afford (RS)-[2-(4-bromo-3-fluoro-phenyl)-2-hydroxy-ethyl]-(2- hydroxy-ethyl)-carbamic acid tert-butyl ester (3.89 g, 45% over 4 steps) as a light yellow viscous oil. MS (ISP): 380.1 ([{$^{81}$Br}M+H]$^+$), 378.2 ([{$^{79}$Br}M+H]$^+$).

e) (RS)-2-(4-Bromo-3-fluoro-phenyl)-morpholine-4-carboxylic acid tert-butyl ester To a stirred solution of (RS)-[2-(4-bromo-3-fluoro-phenyl)-2-hydroxy-ethyl]-(2-hydroxy-ethyl)-carbamic acid tert-butyl ester (3.88 g) and triethylamine (1.71 ml) in THF (40 ml) at 0-5° C. was added dropwise methanesulfonyl chloride (873 µl). The reaction mixture was then stirred at room temperature for 30 min to afford a white suspension. The reaction mixture was then filtered to remove triethylamine hydrochloride, washing the filter with THF (6 ml). The filtrate was cooled to 0-5° C. and potassium 2-methyl-2-butoxide (9.05 ml, 1.7 M solution in toluene) was added. The reaction mixture was stirred at room temperature for 1 hour and then poured into water and extracted twice with EtOAc. The combined organic phases were dried over Na$_2$SO$_4$ and concentrated in vacuo. The residue was purified by flash column chromatography (silica gel; gradient: 0% to 30% EtOAc in hexanes) to afford (RS)-2-(4-bromo-3-fluoro-phenyl)-morpholine-4-carboxylic acid tert-butyl ester (1.73 g, 47%) as an orange viscous oil. MS (ISP): 306.1 ([{$^{81}$Br}M+H—C$_4$H$_8$]$^+$), 304.1 ([{$^{79}$Br}M+H—C$_4$H$_8$]$^+$), 262.0 ([{$^{81}$Br}M+H—C$_4$H$_8$—CO$_2$]$^+$), 260.1 ([{$^{79}$Br}M+H—C$_4$H$_8$—CO$_2$]$^+$).

f) (RS)-2-[4-(Benzhydrylidene-amino)-3-fluoro-phenyl]-morpholine-4-carboxylic acid tert-butyl ester To a stirred solution of (RS)-2-(4-bromo-3-fluoro-phenyl)-morpholine-4-carboxylic acid tert-butyl ester (1.57 g) and benzophenone imine (1.15 ml) in toluene (40 ml) was added sodium tert-butoxide (691 mg). The reaction mixture was purged with argon for 10 min. (R)-(+)-2,2'-bis(diphenylphosphino)-1,1'-binaphthyl (280 mg) and tris(dibenzylideneacetone)dipalladium(0) (120 mg) were added and the reaction mixture was heated to 100° C. and stirred for 1 h. The reaction mixture was poured into water and extracted twice with EtOAc. The organic layers were dried over Na$_2$SO$_4$ and concentrated in vacuo. The residue was purified by flash column chromatography (silica gel; gradient: 0% to 30% EtOAc in hexanes) to afford (RS)-2-[4-(benzhydrylidene-amino)-3-fluoro-phenyl]-morpholine-4-carboxylic acid tert-butyl ester (2.215 g, quant.) as a yellow viscous oil. MS (ISP): 461.3 ([M+H]$^+$), 405.4 ([M+H—C$_4$H$_8$]$^+$), 361.3 ([M+H—C$_4$H$_8$—CO$_2$]$^+$).

g) (RS)-2-(4-Amino-3-fluoro-phenyl)-morpholine-4-carboxylic acid tert-butyl ester To a stirred solution of (RS)-2-[4-(benzhydrylidene-amino)-3-fluoro-phenyl]-morpholine-4-carboxylic acid tert-butyl ester (2.21 g) in methanol (40 ml) was added ammonium formate (4.54 g). The reaction mixture was degassed by bubbling argon into the mixture for several minutes. 10% Palladium on activated charcoal (255 mg) was then added and the reaction mixture was stirred at 60° C. for 1 hour. The reaction mixture was then filtered through celite and the filtrate was poured into 1 M aq. NaOH and extracted twice with EtOAc. The combined organic layers were dried over Na$_2$SO$_4$ and concentrated in vacuo. The residue was purified by flash column chromatography (silica gel; gradient: 0% to 30% EtOAc in hexanes) to afford (RS)-2-(4-amino-3-fluoro-phenyl)-morpholine-4-carboxylic acid tert-butyl ester (1.42 g, 74%) as a white solid. MS (ISP): 319.2 ([M+Na]$^+$), 297.3 ([M+H]$^+$), 241.2 ([M+H—C$_4$H$_8$]$^+$), 197.2 ([M+H—C$_4$H$_8$—CO$_2$]$^+$).

h) (+)-(R)-2-(4-Amino-3-fluoro-phenyl)-morpholine-4-carboxylic acid tert-butyl ester & (−)-(S)-2-(4-Amino-3-fluoro-phenyl)-morpholine-4-carboxylic acid tert-butyl ester The enantiomers of (RS)-2-(4-amino-3-fluoro-phenyl)-morpholine-4-carboxylic acid tert-butyl ester were separated using chiral HPLC (column: Chiralpak AD, 5×50 cm; eluent: 10% isopropanol/heptane; pressure: 18 bar; flow rate: 35 ml/min) affording: (+)-(R)-2-(4-Amino-3-fluoro-phenyl)-morpholine-4-carboxylic acid tert-butyl ester (146 mg, light yellow solid), Retention time=62 min (−)-(S)-2-(4-Amino-3-fluoro-phenyl)-morpholine-4-carboxylic acid tert-butyl ester (153 mg, off-white solid), Retention time=74 min.

i) (R)-2-{3-Fluoro-4-[(6-fluoro-1H-indazole-3-carbonyl)-amino]-phenyl}-morpholine-4-carboxylic acid tert-butyl ester To a stirred suspension of (+)-(R)-2-(4-amino-3-fluoro-phenyl)-morpholine-4-carboxylic acid tert-butyl ester (40 mg) in THF (6 ml) and DMF (2 ml) were added sequentially N-methylmorpholine (0.12 ml), TBTU (128 mg) and 6-fluoro-1H-indazole-3-carboxylic acid (47 mg, CAS 129295-30-3) and the mixture was heated at 50° C. for 24 h and then at 60° C. for 18 h. The mixture was then concentrated in vacuo and the residue was purified by column chromatography (SiO$_2$; gradient: heptane/EtOAc) to give (R)-2-{3-fluoro-4-[(6-fluoro-1H-indazole-3-carbonyl)-amino]-phenyl}-morpholine-4-carboxylic acid tert-butyl ester (15 mg, 24%) as a white solid. MS (ISP): 476.1 ([M+NH$_4$]$^+$), 459.1 ([M+H]$^+$), 403.1 ([M+H—C$_4$H$_8$]$^+$).

j) 6-Fluoro-1H-indazole-3-carboxylic acid ((R)-2-fluoro-4-morpholin-2-yl-phenyl)-amide To a stirred solution of trifluoroacetic acid (38 µl) in water (1.5 ml) was added a solution of (R)-2-{3-fluoro-4-[(6-fluoro-1H-indazole-3-carbonyl)-amino]-phenyl}-morpholine-4-carboxylic acid tert-butyl ester (15 mg) in acetonitrile (0.5 ml). The reaction mixture was then capped and the mixture was shaken at 80° C. for 5 h. The reaction mixture was then cooled to room temperature and poured into 1 M aq. NaOH and the resulting mixture was extracted twice with EtOAc. The organic layers were dried over Na2SO4 and concentrated in vacuo. The crude material was purified by flash column chromatography (Isolute® Flash-NH$_2$ from Separtis; gradient: MeOH/EtOAc/heptane) to afford 6-fluoro-1H-indazole-3-carboxylic acid ((R)-2-fluoro-4-morpholin-2-yl-phenyl)-amide (9 mg, 77%) as a white solid. MS (ISP): 359.1 ([M+H]$^+$).

Example 2

6-Fluoro-1H-indazole-3-carboxylic acid ((S)-2-fluoro-4-morpholin-2-yl-phenyl)-amide

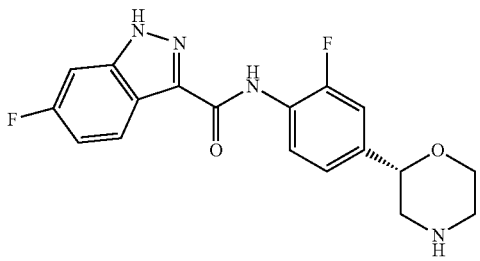 [SMILES: O=C(Nc1ccc([C@H]2CNCCO2)cc1F)c1n[nH]c2cc(F)ccc12]

The title compound was obtained in analogy to example 1 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester in step (i). White solid. MS (ISP): 359.1 ([M+H]$^+$).

Example 3

1-(3-Cyano-phenyl)-3-((R)-2-fluoro-4-morpholin-2-yl-phenyl)-urea

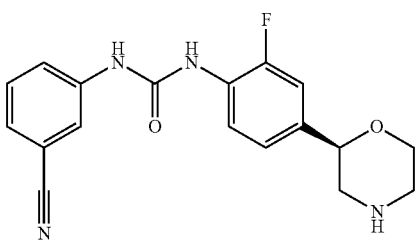 [SMILES: N#Cc1cccc(NC(=O)Nc2ccc([C@@H]3CNCCO3)cc2F)c1]

a) (R)-2-{4-[3-(3-Cyano-phenyl)-ureido]-3-fluoro-phenyl}-morpholine-4-carboxylic acid tert-butyl ester To a stirred solution of (+)-(R)-2-(4-amino-3-fluoro-phenyl)-morpholine-4-carboxylic acid tert-butyl ester (60 mg, example 1 h) in dichloromethane (2 ml) was added triphosgene (22 mg). A solution of sodium carbonate (43 mg) in water (2 ml) was then added. The reaction mixture was stirred at room temperature for 2.5 hours. TLC showed all the starting material had reacted. 3-Aminobenzonitrile (48 mg, CAS 2237-30-1) was then added and the reaction mixture was stirred at room temperature for a further 2 hours. TLC showed the reaction was complete. The reaction mixture was poured into dichloromethane and extracted with water. The organic phase was separated, dried over sodium sulphate and concentrated in vacuo. The residue was purified by column chromatography (SiO$_2$; gradient: 0% to 80% EtOAc in hexanes) to give (R)-2-{4-[3-(3-cyano-phenyl)-ureido]-3-fluoro-phenyl}-morpholine-4-carboxylic acid tert-butyl ester (95 mg, quant.) as a white solid. MS (ISP): 439.2 ([M−H]$^-$).

b) 1-(3-Cyano-phenyl)-3-((R)-2-fluoro-4-morpholin-2-yl-phenyl)-urea

To a stirred solution of trifluoroacetic acid (216 μl) in water (4.5 ml) was added a solution of (R)-2-{4-[3-(3-cyano-phenyl)-ureido]-3-fluoro-phenyl}-morpholine-4-carboxylic acid tert-butyl ester (85 mg) in acetonitrile (2 ml). The reaction mixture was then capped and the mixture was shaken at 80° C. for 3 h. The reaction mixture was then cooled to room temperature and poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: heptane/EtOAc/MeOH) to afford 1-(3-cyano-phenyl)-3-((R)-2-fluoro-4-morpholin-2-yl-phenyl)-urea (45 mg, 61%) as a white solid. MS (ISP): 341.1 ([M+H]$^+$).

Example 4

1-(3-Cyano-phenyl)-3-((S)-2-fluoro-4-morpholin-2-yl-phenyl)-urea

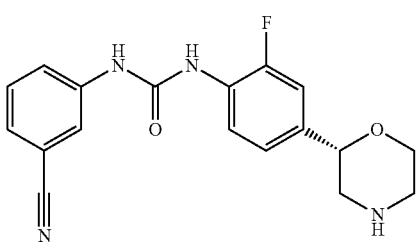 [SMILES: N#Cc1cccc(NC(=O)Nc2ccc([C@H]3CNCCO3)cc2F)c1]

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester in step (a). White solid. MS (ISP): 341.1 ([M+H]$^+$).

Example 5

(RS)-1-(2-Chloro-4-(morpholin-2-yl)phenyl)-3-(3-cyanophenyl)urea

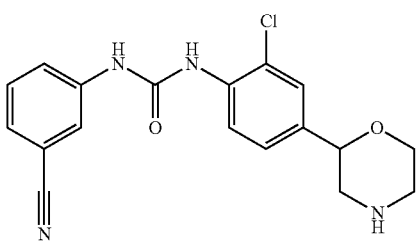 [SMILES: N#Cc1cccc(NC(=O)Nc2ccc(C3CNCCO3)cc2Cl)c1]

a) 1-(4-Bromo-3-chlorophenyl)-2-chloroethanone

To a stirred solution of 4-bromo-3-chlorobenzoyl chloride (11 g, CAS 21900-32-3) in acetonitrile (50 ml) and THF (50 ml) at 0-5° C. was added dropwise (trimethylsilyl)diazomethane (26.0 ml, 2 M solution in diethyl ether). The reaction mixture was stirred at room temperature for 30 min. TLC analysis showed the reaction was complete. Hydrochloric acid (7.22 ml, 37% aq.) was then added dropwise at 0-5° C. over 10 minutes and the reaction mixture was then stirred at room temperature for a further 20 minutes. The reaction mixture was poured into EtOAc and extracted sequentially with aq. Na$_2$CO$_3$ solution, water and saturated brine. The organic layer was then dried over Na$_2$SO$_4$ and concentrated in vacuo to afford 1-(4-bromo-3-chlorophenyl)-2-chloroethanone (11.0 g, 95%) as a light brown solid which was used in the next step without further purification. MS (EI): 221 ([{$^{81}$Br$^{37}$Cl}M-CH$_2$Cl]$^+$), 219 ([{$^{79}$Br$^{37}$Cl/$^{81}$Br$^{35}$Cl}M-CH$_2$Cl]$^+$), 217 ([{$^{79}$Br$^{35}$Cl}M-CH$_2$Cl]$^+$), 193 ([{$^{81}$Br$^{37}$Cl}M-CH$_2$Cl—CO]$^+$), 191 ([{$^{79}$Br$^{37}$Cl/$^{81}$Br$^{35}$Cl}M-CH$_2$Cl—CO]$^+$), 189 ([{$^{79}$Br$^{35}$Cl}M-CH$_2$Cl—CO]$^+$).

b) (RS)-2-(4-Bromo-3-chlorophenyl)oxirane

To a stirred solution of 1-(4-bromo-3-chlorophenyl)-2-chloroethanone (18.4 g) in ethanol (200 ml) at 5° C. was added portionwise over 5 min NaBH$_4$ (2.23 g). The reaction mixture was then stirred at room temperature for 90 min to afford a light yellow solution. TLC analysis showed the reaction was complete. Sodium methoxide (1.59 g) was then added and the reaction mixture was stirred at 50° C. for 4 h. TLC analysis showed the reaction was complete. The reaction mixture was then poured into TBME and extracted with saturated brine. The organic layer was dried over Na$_2$SO$_4$ and concentrated in vacuo to afford (RS)-2-(4-bromo-3-chlorophenyl)oxirane (15.2 g) as a brown oil which was used in the next step without further purification.

c) (RS)-1-(4-Bromo-3-chlorophenyl)-2-(2-hydroxyethylamino)ethanol

To a stirred solution of (RS)-2-(4-bromo-3-chlorophenyl)oxirane (15.2 g) in THF (40 ml) was added 2-aminoethanol (35.1 ml) and the mixture was stirred at room temperature for 7 hours. The reaction mixture was then poured into brine and extracted twice with EtOAc. The combined organic layers was dried over Na$_2$SO$_4$ and concentrated in vacuo to afford (RS)-1-(4-bromo-3-chlorophenyl)-2-(2-hydroxyethylamino)ethanol (19.0 g) as a yellow oil which was used in the next step without further purification. MS (ISP): 298.1 ([{$^{81}$Br$^{37}$Cl}M+H]$^+$), 296.0 ([{$^{79}$Br$^{37}$Cl/$^{81}$Br$^{35}$Cl}M+H]$^+$), 293.9 ([{$^{79}$Br$^{35}$Cl}M+H]$^+$).

d) tert-Butyl (RS)-2-(4-bromo-3-chlorophenyl)-2-hydroxyethyl(2-hydroxyethyl)carbamate To a stirred solution of (RS)-1-(4-bromo-3-chlorophenyl)-2-(2-hydroxyethylamino)ethanol (19.0 g) in THF (200 ml) at 0° C. was added Boc$_2$O (14.1 g) and the mixture was then stirred at room temperature overnight. The reaction mixture was then poured into ethyl acetate and extracted sequentially with 1 M aq. NaOH and saturated brine. The organic phase was dried over Na$_2$SO$_4$ and concentrated in vacuo. The residue was purified by flash column chromatography (silica gel; MeOH/dichloromethane 1/20) to afford tert-butyl (RS)-2-(4-bromo-3-chlorophenyl)-2-hydroxyethyl(2-hydroxyethyl)carbamate (12.7 g, 47% over 3 steps) as a yellow oil. MS (ISP): 397.9 ([{$^{81}$Br$^{37}$Cl}M+H]$^+$), 395.9 ([{$^{79}$Br$^{37}$Cl/$^{81}$Br$^{35}$Cl}M+H]$^+$), 393.9 ([{$^{79}$Br$^{35}$Cl}M+H]$^+$), 341.9 ([{$^{81}$Br$^{37}$Cl}M+H—C$_4$H$_8$]$^+$), 339.9 ([{$^{79}$Br$^{37}$Cl/$^{81}$Br$^{35}$Cl}M+H—C$_4$H$_8$]$^+$), 338.0 ([{$^{79}$Br$^{35}$Cl}M+H—C$_4$H$_8$]$^+$).

e) tert-Butyl (RS)-2-(4-bromo-3-chlorophenyl)morpholine-4-carboxylate

To a stirred solution of tert-butyl (RS)-2-(4-bromo-3-chlorophenyl)-2-hydroxyethyl(2-hydroxyethyl)carbamate (12.7 g) and triethylamine (6.72 ml) in THF (150 ml) at 0-5° C. was added dropwise methanesulfonyl chloride (2.76 ml). The reaction mixture was then stirred at room temperature for 1 hour to afford a white suspension. The reaction mixture was then filtered to remove triethylamine hydrochloride, washing the filter with THF (20 ml). The filtrate was cooled to 0-5° C. and potassium 2-methyl-2-butoxide (28.4 ml, 1.7 M solution in toluene) was added. The reaction mixture was stirred at room temperature for 30 min and then poured into EtOAc and extracted sequentially with dilute aq. HCl, water and saturated brine. The organic phase was dried over Na$_2$SO$_4$ and concentrated in vacuo. The residue was purified by flash column chromatography (silica gel; gradient: 0% to 50% EtOAc in hexanes) to afford tert-butyl (RS)-2-(4-bromo-3-chlorophenyl)morpholine-4-carboxylate (9.32 g, 77%) as a yellow oil. MS (ISP): 324.0 ([{$^{81}$Br$^{37}$Cl}M+H—C$_4$H$_8$]$^+$), 321.9 ([{$^{79}$Br$^{37}$Cl/$^{81}$Br$^{35}$Cl}M+H—C$_4$H$_8$]$^+$), 319.8 ([{$^{79}$Br$^{35}$Cl}M+H—C$_4$H$_8$]$^+$).

f) tert-Butyl (RS)-2-(3-chloro-4-(diphenylmethyleneamino)phenyl)morpholine-4-carboxylate To a stirred solution of tert-butyl (RS)-2-(4-bromo-3-chlorophenyl)morpholine-4-carboxylate (0.50 g) and benzophenone imine (253 mg) in toluene (5 ml) was added sodium tert-butoxide (204 mg). The reaction mixture was purged with argon for 10 min. (R)-(+)-2,2'-Bis(diphenylphosphino)-1,1'-binaphthyl (82.7 mg) and tris(dibenzylideneacetone)dipalladium(0) (36.5 mg) were added and the reaction mixture was heated at 90° C. overnight. The reaction mixture was poured into EtOAc and extracted sequentially with dilute aq. HCl, water and saturated brine. The organic layer was dried over Na$_2$SO$_4$ and concentrated in vacuo. The residue was purified by flash column chromatography (silica gel; gradient: 0% to 50% EtOAc in hexanes) to afford tert-butyl (RS)-2-(3-chloro-4-(diphenylmethyleneamino)phenyl)morpholine-4-carboxylate (639 mg, quant.) as a yellow oil. MS (ISP): 479.1 ([{$^{37}$Cl}M+H]$^+$), 477.1 ([{$^{35}$Cl}M+H]$^+$).

g) tert-Butyl (RS)-2-(4-amino-3-chlorophenyl)morpholine-4-carboxylate

To a stirred solution of tert-butyl (RS)-2-(3-chloro-4-(diphenylmethyleneamino)phenyl)morpholine-4-carboxylate (0.63 g) in methanol (8 ml) were added sodium acetate (325 mg) and hydroxylamine hydrochloride (202 mg). The reaction mixture was stirred at room temperature for 16 hours and then at 60° C. for 5 hours. The reaction mixture was then concentrated in vacuo and the residue was purified by flash column chromatography (silica gel; gradient: 0% to 70% EtOAc in hexanes) to afford tert-butyl (RS)-2-(4-amino-3-chlorophenyl)morpholine-4-carboxylate (345 mg, 84%) as a white solid. MS (ISP): 337.2 ([{$^{37}$Cl}M+Na]$^+$), 335.1 ([{$^{35}$Cl}M+Na]$^+$), 314.9 ([{$^{37}$Cl}M+H]$^+$), 313.0 ([{$^{35}$Cl}M+H]$^+$), 259.1 ([{$^{37}$Cl}M+H—C$_4$H$_8$]$^+$), 257.1 ([{$^{35}$Cl}M+H—C$_4$H$_8$]$^+$).

h) tert-Butyl (RS)-2-(3-chloro-4-(3-(3-cyanophenyl)ureido)phenyl)morpholine-4-carboxylate To a stirred solution of tert-butyl (RS)-2-(4-amino-3-chlorophenyl)morpholine-4-carboxylate (70 mg) in dichloromethane (2 ml) was added triphosgene (25 mg). A solution of sodium carbonate (47 mg) in water (2 ml) was then added. The reaction mixture was stirred at room temperature for 2.5 hours. TLC showed all the starting material had reacted. 3-Aminobenzonitrile (53 mg, CAS 2237-30-1) was then added and the reaction mixture was stirred at room temperature for a further 2 hours. TLC showed the reaction was complete. The reaction mixture was poured into dichloromethane and extracted with water. The organic phase was separated, dried over sodium sulphate and concentrated in vacuo. The residue was purified by column chromatography (SiO$_2$; gradient: 0% to 30% EtOAc in hexanes) to give tert-butyl (RS)-2-(3-chloro-4-(3-(3-cyanophenyl)ureido)phenyl)morpholine-4-carboxylate (114 mg, quant.) as an amorphous white solid. MS (ISP): 457.2 ([{$^{37}$Cl}M–H]$^-$), 455.2 ([{$^{35}$Cl}M–H]$^-$).

i) (RS)-1-(2-Chloro-4-(morpholin-2-yl)phenyl)-3-(3-cyanophenyl)urea

To a stirred solution of trifluoroacetic acid (225 µl) in water (4.5 ml) was added a solution of tert-butyl (RS)-2-(3-chloro-4-(3-(3-cyanophenyl)ureido)phenyl)morpholine-4-carboxylate (114 mg) in acetonitrile (2 ml). The reaction mixture was then capped and the mixture was shaken at 80° C. for 3 h. The reaction mixture was then cooled to room temperature and poured into 1 M aq. NaOH and the resulting mixture was extracted twice with EtOAc. The organic layers were dried over Na2SO4 and concentrated in vacuo. The crude material was purified by flash column chromatography (Isolute® Flash-NH$_2$ from Separtis); gradient: heptane/EtOAc/MeOH) to afford (RS)-1-(2-chloro-4-(morpholin-2-yl)phenyl)-3-(3-cyanophenyl)urea (58 mg, 72%) as a white solid. MS (ISP): 359.1 ([{$^{37}$Cl}M+H]$^+$), 357.1 ([{$^{35}$Cl}M+H]$^+$).

Examples 6 & 7

(S)-1-(2-Chloro-4-(morpholin-2-yl)phenyl)-3-(3-cyanophenyl)urea & (R)-1-(2-Chloro-4-(morpholin-2-yl)phenyl)-3-(3-cyanophenyl)urea

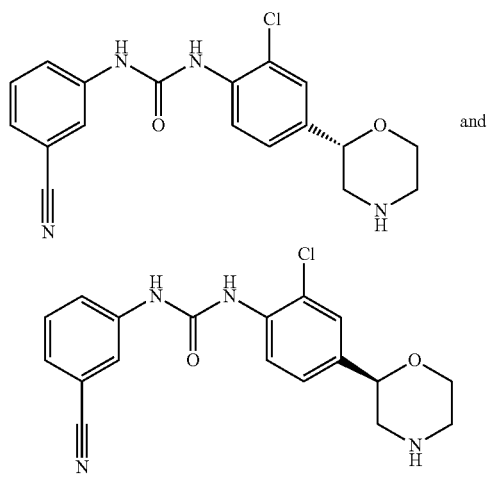
and

The enantiomers of (RS)-1-(2-chloro-4-(morpholin-2-yl)phenyl)-3-(3-cyanophenyl)urea (49 mg, Example 5) were separated using chiral HPLC (column: Chiralpak AD, 5×50 cm; eluent: 40% ethanol/heptane; pressure: 18 bar; flow rate: 35 ml/min) affording: (+)-(S)-1-(2-Chloro-4-(morpholin-2-yl)phenyl)-3-(3-cyanophenyl)urea (27 mg, off-white solid) Retention time=60 min. MS (ISP): 359.1 ([{$^{37}$Cl}M+H]$^+$), 357.1 ([{$^{35}$Cl}M+H]$^+$). (−)-(R)-1-(2-Chloro-4-(morpholin-2-yl)phenyl)-3-(3-cyanophenyl)urea (26 mg, off-white solid) Retention time=75 min. MS (ISP): 359.1 ([{$^{37}$Cl}M+H]$^+$), 357.1 ([{$^{35}$Cl}M+H]$^+$).

Example 8

1-(6-Chloro-pyridin-3-yl)-3-((R)-2-fluoro-4-morpholin-2-yl-phenyl)-urea

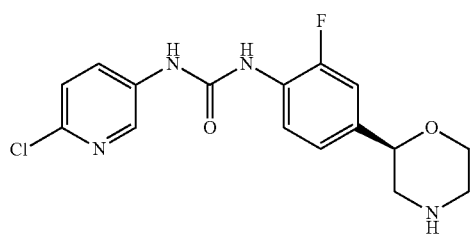

The title compound was obtained in analogy to example 3 using 6-chloropyridin-3-amine (CAS 5350-93-6) in place of 3-aminobenzonitrile in step (a). White solid. MS (ISP): 353.1 ([{$^{37}$Cl}M+H]$^+$), 351.1 ([{$^{35}$Cl}M+H]$^+$).

Example 9

1-(6-Chloro-pyridin-3-yl)-3-((S)-2-fluoro-4-morpholin-2-yl-phenyl)-urea

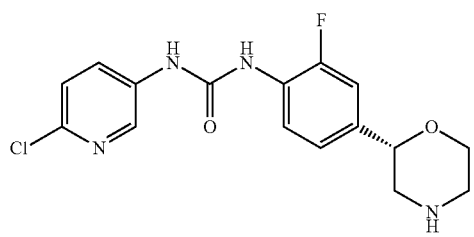

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 6-chloropyridin-3-amine (CAS 5350-93-6) in place of 3-aminobenzonitrile in step (a). White solid. MS (ISP): 353.1 ([{$^{37}$Cl}M+H]$^+$), 351.1 ([{$^{35}$Cl}M+H]$^+$).

Example 10

1-((R)-2-Fluoro-4-morpholin-2-yl-phenyl)-3-(6-trifluoromethyl-pyridin-3-yl)-urea

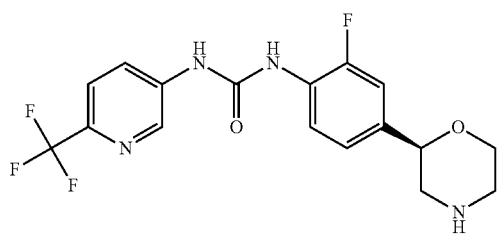 [SMILES: O=C(Nc1ccc(C(F)(F)F)nc1)Nc1ccc([C@@H]2CNCCO2)cc1F]

The title compound was obtained in analogy to example 3 using 6-(trifluoromethyl)pyridin-3-amine (CAS 106877-33-2) in place of 3-aminobenzonitrile in step (a). White solid. MS (ISP): 385.1 ([M+H]$^+$).

Example 11

1-((S)-2-Fluoro-4-morpholin-2-yl-phenyl)-3-(6-trifluoromethyl-pyridin-3-yl)-urea

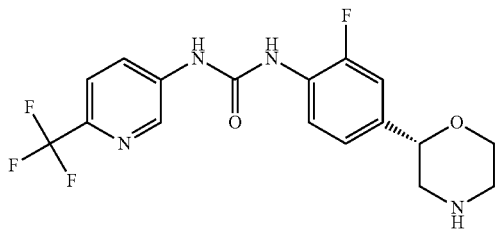

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 6-(trifluoromethyl)pyridin-3-amine (CAS 106877-33-2) in place of 3-aminobenzonitrile in step (a). White solid. MS (ISP): 385.1 ([M+H]$^+$).

Example 12

1-(4-Fluoro-phenyl)-1H-pyrazole-3-carboxylic acid ((R)-2-fluoro-4-morpholin-2-yl-phenyl)-amide

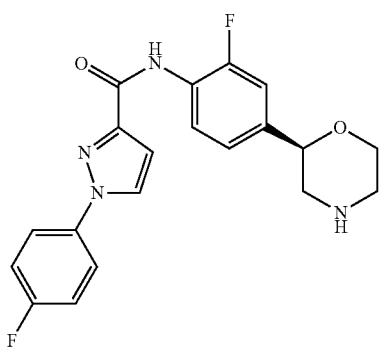 [SMILES: O=C(Nc1ccc([C@@H]2CNCCO2)cc1F)c1ccn(-c2ccc(F)cc2)n1]

The title compound was obtained in analogy to example 1 using 1-(4-fluorophenyl)-1H-pyrazole-3-carboxylic acid (CAS 1152535-34-6) in place of 6-fluoro-1H-indazole-3-carboxylic acid in step (i). White solid. MS (ISP): 385.1 ([M+H]$^+$).

Example 13

1-(4-Fluoro-phenyl)-1H-pyrazole-3-carboxylic acid ((S)-2-fluoro-4-morpholin-2-yl-phenyl)-amide

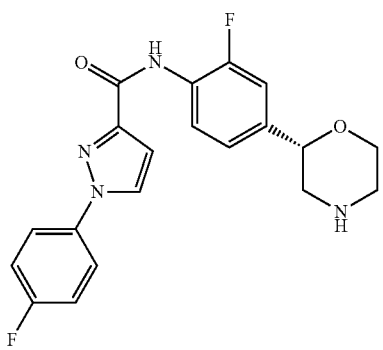 [SMILES: O=C(Nc1ccc([C@H]2CNCCO2)cc1F)c1ccn(-c2ccc(F)cc2)n1]

The title compound was obtained in analogy to example 1 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 1-(4-fluorophenyl)-1H-pyrazole-3-carboxylic acid (CAS 1152535-34-6) in place of 6-fluoro-1H-indazole-3-carboxylic acid in step (i). White solid. MS (ISP): 385.1 ([M+H]$^+$).

Example 14

(RS)-1-(2-Chloro-4-morpholin-2-yl-phenyl)-3-(6-chloro-pyridin-3-yl)-urea

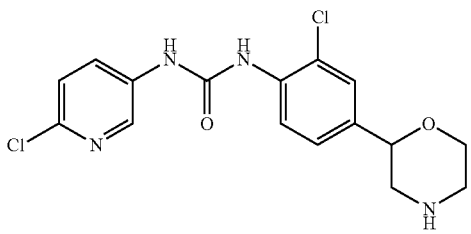 [SMILES: O=C(Nc1ccc(Cl)nc1)Nc1ccc(C2CNCCO2)cc1Cl]

The title compound was obtained in analogy to example 5 using 6-chloropyridin-3-amine (CAS 5350-93-6) in place of 3-aminobenzonitrile in step (h). Off-white solid. MS (ISP): 371.1 ([{$^{37}$Cl}M+H]$^+$), 368.9 ([{$^{37}$Cl$^{35}$Cl}M+H]$^+$), 367.1 ([{$^{35}$Cl}M+H]$^+$).

Example 15

1-(3-Cyano-benzyl)-3-((R)-2-fluoro-4-morpholin-2-yl-phenyl)-urea

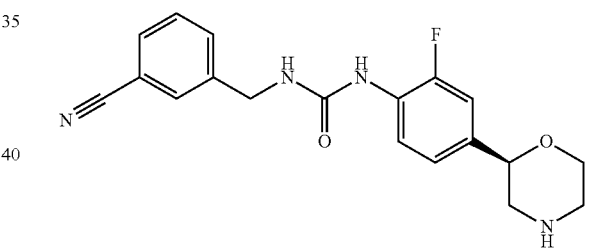

The title compound was obtained in analogy to example 3 using 3-(aminomethyl)benzonitrile (CAS 10406-24-3) in place of 3-aminobenzonitrile in step (a). Off-white amorphous solid. MS (ISP): 355.2 ([M+H]$^+$).

Example 16

1-(3-Cyano-benzyl)-3-((S)-2-fluoro-4-morpholin-2-yl-phenyl)-urea

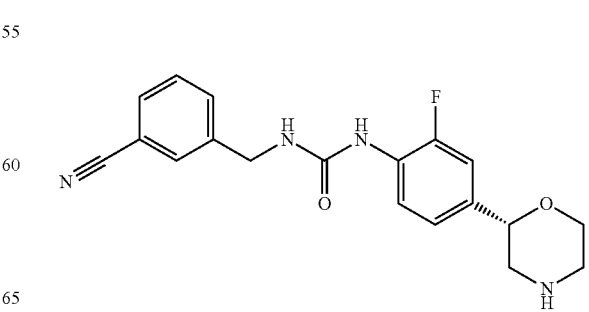

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 3-(aminomethyl)benzonitrile (CAS 10406-24-3) in place of 3-aminobenzonitrile in step (a). White solid. MS (ISP): 385.1 ([M+H]$^+$).

Example 17

2-Methyl-5-phenyl-2H-pyrazole-3-carboxylic acid ((S)-2-fluoro-4-morpholin-2-yl-phenyl)-amide

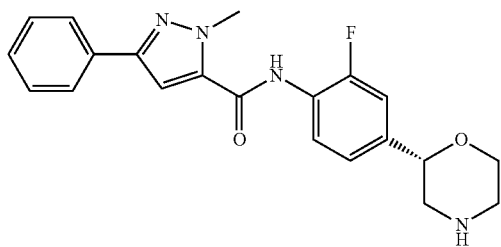 [SMILES: Cn1nc(-c2ccccc2)cc1C(=O)Nc1ccc([C@H]2CNCCO2)cc1F]

The title compound was obtained in analogy to example 1 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 1-methyl-3-phenyl-1H-pyrazole-5-carboxylic acid (CAS 10250-64-3) in place of 6-fluoro-1H-indazole-3-carboxylic acid in step (i). White solid. MS (ISP): 381.3 ([M+H]$^+$).

Example 18

(RS)—N-(2-Chloro-4-(morpholin-2-yl)phenyl)-1-(4-fluorophenyl)-1H-pyrazole-4-carboxamide

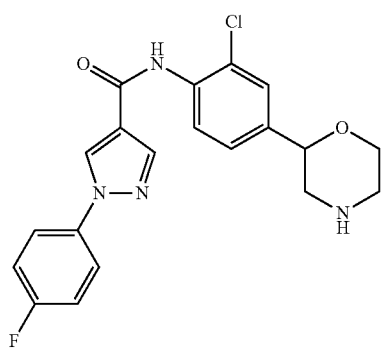 [SMILES: O=C(Nc1ccc(C2CNCCO2)cc1Cl)c1cnn(-c2ccc(F)cc2)c1]

a) tert-Butyl (RS)-2-(3-chloro-4-(1-(4-fluorophenyl)-1H-pyrazole-4-carboxamido)phenyl)morpholine-4-carboxylate To a stirred suspension of 1-(4-fluorophenyl)-1H-pyrazole-4-carboxylic acid (69 mg, CAS 138907-81-0) in dichloroethane (2 ml) were added oxalyl chloride (67 μl) and DMF (2 drops). The reaction mixture was stirred at room temperature for 1 h and was then concentrated in vacuo. The residue was dissolved in THF (1 ml) and the resulting solution was added dropwise to a stirred solution of tert-butyl (RS)-2-(4-amino-3-chlorophenyl)morpholine-4-carboxylate (80 mg, example 5 g) and triethylamine (178 μl) in THF (2 ml). The reaction mixture was stirred at room temperature for 2 h. The crude reaction mixture was then concentrated in vacuo and the residue was purified by column chromatography (SiO$_2$; gradient: 0% to 50% EtOAc in heptane) to give tert-butyl (RS)-2-(3-chloro-4-(1-(4-fluorophenyl)-1H-pyrazole-4-carboxamido)phenyl)morpholine-4-carboxylate (102 mg, 80%) as a white solid. MS (ISP): 520.3 ([{$^{37}$Cl}M+NH$_4$]$^+$), 518.2 ([{$^{35}$Cl}M+NH$_4$]$^+$), 503.1 ([{$^{37}$Cl}M+H]$^+$), 501.1 ([{$^{35}$Cl}M+H]$^+$), 447.1 ([{$^{37}$Cl}M+H—C$_4$H$_8$]$^+$), 445.1 ([{$^{35}$Cl}M+H—C$_4$H$_8$]$^+$).

b) (RS)—N-(2-Chloro-4-(morpholin-2-yl)phenyl)-1-(4-fluorophenyl)-1H-pyrazole-4-carboxamide To a stirred solution of trifluoroacetic acid (200 μl) in water (4.5 ml) was added a solution of tert-butyl (RS)-2-(3-chloro-4-(1-(4-fluorophenyl)-1H-pyrazole-4-carboxamido)phenyl)morpholine-4-carboxylate (100 mg) in acetonitrile (3 ml). The reaction mixture was then capped and the mixture was shaken at 80° C. for 5 h. The reaction mixture was then cooled to room temperature and poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: MeOH/EtOAc/heptane) to afford (RS)—N-(2-chloro-4-(morpholin-2-yl)phenyl)-1-(4-fluorophenyl)-1H-pyrazole-4-carboxamide (77 mg, 96%) as a white solid. MS (ISP): 403.1 ([{$^{37}$Cl}M+H]$^+$), 401.0 ([{$^{35}$Cl}M+H]$^+$).

Examples 19 & 20

(S)-1-(2-Chloro-4-morpholin-2-yl-phenyl)-3-(6-chloro-pyridin-3-yl)-urea & (R)-1-(2-Chloro-4-morpholin-2-yl-phenyl)-3-(6-chloro-pyridin-3-yl)-urea

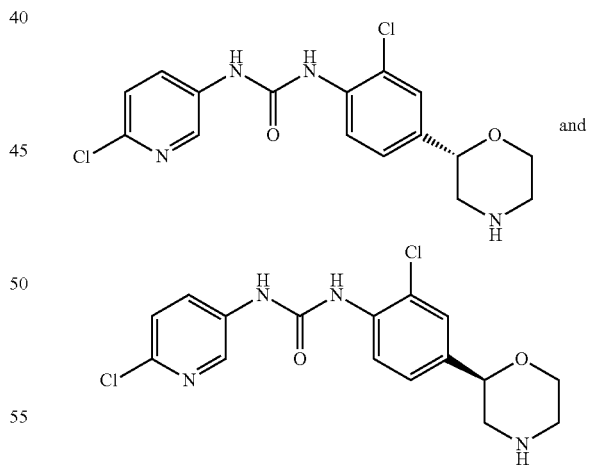

The enantiomers of (RS)-1-(2-chloro-4-morpholin-2-yl-phenyl)-3-(6-chloro-pyridin-3-yl)-urea (42 mg, Example 14) were separated using chiral HPLC (column: Chiralpak AD, 5×50 cm; eluent: 40% ethanol/heptane; pressure: 18 bar; flow rate: 35 ml/min) affording:

(+)-(S)-1-(2-Chloro-4-morpholin-2-yl-phenyl)-3-(6-chloro-pyridin-3-yl)-urea (14 mg, light yellow solid)

Retention time=21 min. MS (ISP): 371.1 ([{$^{37}$Cl}M+H]$^+$), 368.9 ([{$^{37}$Cl$^{35}$Cl}M+H]$^+$), 367.1 ([{$^{35}$Cl}M+H]$^+$).

(−)-(R)-1-(2-Chloro-4-morpholin-2-yl-phenyl)-3-(6-chloro-pyridin-3-yl)-urea (13 mg, white solid)

Retention time=30 min. MS (ISP): 371.1 ([{$^{37}$Cl}M+H]$^+$), 368.9 ([{$^{37}$Cl$^{35}$Cl}M+H]$^+$), 367.1 ([{$^{35}$Cl}M+H]$^+$).

Example 21

(R)—N-(2-fluoro-4-(morpholin-2-yl)phenyl)-1-(4-fluorophenyl)-1H-pyrazole-4-carboxamide

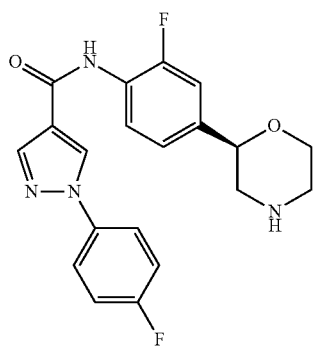 [SMILES: O=C(Nc1ccc([C@@H]2CNCCO2)cc1F)c1cnn(-c2ccc(F)cc2)c1]

The title compound was obtained in analogy to example 1 using 1-(4-fluorophenyl)-1H-pyrazole-4-carboxylic acid (CAS 138907-81-0) in place of 6-fluoro-1H-indazole-3-carboxylic acid in step (i). White solid. MS (ISP): 385.1 ([M+H]$^+$).

Example 22

(S)—N-(2-fluoro-4-(morpholin-2-yl)phenyl)-1-(4-fluorophenyl)-1H-pyrazole-4-carboxamide

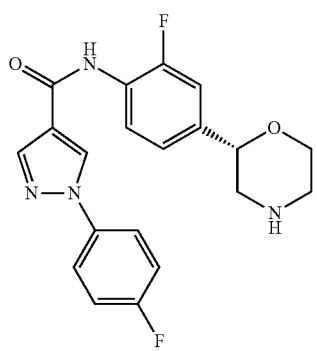 [SMILES: O=C(Nc1ccc([C@H]2CNCCO2)cc1F)c1cnn(-c2ccc(F)cc2)c1]

The title compound was obtained in analogy to example 1 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 1-(4-fluorophenyl)-1H-pyrazole-4-carboxylic acid (CAS 138907-81-0) in place of 6-fluoro-1H-indazole-3-carboxylic acid in step (i). White solid. MS (ISP): 385.1 ([M+H]$^+$).

Example 23

2-Methyl-5-phenyl-2H-pyrazole-3-carboxylic acid ((R)-2-fluoro-4-morpholin-2-yl-phenyl)-amide

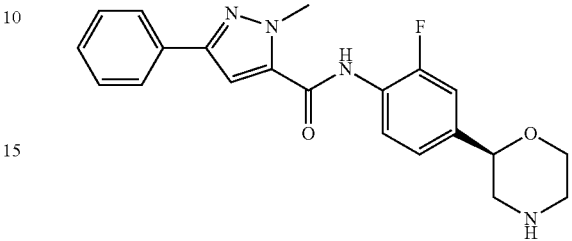

a) (R)-2-{3-Fluoro-4-[(2-methyl-5-phenyl-2H-pyrazole-3-carbonyl)-amino]-phenyl}-morpholine-4-carboxylic acid tert-butyl ester To a stirred suspension of 1-methyl-3-phenyl-1H-pyrazole-5-carboxylic acid (46 mg, CAS 10250-64-3) in dichloroethane (2 ml) were added oxalyl chloride (44 µl) and DMF (2 drops). The reaction mixture was stirred at room temperature for 1 h and was then concentrated in vacuo. The residue was dissolved in THF (1 ml) and the resulting solution was added dropwise to a stirred solution of (+)-(R)-2-(4-amino-3-fluoro-phenyl)-morpholine-4-carboxylic acid tert-butyl ester (50 mg, example 1 h) and triethylamine (118 µl) in THF (2 ml). The reaction mixture was stirred at room temperature for 2 h. The crude reaction mixture was then concentrated in vacuo and the residue was purified by column chromatography (SiO$_2$; gradient: 0% to 50% EtOAc in heptane) to give (R)-2-{3-fluoro-4-[(2-methyl-5-phenyl-2H-pyrazole-3 carbonyl)-amino]-phenyl}-morpholine-4-carboxylic acid tert-butyl ester (81 mg, quant.) as a white solid. MS (ISP): 503.1 ([M+Na]$^+$), 481.3 ([M+H]$^+$), 425.2 ([M+H—C$_4$H$_8$]$^+$).

b) 2-Methyl-5-phenyl-2H-pyrazole-3-carboxylic acid ((R)-2-fluoro-4-morpholin-2-yl-phenyl)-amide To a stirred solution of trifluoroacetic acid (124 µl) in water (4 ml) was added a solution of (R)-2-{3-fluoro-4-[(2-methyl-5-phenyl-2H-pyrazole-3-carbonyl)-amino]-phenyl}-morpholine-4-carboxylic acid tert-butyl ester (78 mg) in acetonitrile (2 ml). The reaction mixture was then capped and the mixture was shaken at 80° C. for 4 h. The reaction mixture was then cooled to room temperature and poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: EtOAc/heptane) to afford 2-methyl-5-phenyl-2H-pyrazole-3-carboxylic acid ((R)-2-fluoro-4-morpholin-2-yl-phenyl)-amide (49 mg, 79%) as a white solid. MS (ISP): 381.3 ([M+H]$^+$).

Example 24

2-Chloro-N—((R)-2-fluoro-4-morpholin-2-yl-phenyl)-6-methoxy-isonicotinamide

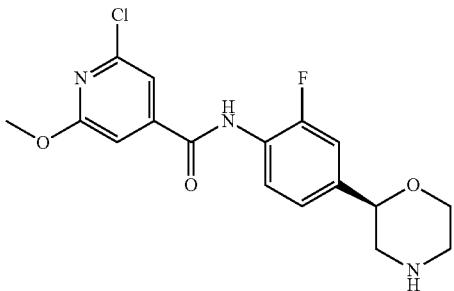 [SMILES: COc1cc(C(=O)Nc2ccc([C@@H]3CNCCO3)cc2F)cc(Cl)n1]

The title compound was obtained in analogy to example 23 using 2-chloro-6-methoxyisonicotinic acid (CAS 15855-06-8) in place of 1-methyl-3-phenyl-1H-pyrazole-5-carboxylic acid in step (a). White solid. MS (ISP): 368.1 ([$\{^{37}Cl\}$M+H]$^+$), 366.2 ([$\{^{35}Cl\}$M+H]$^+$).

Example 25

2-Chloro-N—((S)-2-fluoro-4-morpholin-2-yl-phenyl)-6-methoxy-isonicotinamide

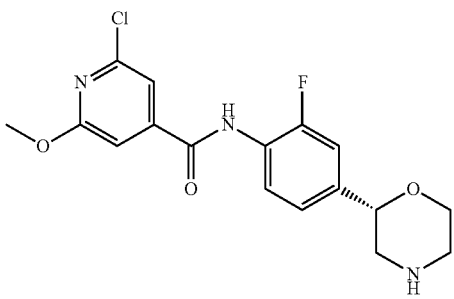 [SMILES: COc1cc(C(=O)Nc2ccc([C@H]3CNCCO3)cc2F)cc(Cl)n1]

The title compound was obtained in analogy to example 23 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 2-chloro-6-methoxyisonicotinic acid (CAS 15855-06-8) in place of 1-methyl-3-phenyl-1H-pyrazole-5-carboxylic acid in step (a). White solid. MS (ISP): 368.1 ([$\{^{37}Cl\}$M+H]$^+$), 366.1 ([$\{^{35}Cl\}$M+H]$^+$).

Example 26

1-(3-Cyano-5-fluoro-phenyl)-3-((S)-2-fluoro-4-morpholin-2-yl-phenyl)-urea

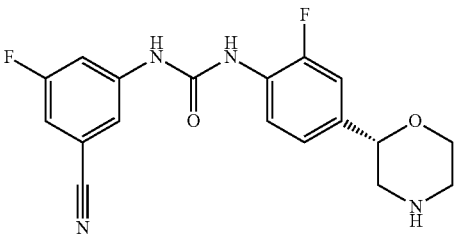 [SMILES: N#Cc1cc(F)cc(NC(=O)Nc2ccc([C@H]3CNCCO3)cc2F)c1]

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 5-amino-3-fluorobenzonitrile (CAS 210992-28-2) in place of 3-aminobenzonitrile in step (a). Off-white solid. MS (ISP): 359.2 ([M+H]$^+$).

Example 27

1-(3-Cyano-4-fluoro-phenyl)-3-((S)-2-fluoro-4-morpholin-2-yl-phenyl)-urea

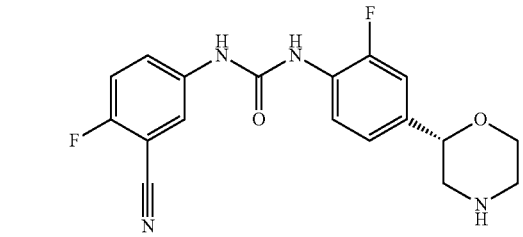 [SMILES: N#Cc1cc(NC(=O)Nc2ccc([C@H]3CNCCO3)cc2F)ccc1F]

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 5-amino-2-fluorobenzonitrile (CAS 53312-81-5) in place of 3-aminobenzonitrile in step (a). White solid. MS (ISP): 359.2 ([M+H]$^+$).

Example 28

(RS)—N-(2-Cyano-4-(morpholin-2-yl)phenyl)-1-(4-fluorophenyl)-1H-pyrazole-3-carboxamide

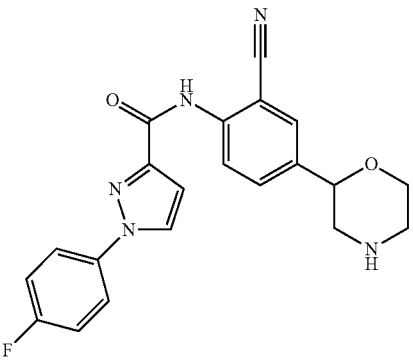 [SMILES: N#Cc1cc(C2CNCCO2)ccc1NC(=O)c1ccn(-c2ccc(F)cc2)n1]

a) tert-Butyl (RS)-2-(4-amino-3-bromophenyl)morpholine-4-carboxylate

To a stirred solution of tert-butyl (RS)-2-(4-aminophenyl)morpholine-4-carboxylate (3.07 g, CAS-1002726-96-6) in DMF (30 ml) was added NBS (1.96 g) and the mixture was stirred at room temperature for 15 min. The reaction mixture was then poured into EtOAc and extracted sequentially with water and with saturated brine. The organic layer was dried over Na$_2$SO$_4$ and then concentrated in vacuo to afford tert-butyl (RS)-2-(4-amino-3-bromophenyl)morpholine-4-carboxylate (4.0 g, quant.) as a light brown solid which was used in the next step without further purification. MS (ISP): 359.0 ([$\{^{81}Br\}$M+H]$^+$), 357.0 ([$\{^{79}Br\}$M+H]$^+$), 303.0 ([$\{^{81}Br\}$M+H—C$_4$H$_8$]$^+$), 301.0 ([$\{^{79}Br\}$M+H—C$_4$H$_8$]$^+$).

b) tert-Butyl (RS)-2-(4-amino-3-cyanophenyl)morpholine-4-carboxylate

To a stirred solution of tert-butyl (RS)-2-(4-amino-3-bromophenyl)morpholine-4-carboxylate (3.76 g) in NMP (30 ml) was added CuCN (1.77 g) and the reaction mixture was then stirred at 160° C. for 5 h. The mixture was then cooled to room temperature and poured into EtOAc. The resulting suspension was filtered through sintered glass and the filtrate was extracted sequentially with water and with saturated brine. The organic layer was dried over $Na_2SO_4$ and concentrated in vacuo. The residue was purified by flash column chromatography (silica gel; gradient: 0% to 60% EtOAc in heptane) to afford tert-butyl (RS)-2-(4-amino-3-cyanophenyl)morpholine-4-carboxylate (659 mg, 21%) as a yellow solid. MS (ISP): 321.2 ($[M+NH_4]^+$), 304.2 ($[M+H]^+$).

c) tert-Butyl (RS)-2-(3-cyano-4-(1-(4-fluorophenyl)-1H-pyrazole-3-carboxamido)phenyl)morpholine-4-carboxylate To a stirred suspension of 1-(4-fluorophenyl)-1H-pyrazole-3-carboxylic acid (52 mg, CAS 1152535-34-6) in dichloroethane (2 ml) were added oxalyl chloride (61 µl) and DMF (2 drops). The reaction mixture was stirred at room temperature for 1 h and was then concentrated in vacuo. The residue was dissolved in THF (1 ml) and the resulting solution was added dropwise to a stirred solution of tert-butyl (RS)-2-(4-amino-3-cyanophenyl)morpholine-4-carboxylate (70 mg) and triethylamine (161 µl) in THF (2 ml). The reaction mixture was stirred at room temperature for 2 h. The crude reaction mixture was then concentrated in vacuo and the residue was purified by column chromatography ($SiO_2$; gradient: 0% to 50% EtOAc in heptane) to give tert-butyl (RS)-2-(3-cyano-4-(1-(4-fluorophenyl)-1H-pyrazole-3-carboxamido)phenyl)morpholine-4-carboxylate (49 mg, 43%) as a white solid. MS (ISP): 514.2 ($[M+Na]^+$), 509.2 ($[M+NH_4]^+$), 492.2 ($[M+H]^+$), 436.2 ($[M+H—C_4H_8]^+$).

d) (RS)—N-(2-Cyano-4-(morpholin-2-yl)phenyl)-1-(4-fluorophenyl)-1H-pyrazole-3-carboxamide To a stirred solution of trifluoroacetic acid (84 µl) in water (4.5 ml) was added a solution of tert-butyl (RS)-2-(3-cyano-4-(1-(4-fluorophenyl)-1H-pyrazole-3-carboxamido)phenyl)morpholine-4-carboxylate (41 mg) in acetonitrile (2 ml). The reaction mixture was then capped and the mixture was shaken at 80° C. for 5 h. The reaction mixture was then cooled to room temperature and poured into 1 M aq. NaOH and the resulting mixture was extracted twice with EtOAc. The organic layers were dried over Na2SO4 and concentrated in vacuo. The crude material was purified by flash column chromatography ($SiO_2$; gradient: 0% to 10% methanol in dichloromethane) to afford (RS)—N-(2-cyano-4-(morpholin-2-yl)phenyl)-1-(4-fluorophenyl)-1H-pyrazole-3-carboxamide (20 mg, 61%) as a white solid. MS (ISP): 392.2 ($[M+H]^+$).

Example 29

S)—N-(2-Chloro-4-(morpholin-2-yl

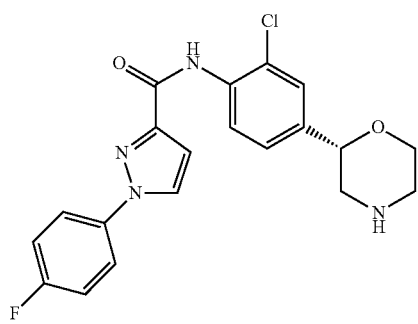 [SMILES: O=C(Nc1ccc([C@H]2CNCCO2)cc1Cl)c1ccn(-c2ccc(F)cc2)n1]

a) (+)-tert-Butyl (R)-2-(4-amino-3-chlorophenyl)morpholine-4-carboxylate & (−)-tert-Butyl (S)-2-(4-amino-3-chlorophenyl)morpholine-4-carboxylate The enantiomers of tert-butyl (RS)-2-(4-amino-3-chlorophenyl)morpholine-4-carboxylate (2.00 g, example 5 g) were separated using chiral HPLC (column: Chiralpak AD, 5×50 cm; eluent: 10% isopropanol/heptane; pressure: 18 bar; flow rate: 35 ml/min) affording:

(+)-tert-Butyl (R)-2-(4-amino-3-chlorophenyl)morpholine-4-carboxylate (894 mg, white solid)

Retention time=60 min. MS (ISP): 337.2 ($[\{^{37}Cl\}M+Na]^+$), 335.1 ($[\{^{35}Cl\}M+Na]^+$), 315.0 ($[\{^{37}Cl\}M+H]^+$), 313.0 ($[\{^{35}Cl\}M+H]^+$), 259.2 ($[\{^{37}Cl\}M+H—C_4H_8]^+$), 257.1 ($[\{^{35}Cl\}M+H—C_4H_8]^+$).

(−)-tert-Butyl (S)-2-(4-amino-3-chlorophenyl)morpholine-4-carboxylate (934 mg, white solid)

Retention time=76 min. MS (ISP): 337.1 ($[\{^{37}Cl\}M+Na]^+$), 335.0 ($[\{^{35}Cl\}M+Na]^+$), 314.7 ($[\{^{37}Cl\}M+H]^+$), 313.0 ($[\{^{35}Cl\}M+H]^+$), 259.0 ($[\{^{37}Cl\}M+H—C_4H_8]^+$), 257.0 ($[\{^{35}Cl\}M+H—C_4H_8]^+$).

b) (S)—N-(2-Chloro-4-(morpholin-2-yl)phenyl)-1-(4-fluorophenyl)-1H-pyrazole-3-carboxamide The title compound was obtained in analogy to example 18 using (−)-tert-butyl (S)-2-(4-amino-3-chlorophenyl)morpholine-4-carboxylate in place of tert-butyl (RS)-2-(4-amino-3-chlorophenyl)morpholine-4-carboxylate and 1-(4-fluorophenyl)-1H-pyrazole-3-carboxylic acid (CAS 1152535-34-6) in place of 1-(4-fluorophenyl)-1H-pyrazole-4-carboxylic acid in step (a). White solid. MS (ISP): 403.1 ($[\{^{37}Cl\}M+H]^+$), 401.1 ($[\{^{35}Cl\}M+H]^+$).

Example 30

(R)—N-(2-Chloro-4-(morpholin-2-yl)phenyl)-1-(4-fluorophenyl)-1H-pyrazole-3-carboxamide

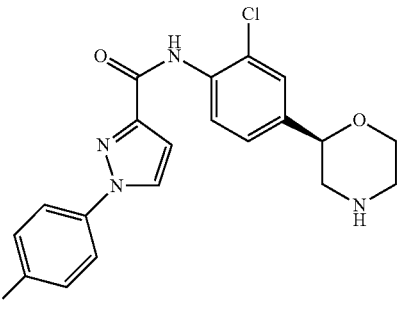

The title compound was obtained in analogy to example 18 using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 1-(4-fluorophenyl)-1H-pyrazole-3-carboxylic acid (CAS 1152535-34-6) in place of 1-(4-fluorophenyl)-1H-pyrazole-4-carboxylic acid in step (a). White solid. MS (ISP): 403.1 ($[\{^{37}Cl\}M+H]^+$), 401.1 ($[\{^{35}Cl\}M+H]^+$).

Example 31

(S)—N-(2-Chloro-4-(morpholin-2-yl)phenyl)-1-(4-fluorophenyl)-1H-pyrazole-4-carboxamide

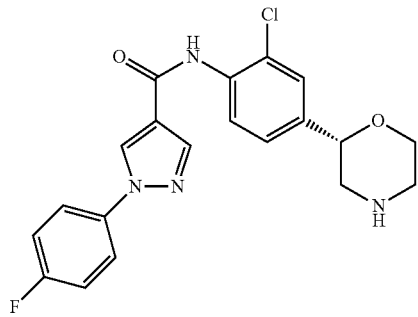 [SMILES: O=C(Nc1ccc([C@H]2CNCCO2)cc1Cl)c1cnn(-c2ccc(F)cc2)c1]

The title compound was obtained in analogy to example 18 using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate in step (a). White solid. MS (ISP): 403.1 ([{$^{37}$Cl}M+H]$^+$), 401.1 ([{$^{35}$Cl}M+H]$^+$).

Example 32

(R)—N-(2-Chloro-4-(morpholin-2-yl)phenyl)-1-(4-fluorophenyl)-1H-pyrazole-4-carboxamide

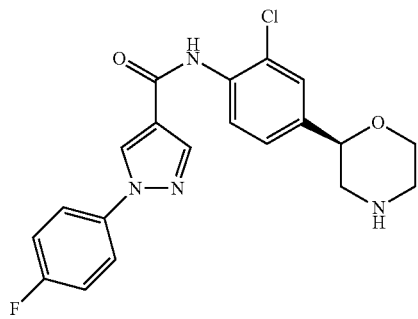 [SMILES: O=C(Nc1ccc([C@@H]2CNCCO2)cc1Cl)c1cnn(-c2ccc(F)cc2)c1]

The title compound was obtained in analogy to example 18 using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate in step (a). White solid. MS (ISP): 403.1 ([{$^{37}$Cl}M+H]$^+$), 401.1 ([{$^{35}$Cl}M+H]$^+$).

Example 33

(RS)-1-(2-Cyano-4-morpholin-2-yl-phenyl)-3-(3-cyano-phenyl)-urea

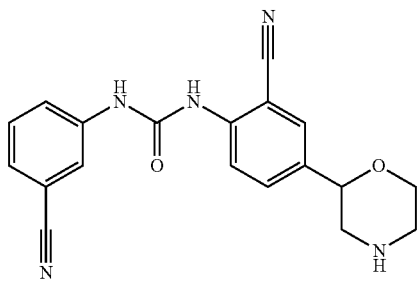 [SMILES: N#Cc1cccc(NC(=O)Nc2ccc(C3CNCCO3)cc2C#N)c1]

a) (RS)-2-{3-Cyano-4-[3-(3-cyano-phenyl)-ureido]-phenyl}-morpholine-4-carboxylic acid tert-butyl ester To a stirred solution of tert-butyl (RS)-2-(4-amino-3-cyanophenyl)morpholine-4-carboxylate (70 mg, example 28b) in dichloromethane (2 ml) was added triphosgene (25 mg). A solution of sodium carbonate (49 mg) in water (2 ml) was then added. The reaction mixture was stirred at room temperature for 3 hours. TLC showed all the starting material had reacted. 3-Aminobenzonitrile (28 mg, CAS 2237-30-1) was then added and the reaction mixture was stirred at room temperature for a further 40 hours. TLC showed the reaction was complete. The reaction mixture was poured into dichloromethane and extracted with water. The organic phase was separated, dried over sodium sulphate and concentrated in vacuo. The residue was purified by column chromatography (SiO$_2$; gradient: 0% to 100% EtOAc in hexanes) to give (RS)-2-{3-cyano-4-[3-(3-cyano-phenyl)-ureido]-phenyl}-morpholine-4-carboxylic acid tert-butyl ester (16 mg, 16%) as a white solid. MS (ISP): 392.2 ([M+H—C$_4$H$_8$]$^+$), 348.2 ([M+H—C$_4$H$_8$—CO$_2$]$^+$).

b) (RS)-1-(2-Cyano-4-morpholin-2-yl-phenyl)-3-(3-cyano-phenyl)-urea

To a stirred solution of trifluoroacetic acid (22 μl) in water (3 ml) was added a solution of (RS)-2-{3-cyano-4-[3-(3-cyano-phenyl)-ureido]-phenyl}-morpholine-4-carboxylic acid tert-butyl ester (13 mg) in acetonitrile (1.5 ml). The reaction mixture was then capped and the mixture was shaken at 80° C. for 4 h. The reaction mixture was then cooled to room temperature and poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: heptane/EtOAc/MeOH to afford (RS)-1-(2-cyano-4-morpholin-2-yl-phenyl)-3-(3-cyano-phenyl)-urea (6 mg, 52%) as a light brown solid. MS (ISP): 348.1 ([M+H]$^+$).

Example 34

(S)-4-Chloro-N-(2-chloro-4-(morpholin-2-yl)phenyl)benzamide

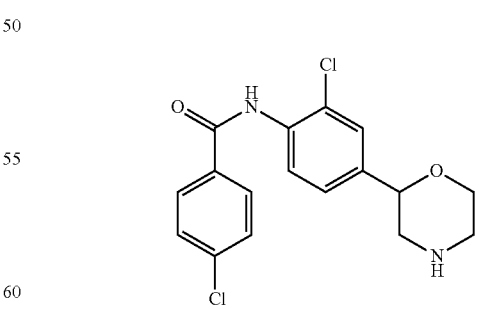

The title compound was obtained in analogy to example 18 using 4-chloro-benzoic acid (CAS 74-11-3) in place of 1-(4-fluorophenyl)-1H-pyrazole-4-carboxylic acid in step (a). White solid. MS (ISP): 355.2 ([{$^{37}$Cl}M+H]$^+$), 353.1 ([{$^{37}$Cl$^{35}$Cl}M+H]$^+$), 351.2 ([{$^{35}$Cl}M+H]$^+$).

Example 35

(R)-6-Chloro-N-(2-chloro-4-(morpholin-2-yl)phenyl)nicotinamide

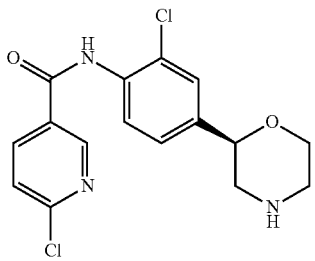 [SMILES: O=C(Nc1ccc([C@@H]2CNCCO2)cc1Cl)c1ccc(Cl)nc1]

The title compound was obtained in analogy to example 18 using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 6-chloronicotinic acid (CAS 5326-23-8) in place of 1-(4-fluorophenyl)-1H-pyrazole-4-carboxylic acid in step (a). White solid. MS (ISP): 356.2 ([$\{^{37}Cl\}M+H]^+$), 354.1 ([$\{^{37}Cl^{35}Cl\}M+H]^+$), 352.2 ([$\{^{35}Cl\}M+H]^+$).

Example 36

(S)-6-Chloro-N-(2-chloro-4-(morpholin-2-yl)phenyl)nicotinamide

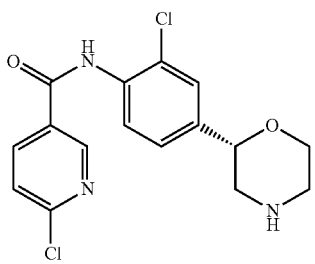 [SMILES: O=C(Nc1ccc([C@H]2CNCCO2)cc1Cl)c1ccc(Cl)nc1]

The title compound was obtained in analogy to example 18 using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 6-chloronicotinic acid (CAS 5326-23-8) in place of 1-(4-fluorophenyl)-1H-pyrazole-4-carboxylic acid in step (a). Light yellow solid. MS (ISP): 356.2 ([$\{^{37}Cl\}M+H]^+$), 354.1 ([$\{^{37}Cl^{35}Cl\}M+H]^+$), 352.2 ([$\{^{35}Cl\}M+H]^+$).

Example 37

(RS)-1-(2-Bromo-4-(morpholin-2-yl)phenyl)-3-(6-chloropyridin-3-yl)urea

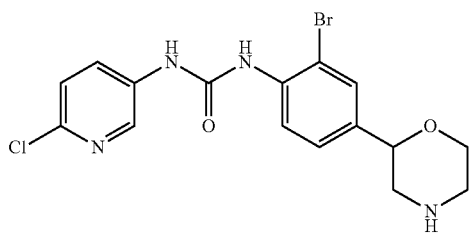

a) (RS)-2-{3-Bromo-4-[3-(6-chloro-pyridin-3-yl)-ureido]-phenyl}-morpholine-4-carboxylic acid tert-butyl ester To a stirred solution of tert-butyl (RS)-2-(4-amino-3-bromophenyl)morpholine-4-carboxylate (100 mg, example 28a) in dichloromethane (2 ml) was added triphosgene (31 mg). A solution of sodium carbonate (59 mg) in water (2 ml) was then added. The reaction mixture was stirred at room temperature for 2.5 hours. TLC showed all the starting material had reacted. A solution of 6-chloropyridin-3-amine (36 mg, CAS 5350-93-6) in dichloromethane (2 ml) was then added and the reaction mixture was stirred at room temperature for a further 2 hours. TLC showed the reaction was complete. The reaction mixture was poured into dichloromethane and extracted with water. The organic phase was separated, dried over sodium sulphate and concentrated in vacuo. The residue was purified by column chromatography (SiO$_2$; gradient: 0% to 80% EtOAc in heptanes) to give (RS)-2-{3-bromo-4-[3-(6-chloro-pyridin-3-yl)-ureido]-phenyl}-morpholine-4-carboxylic acid tert-butyl ester (47 mg, 33%) as an off-white solid. MS (ISP): 515.2 ([$\{^{37}Cl^{81}Br\}M+H]^+$), 513.2 ([$\{^{37}Cl^{79}Br$ or $^{35}Cl^{81}Br\}M+H]^+$), 511.0 ([$\{^{35}Cl^{79}Br\}M+H]^+$), 459.0 ([$\{^{37}Cl^{81}Br\}M+H-C_4H_8]^+$), 457.0 ([$\{^{37}Cl^{79}Br$ or $^{35}Cl^{81}Br\}M+H-C_4H_8]^+$), 454.9 ([$\{^{35}Cl^{79}Br\}M+H-C_4H_8]^+$).

b) (RS)-1-(2-Bromo-4-(morpholin-2-yl)phenyl)-3-(6-chloropyridin-3-yl)urea

To a stirred solution of trifluoroacetic acid (90 µl) in water (6 ml) was added a solution of (RS)-2-{3-bromo-4-[3-(6-chloro-pyridin-3-yl)-ureido]-phenyl}-morpholine-4-carboxylic acid tert-butyl ester (46 mg) in acetonitrile (2 ml). The reaction mixture was then capped and the mixture was shaken at 80° C. for 5 h. The reaction mixture was then cooled to room temperature and poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: heptane/EtOAc/MeOH) to afford (RS)-1-(2-bromo-4-(morpholin-2-yl)phenyl)-3-(6-chloropyridin-3-yl)urea (25 mg, 68%) as an off-white solid. MS (ISP): 415.0 ([$\{^{37}Cl^{81}Br\}M+H]^+$), 413.0 ([$\{^{37}Cl^{79}Br$ or $^{35}Cl^{81}Br\}M+H]^+$), 411.0 ([$\{^{35}Cl^{79}Br\}M+H]^+$).

Example 38

(RS)-1-(6-Chloro-pyridin-3-yl)-3-(2-chloro-4-pyrrolidin-3-yl-phenyl)-urea

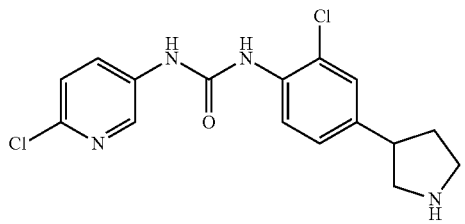 [SMILES: O=C(Nc1ccc(Cl)nc1)Nc1ccc(C2CCNC2)cc1Cl]

a) tert-Butyl (RS)-3-(4-amino-3-chlorophenyl)pyrrolidine-1-carboxylate

To a stirred solution of tert-butyl 3-(4-aminophenyl)pyrrolidine-1-carboxylate (2.00 g, CAS-908334-28-1) in DMF (15 ml) was added NCS (1.07 g) and the mixture was stirred at 70° C. for 1 hour. The reaction mixture was then cooled to room temperature and poured into EtOAc and extracted sequentially with water and with saturated brine. The organic layer was dried over Na$_2$SO$_4$ and then concentrated in vacuo. The residue was purified by column chromatography (SiO$_2$, gradient: 0% to 55% EtOAc in hexanes) to afford tert-butyl (RS)-3-(4-amino-3-chlorophenyl)pyrrolidine-1-carboxylate (1.16 g, 51%) as a yellow oil which was used in the next step without further purification. MS (ISP): 299.0 ([{$^{37}$Cl}M+H]$^+$), 297.2 ([{$^{35}$Cl}M+H]$^+$), 243.0 ([{$^{37}$Cl}M+H—C$_4$H$_8$]$^+$), 241.1 ([{$^{35}$Cl}M+H—C$_4$H$_8$]$^+$).

b) (RS)-3-{3-Chloro-4-[3-((6-chloro-pyridin-3-yl)-ureido]-phenyl}-pyrrolidine-1-carboxylic acid tert-butyl ester To a stirred solution of tert-butyl tert-butyl (RS)-3-(4-amino-3-chlorophenyl)pyrrolidine-1-carboxylate (70 mg) in dichloromethane (2 ml) was added triphosgene (26 mg). A solution of sodium carbonate (50 mg) in water (2 ml) was then added. The reaction mixture was stirred at room temperature for 1.5 hours. TLC showed all the starting material had reacted. 6-Chloropyridin-3-amine (31 mg, CAS 5350-93-6) was then added and the reaction mixture was stirred at room temperature for a further 20 hours. TLC showed the reaction was complete. The reaction mixture was poured into dichloromethane and extracted with water. The organic phase was separated, dried over sodium sulphate and concentrated in vacuo. The residue was purified by column chromatography (SiO$_2$; gradient: 0% to 100% EtOAc in heptanes) to give (RS)-3-{3-chloro-4-[3-(6-chloro-pyridin-3-yl)-ureido]-phenyl}-pyrrolidine-1-carboxylic acid tert-butyl ester (71 mg, 67%) as an off-white solid. MS (ISP): 399.2 ([{$^{37}$Cl}M+H—C$_4$H$_8$]$^+$), 397.2 ([{$^{37}$Cl$^{35}$Cl}M+H—C$_4$H$_8$]$^+$), 395.0 ([{$^{35}$Cl}M+H—C$_4$H$_8$]$^+$), 355.2 ([{$^{37}$Cl}M+H—C$_4$H$_8$—CO$_2$]$^+$), 353.2 ([{$^{37}$Cl$^{35}$Cl}M+H—C$_4$H$_8$—CO$_2$]$^+$), 351.2 ([{$^{35}$Cl}M+H—C$_4$H$_8$—CO$_2$]$^+$).

c) (RS)-1-(6-Chloro-pyridin-3-yl)-3-(2-chloro-4-pyrrolidin-3-yl-phenyl)-urea

To a stirred suspension of (RS)-3-{3-chloro-4-[3-(6-chloro-pyridin-3-yl)-ureido]-phenyl}-pyrrolidine-1-carboxylic acid tert-butyl ester (68 mg) in dichloromethane (6 ml) was added trifluoroacetic acid (92 µl) and the reaction mixture was then stirred at room temperature for 34 h. The reaction mixture was then poured into 1 M aq. NaOH and the resulting mixture was extracted twice with EtOAc. The organic layers were dried over Na$_2$SO$_4$ and concentrated in vacuo. The crude material was purified by flash column chromatography (Isolute® Flash-NH$_2$ from Separtis); gradient: heptane/EtOAc/MeOH) to afford (RS)-1-(6-chloro-pyridin-3-yl)-3-(2-chloro-4-pyrrolidin-3-yl-phenyl)-urea (9 mg, 17%) as an off-white solid. MS (ISP): 355.1 ([{$^{37}$Cl}M+H]$^+$), 353.1 ([{$^{37}$Cl$^{35}$Cl}M+H]$^+$), 351.2 ([{$^{35}$Cl}M+H]$^+$).

Example 39

(S)-1-(5-Cyano-2-methoxyphenyl)-3-(2-fluoro-4-(morpholin-2-yl)phenyl)urea hydrochloride

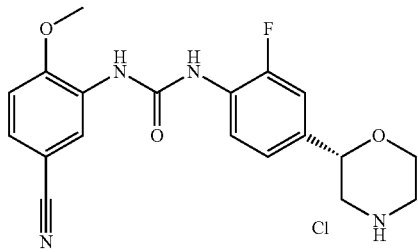 [SMILES: COc1ccc(C#N)cc1NC(=O)Nc1ccc([C@H]2CNCCO2)cc1F ; Cl]

a) (S)-2-{-4-[3-(5-Cyano-2-methoxy-phenyl)-ureido]-3-fluoro-phenyl}-morpholine-4-carboxylic acid tert-butyl ester In analogy to example 3, step a) using (−)-(S)-2-(4-amino-3-fluoro-phenyl)-morpholine-4-carboxylic acid tert-butyl ester (example 1 h) in place of (+)-(R)-2-(4-amino-3-fluoro-phenyl)-morpholine-4-carboxylic acid tert-butyl ester and 3-amino-4-methoxybenzonitrile (CAS 60979-25-1). MS (ISP): 415.1 ([M+H—C$_4$H$_8$]$^+$)

b) (S)-1-(5-Cyano-2-methoxyphenyl)-3-(2-fluoro-4-(morpholin-2-yl)phenyl)urea hydrochloride To a solution of (S)-2-{4-[3-(5-Cyano-2-methoxy-phenyl)-ureido]-3-fluoro-phenyl}-morpholine-4-carboxylic acid tert-butyl ester (97 mg, 106 µmol, Eq: 1.00) in THF (4 ml) was added 4M–HCl in dioxane (0.773 ml, 3.09 mmol, Eq: 15). The reaction mixture was stirred at 60° C. for 5 h. To the cooled mixture was then added ethyl acetate and the suspension was filtered off and dried under high vacuo to give the target compound as an off-white solid (63 mg, 75%). MS (ISP): 369.1 ([M+H]$^+$).

Example 40

(R)-1-(6-Chloropyridin-3-yl)-3-(2-methyl-4-(morpholin-2-yl)phenyl)urea

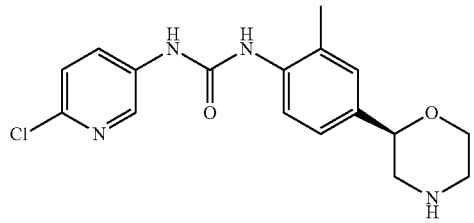 [SMILES: Cc1cc([C@@H]2CNCCO2)ccc1NC(=O)Nc1ccc(Cl)nc1]

a) 2-Bromo-1-(3-methyl-4-nitrophenyl)ethanone & 2-Chloro-1-(3-methyl-4-nitrophenyl)ethanone To a stirred solution of 3-methyl-4-nitrobenzoyl chloride (5.85 g, CAS 35675-46-8) in acetonitrile (70 ml) and THF (70 ml) at 0-5° C. was added dropwise (trimethylsilyl)diazomethane (16.5 ml, 2 M solution in hexane). The reaction mixture was stirred at room temperature for 1 hour. TLC analysis showed the reaction was complete. Hydrobromic acid (9.29 g) was then added dropwise at 0-5° C. and the reaction mixture was stirred at room temperature for 30 min. The reaction mixture was then poured into EtOAc and extracted sequentially with aq. Na$_2$CO$_3$ solution, water and saturated brine. The organic layer was then dried over Na$_2$SO$_4$ and concentrated in vacuo to afford a ca 1:1 mixture of 2-bromo-1-(3-methyl-4-nitrophenyl)ethanone and 2-chloro-1-(3-methyl-4-nitrophenyl)ethanone (6.23 g) as a brown solid which was used in the next step without further purification. MS (EI): 163.9 ([M$_1$-CH$_2$Cl]$^+$& [M$_2$-CH$_2$Br]$^+$).

b) (RS)-2-(3-Methyl-4-nitrophenyl)oxirane

To a stirred suspension of the mixture of 2-bromo-1-(3-methyl-4-nitrophenyl)ethanone and 2-chloro-1-(3-methyl-4-nitrophenyl)ethanone (6.23 g) in ethanol (100 ml) at 5° C. was added portionwise over 5 min NaBH₄ (913 mg). The reaction mixture was then stirred at room temperature for 1 hour to afford a dark yellow solution. TLC analysis showed the reaction was complete. Sodium methoxide (652 mg) was then added and the reaction mixture was stirred at room temperature overnight. TLC analysis showed a small amount of starting material remaining and so the reaction mixture was stirred at 40° C. for 1 h. The reaction mixture was then poured into EtOAc and extracted with saturated brine. The organic layer was dried over Na₂SO₄ and concentrated in vacuo to afford (RS)-2-(3-methyl-4-nitrophenyl)oxirane (4.63 g, 94% over 2 steps) as a yellow oil. MS (EI): 179 (M⁺), 164 ([M-CH₃]⁺), 162 [M-OH]⁺), 132 [M-OH—NO]⁺), 103, 77.

c) (RS)-2-(2-Hydroxyethylamino)-1-(3-methyl-4-nitrophenyl)ethanol

To a stirred solution of (RS)-2-(3-methyl-4-nitrophenyl)oxirane (4.63 g) in THF (15 ml) was added 2-aminoethanol (15.5 ml) and the mixture was stirred at room temperature overnight. The reaction mixture was then poured into EtOAc/THF (1:1) and extracted with saturated brine. The organic layer was dried over Na₂SO₄ and concentrated in vacuo to afford (RS)-2-(2-hydroxyethylamino)-1-(3-methyl-4-nitrophenyl)ethanol (6.84 g, quant.) as a brown oil which was used in the next step without further purification. MS (ISP): 241.1 ([M+H]⁺).

d) tert-Butyl (RS)-2-hydroxy-2-(3-methyl-4-nitrophenyl)ethyl(2-hydroxyethyl)carbamate To a stirred solution of (RS)-2-(2-hydroxyethylamino)-1-(3-methyl-4-nitrophenyl)ethanol (6.84 g) in THF (50 ml) was added Boc₂O (6.52 g) and the mixture was stirred at room temperature overnight. The reaction mixture was then concentrated in vacuo and the residue was purified by flash column chromatography (silica gel; gradient: heptane/CH₂Cl₂/MeOH) to afford tert-butyl (RS)-2-hydroxy-2-(3-methyl-4-nitrophenyl)ethyl(2-hydroxyethyl)carbamate (6.55 g, 74% over 2 steps) as a yellow oil. MS (ISP): 385.2 ([M+HCOO⁻]⁻).

e) tert-Butyl (RS)-2-(3-methyl-4-nitrophenyl)morpholine-4-carboxylate

To a stirred solution of tert-butyl (RS)-2-hydroxy-2-(3-methyl-4-nitrophenyl)ethyl(2-hydroxyethyl)carbamate (6.55 g) and triethylamine (3.22 ml) in THF (50 ml) at 0-5° C. was added dropwise methanesulfonyl chloride (1.65 ml). The reaction mixture was then stirred at room temperature for 30 min to afford a yellow suspension. TLC analysis showed a small amount of starting material remaining and so further aliquots of triethylamine (0.5 ml) and methanesulfonyl chloride (0.2 ml) were added. The reaction mixture was stirred at room temperature for a further 20 min and was then filtered to remove triethylamine hydrochloride, washing the filter with THF (20 ml). The filtrate was cooled to 0-5° C. and potassium 2-methyl-2-butoxide (17.0 ml, 1.7 M solution in toluene) was added. The reaction mixture was stirred at room temperature for 30 min and then poured into EtOAc and extracted sequentially with water and with saturated brine. The organic layer was dried over Na₂SO₄ and concentrated in vacuo. The residue was purified by flash column chromatography (silica gel; gradient: 0% to 70% EtOAc in hexanes) to afford tert-butyl (RS)-2-(3-methyl-4-nitrophenyl)morpholine-4-carboxylate (2.21 g, 36%) as a yellow oil. MS (ISP): 223.1 ([M+H—O₅H₈O₂]⁺).

f) tert-Butyl (RS)-2-(4-amino-3-methylphenyl)morpholine-4-carboxylate

To a stirred solution of tert-butyl (RS)-2-(3-methyl-4-nitrophenyl)morpholine-4-carboxylate (2.21 g) in methanol (100 ml) was added ammonium formate (6.48 g). The reaction mixture was degassed by bubbling argon into the mixture for several minutes. 10% Palladium on activated charcoal (219 mg) was then added and the reaction mixture was stirred at 60° C. for 1 hour. The reaction mixture was then filtered through celite and concentrated in vacuo. The residue was taken up in EtOAc and extracted sequentially with water and with saturated brine. The organic layer was dried over Na₂SO₄ and concentrated in vacuo to afford tert-butyl (RS)-2-(4-amino-3-methylphenyl)morpholine-4-carboxylate (1.99 g, 99%) as a colourless oil. MS (EI): 292 (M⁺), 235 ([M-C₄H₉]⁺), 219 ([M-C₄H₉O]⁺), 191, 136, 57 ([C₄H₉]⁺).

g) tert-Butyl (R)-2-(4-amino-3-methylphenyl)morpholine-4-carboxylate & tert-Butyl (S)-2-(4-amino-3-methylphenyl)morpholine-4-carboxylate The enantiomers of tert-butyl (RS)-2-(4-amino-3-methylphenyl)morpholine-4-carboxylate (1.18 g) were separated using chiral HPLC (column: Chiralpak AD, 5×50 cm; eluent: 5% isopropanol/heptane; pressure: 18 bar; flow rate: 35 ml/min) affording: (+)-(R)-tert-Butyl 2-(4-amino-3-methylphenyl)morpholine-4-carboxylate (453 mg, yellow oil) Retention time=120 min (−)-(S)-tert-Butyl 2-(4-amino-3-methylphenyl)morpholine-4-carboxylate (464 mg, yellow oil) Retention time=152 min.

h) (R)-tert-Butyl 2-(4-(3-(6-chloropyridin-3-yl)ureido)-3-methylphenyl)morpholine-4-carboxylate To a stirred solution of (+)-(R)-tert-butyl 2-(4-amino-3-methylphenyl)morpholine-4-carboxylate (99 mg) in dichloromethane (3 ml) was added a solution of sodium carbonate (72 mg) in water (3 ml). The reaction mixture was cooled to 0° C. and triphosgene (37 mg) was added. The reaction mixture was then stirred at 0° C. for 1 hour. TLC showed all the starting material had reacted. 6-Chloropyridin-3-amine (48 mg, CAS 5350-93-6) was then added and the reaction mixture was stirred at room temperature for a further hour. TLC showed the reaction was complete. The reaction mixture was poured into dichloromethane and extracted with water. The organic phase was separated, dried over sodium sulphate and concentrated in vacuo. The residue was purified by column chromatography (SiO₂; gradient: 0% to 70% EtOAc in hexanes) to give (R)-tert-butyl 2-(4-(3-(6-chloropyridin-3-yl)ureido)-3-methylphenyl)morpholine-4-carboxylate (106 mg, 70%) as an off-white solid. MS (ISP): 449.2 ([{³⁷Cl}M+H]⁺), 447.2 ([{³⁵Cl}M+H]⁺).

i) (R)-1-(6-Chloropyridin-3-yl)-3-(2-methyl-4-(morpholin-2-yl)phenyl)urea

To a stirred solution of trifluoroacetic acid (233 μl) in water (6 ml) was added a solution of (R)-tert-butyl 2-(4-(3-(6-chloropyridin-3-yl)ureido)-3-methylphenyl)morpholine-4-carboxylate (104 mg) in acetonitrile (2 ml). The reaction mixture was then capped and the mixture was shaken at 80° C. for 4 h. The reaction mixture was then cooled to room temperature and poured into 1 M aq. NaOH and the resulting mixture was extracted twice with EtOAc. The organic layers were dried over Na₂SO₄ and concentrated in vacuo. The crude material was purified by flash column chromatography (Isolute®

Flash-NH2 from Separtis); gradient: heptane/EtOAc/MeOH) to afford (R)-1-(6-chloropyridin-3-yl)-3-(2-methyl-4-(morpholin-2-yl)phenyl)urea (41 mg, 51%) as a white solid. MS (ISP): 349.1 ([{$^{37}$Cl}M+H]$^+$), 347.1 ([{$^{35}$Cl}M+H]$^+$).

Example 41

(RS)-1-(2-Chloro-4-(piperidin-3-yl)phenyl)-3-((6-chloropyridin-3-yl)urea

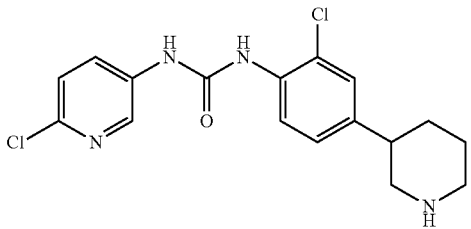 [SMILES: O=C(Nc1ccc(Cl)nc1)Nc1ccc(C2CCCNC2)cc1Cl]

The title compound was obtained in analogy to example 38 using tert-butyl 3-(4-aminophenyl)-piperidine-1-carboxylate (CAS 875798-79-1) in place of tert-butyl 3-(4-aminophenyl)pyrrolidine-1-carboxylate in step (a). White solid. MS (ISP): 369.1 ([{$^{37}$Cl}M+H]$^+$), 367.1 ([{$^{37}$Cl$^{35}$Cl}M+H]$^+$), 365.1 ([{$^{35}$Cl}M+H]$^+$).

Example 42

6-Chloro-N—((R)-2-methyl-4-morpholin-2-yl-phenyl)-nicotinamide

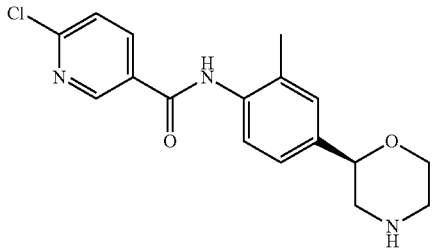 [SMILES: Cc1cc([C@@H]2CNCCO2)ccc1NC(=O)c1ccc(Cl)nc1]

The title compound was obtained in analogy to example 23 using (+)-(R)-tert-butyl 2-(4-amino-3-methylphenyl)morpholine-4-carboxylate (example 40(g)) in place of (+)-(R)-2-(4-amino-3-fluoro-phenyl)-morpholine-4-carboxylic acid tert-butyl ester and 6-chloro-nicotinic acid (CAS 5326-23-8) in place of 1-methyl-3-phenyl-1H-pyrazole-5-carboxylic acid in step (a). White solid. MS (ISP): 334.1 ([{$^{37}$Cl}M+H]$^+$), 332.1 ([{$^{35}$Cl}M+H]$^+$).

Example 43

(RS)-6-Chloro-N-(2-chloro-4-piperidin-3-yl-phenyl)-nicotinamide

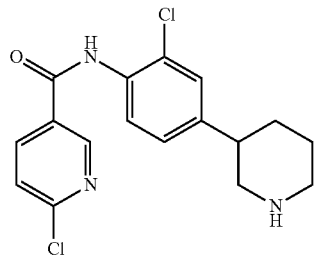 [SMILES: O=C(Nc1ccc(C2CCCNC2)cc1Cl)c1ccc(Cl)nc1]

a) tert-Butyl (RS)-3-(4-Amino-3-chloro-phenyl)-piperidine-1-carboxylate

The title compound was obtained in analogy to example 38 step (a) using tert-butyl 3-(4-aminophenyl)-piperidine-1-carboxylate (CAS 875798-79-1) in place of tert-butyl 3-(4-aminophenyl)pyrrolidine-1-carboxylate. Yellow solid. MS (ISP): 313.2 ([{$^{37}$Cl}M+H]$^+$), 311.2 ([{$^{35}$Cl}M+H]$^+$), 257.1 ([{$^{37}$Cl}M+H—C$_4$H$_8$]$^+$), 255.2 ([{$^{35}$Cl}M+H—C$_4$H$_8$]$^+$).

b) (RS)-6-Chloro-N-(2-chloro-4-piperidin-3-yl-phenyl)-nicotinamide

The title compound was obtained in analogy to example 18 using 6-chloro-nicotinic acid (CAS 5326-23-8) in place of 1-(4-fluorophenyl)-1H-pyrazole-4-carboxylic acid and tert-butyl (RS)-3-(4-amino-3-chlorophenyl)-piperidine-1-carboxylate in place of tert-butyl (RS)-2-(4-amino-3-chlorophenyl)morpholine-4-carboxylate in step (a). Off-white solid. MS (ISP): 354.3 ([{$^{37}$Cl}M+H]$^+$), 352.2 ([{$^{37}$Cl$^{35}$Cl}M+H]$^+$), 350.2 ([{$^{35}$Cl}M+H]$^+$).

Example 44

(R)-1-(5-Cyano-2-methoxyphenyl)-3-(2-fluoro-4-(morpholin-2-yl)phenyl)urea hydrochloride

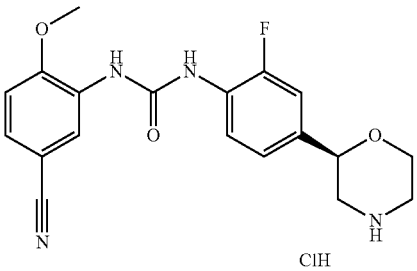 [SMILES: COc1ccc(C#N)cc1NC(=O)Nc1ccc([C@@H]2CNCCO2)cc1F ; Cl]

The title compound was obtained in analogy to example 39 using (+)-(R)-2-(4-amino-3-fluoro-phenyl)-morpholine-4-carboxylic acid tert-butyl ester (example 1 h) and 3-amino-4-methoxybenzonitrile (CAS 60979-25-1) in step a. Off-white solid. MS (ISP): 369.1 ([M+H]$^+$).

Example 45

(R)-1-(2-Chloro-4-(morpholin-2-yl)phenyl)-3-(5-cyano-2-methoxyphenyl)urea

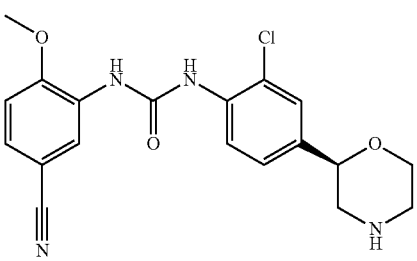 [SMILES: COc1ccc(C#N)cc1NC(=O)Nc1ccc([C@@H]2CNCCO2)cc1Cl]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 3-amino-4-methoxybenzonitrile (CAS 60979-25-1) in place of 3-aminobenzonitrile in step (h). White solid. MS (ISP): 389.1 ([{$^{37}$Cl}M+H]$^+$), 387.1 ([{$^{35}$Cl}M+H]$^+$).

Example 46

(S)-1-(2-Chloro-4-(morpholin-2-yl)phenyl)-3-(5-cyano-2-methoxyphenyl)urea

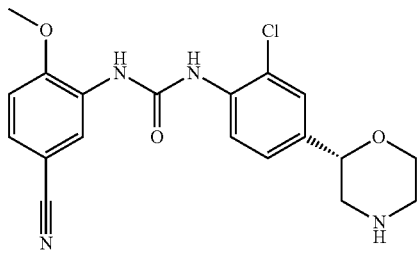 [SMILES: COc1ccc(C#N)cc1NC(=O)Nc1ccc([C@H]2CNCCO2)cc1Cl]

The title compound was obtained in analogy to example 5(h)-(i) using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 3-amino-4-methoxybenzonitrile (CAS 60979-25-1) in place of 3-aminobenzonitrile in step (h). White solid. MS (ISP): 389.1 ([{$^{37}$Cl}M+H]$^+$), 387.1 ([{$^{35}$Cl}M+H]$^+$).

Example 47

(R)-1-(2-Chloro-4-(morpholin-2-yl)phenyl)-3-(5-cyano-2-(difluoromethoxy)phenyl)urea

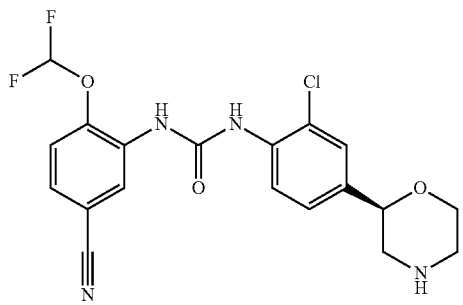 [SMILES: N#Cc1ccc(OC(F)F)c(NC(=O)Nc2ccc([C@@H]3CNCCO3)cc2Cl)c1]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 3-amino-4-(difluoromethoxy)benzonitrile (CAS 1211578-67-4) in place of 3-aminobenzonitrile in step (h). White solid. MS (ISP): 425.1 ([{$^{37}$Cl}M+H]$^+$), 423.1 ([{$^{35}$Cl}M+H]$^+$).

Example 48

(S)-1-(2-Chloro-4-(morpholin-2-yl)phenyl)-3-(5-cyano-2-(difluoromethoxy)phenyl)urea

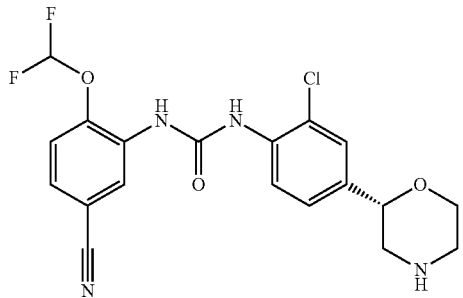 [SMILES: N#Cc1ccc(OC(F)F)c(NC(=O)Nc2ccc([C@H]3CNCCO3)cc2Cl)c1]

The title compound was obtained in analogy to example 5(h)-(i) using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 3-amino-4-(difluoromethoxy)benzonitrile (CAS 1211578-67-4) in place of 3-aminobenzonitrile in step (h). Off-white solid. MS (ISP): 425.1 ([{$^{37}$Cl}M+H]$^+$), 423.1 ([{$^{35}$Cl}M+H]$^+$).

Example 49

(R)-1-(2-Chloro-4-(morpholin-2-yl)phenyl)-3-(6-(trifluoromethyl)pyridin-3-yl)urea

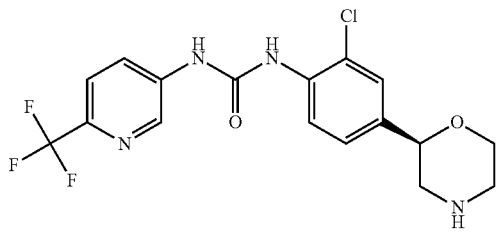 [SMILES: O=C(Nc1ccc(C(F)(F)F)nc1)Nc1ccc([C@@H]2CNCCO2)cc1Cl]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 6-(trifluoromethyl)pyridin-3-amine (CAS 106877-33-2) in place of 3-aminobenzonitrile in step (h). White solid. MS (ISP): 403.1 ([{$^{37}$Cl}M+H]$^+$), 401.1 ([{$^{35}$Cl}M+H]$^+$).

Example 50

(S)-1-(2-Chloro-4-(morpholin-2-yl)phenyl)-3-(6-(trifluoromethyl)pyridin-3-yl)urea

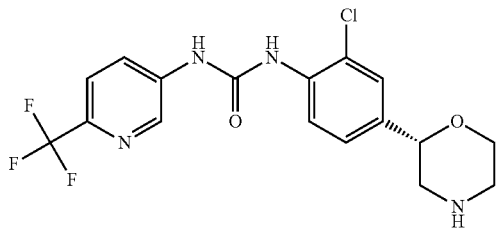 [SMILES: O=C(Nc1ccc(C(F)(F)F)nc1)Nc1ccc([C@H]2CNCCO2)cc1Cl]

The title compound was obtained in analogy to example 5(h)-(i) using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 6-(trifluoromethyl)pyridin-3-amine (CAS 106877-33-2) in place of 3-aminobenzonitrile in step (h). White solid. MS (ISP): 403.1 ([{$^{37}$Cl}M+H]$^+$), 401.1 ([{$^{35}$Cl}M+H]$^+$).

Example 51

1-((S)-2-Chloro-4-morpholin-2-yl-phenyl)-3-((2-trifluoromethyl-pyrimidin-5-yl)-urea

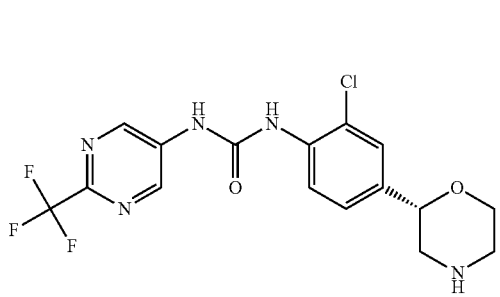 [SMILES: O=C(Nc1cnc(C(F)(F)F)nc1)Nc1ccc([C@H]2CNCCO2)cc1Cl]

The title compound was obtained in analogy to example 5(h)-(i) using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 2-(trifluoromethyl)-5-pyrimidinamine (CAS 73418-87-8) in place of 3-aminobenzonitrile in step (h). White solid. MS (ISP): 404.3 ([{$^{37}$Cl}M+H]$^+$), 402.3 ([{$^{35}$Cl}M+H]$^+$).

Example 52

1-((R)-2-Chloro-4-morpholin-2-yl-phenyl)-3-(2-trifluoromethyl-pyrimidin-5-yl)-urea

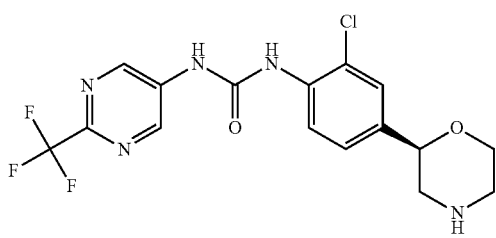 [SMILES: O=C(Nc1cnc(C(F)(F)F)nc1)Nc1ccc([C@@H]2CNCCO2)cc1Cl]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 2-(trifluoromethyl)-5-pyrimidinamine (CAS 73418-87-8) in place of 3-aminobenzonitrile in step (h). Off-white solid. MS (ISP): 404.3 ([{$^{37}$Cl}M+H]$^+$), 402.3 ([{$^{35}$Cl}M+H]$^+$).

Example 53

(S)-1-(2-Chloro-4-(morpholin-2-yl)phenyl)-3-(5-(trifluoromethyl)pyridin-2-yl)urea

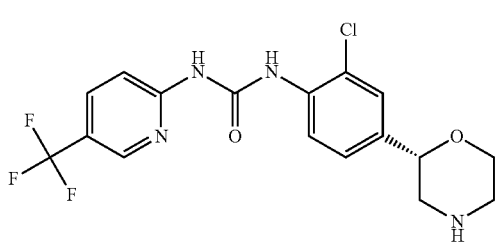 [SMILES: O=C(Nc1ccc(C(F)(F)F)cn1)Nc1ccc([C@H]2CNCCO2)cc1Cl]

The title compound was obtained in analogy to example 5(h)-(i) using (−)-tert-butyl (S)-2-(4-amino-3-chlorophenyl)morpholine-4-carboxylate (Example 29a) in place of tert-butyl (RS)-2-(4-amino-3-chlorophenyl)morpholine-4-carboxylate and 5-(trifluoromethyl)pyridin-2-amine (CAS 74784-70-6) in place of 3-aminobenzonitrile in step (h). White solid. MS (ISP): 403.1 ([{$^{37}$Cl}M+H]$^+$), 401.1 ([{$^{35}$Cl}M+H]$^+$).

Example 54

(R)-1-(2-Chloro-4-(morpholin-2-yl)phenyl)-3-(5-(trifluoromethyl)pyridin-2-yl)urea

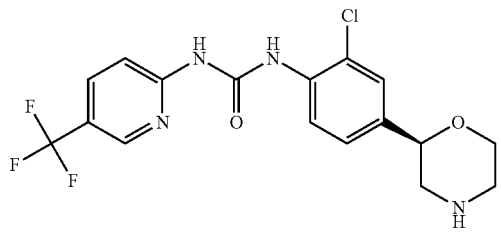 [SMILES: O=C(Nc1ccc(C(F)(F)F)cn1)Nc1ccc([C@@H]2CNCCO2)cc1Cl]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 5-(trifluoromethyl)pyridin-2-amine (CAS 74784-70-6) in place of 3-aminobenzonitrile in step (h). White solid. MS (ISP): 403.1 ([{$^{37}$Cl}M+H]$^+$), 401.1 ([{$^{35}$Cl}M+H]$^+$).

Example 55

(R)-1-(2-Chloro-4-(morpholin-2-yl)phenyl)-3-(5-chloropyridin-2-yl)urea

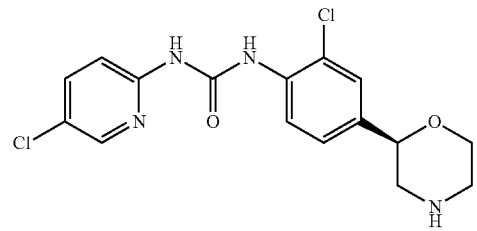 [SMILES: O=C(Nc1ccc(Cl)cn1)Nc1ccc([C@@H]2CNCCO2)cc1Cl]

The title compound was obtained in analogy to example 5(h)-(i) using (+)-tert-butyl (R)-2-(4-amino-3-chlorophenyl)morpholine-4-carboxylate (Example 29a) in place of tert-butyl (RS)-2-(4-amino-3-chlorophenyl)morpholine-4-carboxylate and 5-chloropyridin-2-amine (CAS 1072-98-6) in place of 3-aminobenzonitrile in step (h). White solid. MS (ISP): 371.1 ([{$^{37}$Cl}M+H]$^+$), 369.1 ([{$^{37}$Cl$^{35}$Cl}M+H]$^+$), 367.1 ([{$^{35}$Cl}M+H]$^+$).

Example 56

1-(5-Cyano-2-fluoro-phenyl)-3-((R)-2-fluoro-4-morpholin-2-yl-phenyl)-urea

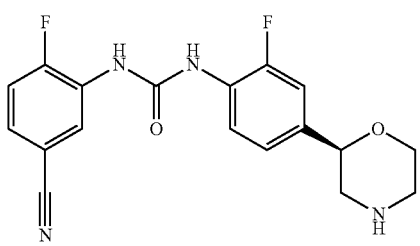 [SMILES: N#Cc1ccc(F)c(NC(=O)Nc2ccc([C@@H]3CNCCO3)cc2F)c1]

The title compound was obtained in analogy to example 3 using 3-amino-4-fluorobenzonitrile (CAS 859855-53-1) in place of 3-aminobenzonitrile in step (a). White solid. MS (ISP): 359.1 ([M+H]$^+$).

Example 57

1-((R)-2-Bromo-4-morpholin-2-yl-phenyl)-3-(5-cyano-2-methoxy-phenyl)-urea

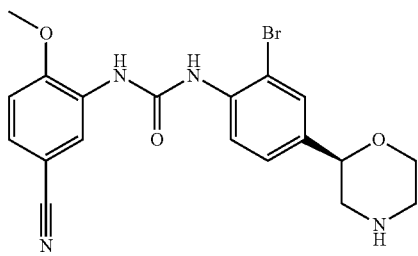 [SMILES: COc1ccc(C#N)cc1NC(=O)Nc1ccc([C@@H]2CNCCO2)cc1Br]

a) tert-Butyl (R)-2-(4-amino-3-bromophenyl)morpholine-4-carboxylate

To a stirred solution of tert-butyl (R)-2-(4-aminophenyl)morpholine-4-carboxylate (3.2 g, CAS 1260220-42-5) in DMF (25 ml) was added NBS (2.05 g) and the mixture was stirred at room temperature for 30 min. The reaction mixture was then poured into EtOAc and extracted sequentially with water and with saturated brine. The organic layer was dried over Na$_2$SO$_4$ and then concentrated in vacuo. The residue was purified by column chromatography (SiO$_2$, gradient: 0% to 70% EtOAc in heptanes) to give tert-butyl (R)-2-(4-amino-3-bromophenyl)morpholine-4-carboxylate (3.71 g, 90%) as an off-white solid. MS (ISP): 359.1 ([{$^{81}$Br}M+H]$^+$), 357.0 ([{$^{79}$Br}M+H]$^+$), 303.0 ([{$^{81}$Br}M+H—C$_4$H$_8$]$^+$), 301.0 ([{$^{79}$Br}M+H—C$_4$H$_8$]$^+$).

b) 1-((R)-2-Bromo-4-morpholin-2-yl-phenyl)-3-(5-cyano-2-methoxy-phenyl)-urea The title compound was obtained in analogy to example 37 using tert-butyl (R)-2-(4-amino-3-bromophenyl)morpholine-4-carboxylate in place of tert-butyl (RS)-2-(4-amino-3-bromophenyl)morpholine-4-carboxylate and 3-amino-4-methoxybenzonitrile (CAS 60979-25-1) in place of 6-chloropyridin-3-amine in step (a). White solid. MS (ISP): 433.2 ([{$^{81}$Br}M+H]$^+$), 431.1 ([{$^{79}$Br}M+H]$^+$).

Example 58

1-((S)-2-Bromo-4-morpholin-2-yl-phenyl)-3-(5-cyano-2-methoxy-phenyl)-urea

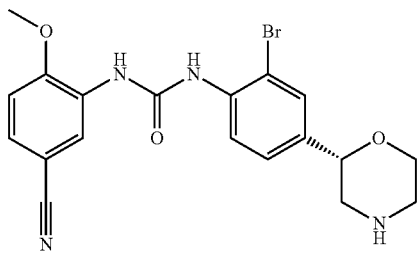 [SMILES: COc1ccc(C#N)cc1NC(=O)Nc1ccc([C@H]2CNCCO2)cc1Br]

The title compound was obtained in analogy to example 57 using tert-butyl (S)-2-(4-aminophenyl)morpholine-4-carboxylate (CAS 1260220-43-6) in place of tert-butyl (R)-2-(4-aminophenyl)morpholine-4-carboxylate in step (a). White solid. MS (ISP): 433.2 ([{$^{81}$Br}M+H]$^+$), 431.2 ([{$^{79}$Br}M+H]$^+$).

Example 59

1-(3-Cyano-5-fluoro-phenyl)-3-((R)-2-fluoro-4-morpholin-2-yl-phenyl)-urea

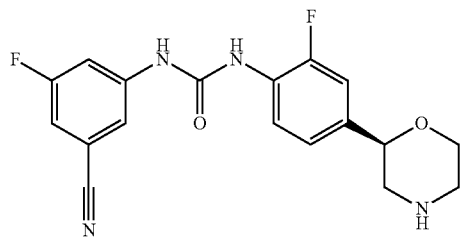 [SMILES: N#Cc1cc(F)cc(NC(=O)Nc2ccc([C@@H]3CNCCO3)cc2F)c1]

The title compound was obtained in analogy to example 3 using 3-amino-5-fluorobenzonitrile (CAS 210992-28-2) in place of 3-aminobenzonitrile in step (a). White solid. MS (ISP): 359.1 ([M+H]$^+$).

Example 60

1-((R)-2-Bromo-4-morpholin-2-yl-phenyl)-3-(5-cyano-2-difluoromethoxy-phenyl)-urea

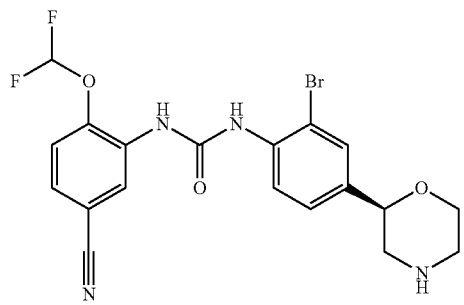

The title compound was obtained in analogy to example 57 using 3-amino-4-(difluoromethoxy)-benzonitrile (CAS 1211578-67-4) in place of 3-amino-4-methoxybenzonitrile in step (b). White solid. MS (ISP): 469.1 ([{$^{81}$Br}M+H]$^+$), 467.1 ([{$^{79}$Br}M+H]$^+$).

Example 61

1-((S)-2-Bromo-4-morpholin-2-yl-phenyl)-3-(5-cyano-2-difluoromethoxy-phenyl)-urea

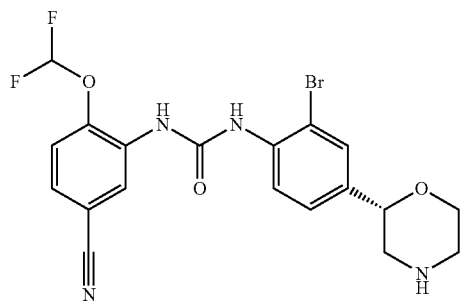

The title compound was obtained in analogy to example 57 using tert-butyl (S)-2-(4-aminophenyl)morpholine-4-carboxylate (CAS 1260220-43-6) in place of tert-butyl (R)-2-(4-aminophenyl)morpholine-4-carboxylate in step (a) and 3-amino-4-(difluoromethoxy)-benzonitrile (CAS 1211578-67-4) in place of 3-amino-4-methoxybenzonitrile in step (b). White solid. MS (ISP): 469.2 ([{$^{81}$Br}M+H]$^+$), 467.1 ([{$^{79}$Br}M+H]$^+$).

Example 62

(R)-1-(3-Cyano-2-fluorophenyl)-3-(2-fluoro-4-(morpholin-2-yl)phenyl)urea

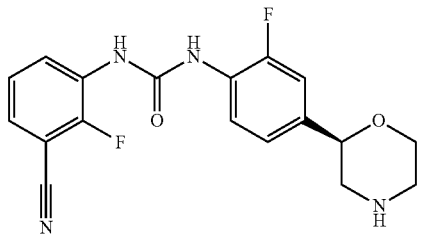 [SMILES: N#Cc1cccc(NC(=O)Nc2ccc([C@@H]3CNCCO3)cc2F)c1F]

The title compound was obtained in analogy to example 3 using 3-amino-2-fluorobenzonitrile (CAS 873697-68-8) in place of 3-aminobenzonitrile in step (a). White solid. MS (ISP): 359.1 ([M+H]$^+$).

Example 63

(R)-1-(3-Cyano-4-fluorophenyl)-3-(2-fluoro-4-(morpholin-2-yl)phenyl)urea

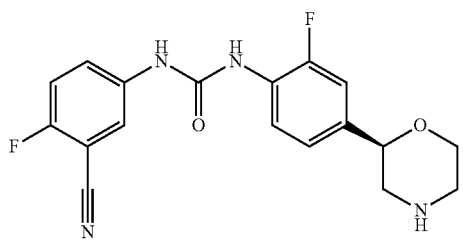 [SMILES: N#Cc1cc(NC(=O)Nc2ccc([C@@H]3CNCCO3)cc2F)ccc1F]

The title compound was obtained in analogy to example 3 using 5-amino-2-fluorobenzonitrile (CAS 53312-81-5) in place of 3-aminobenzonitrile in step (a). White solid. MS (ISP): 359.1 ([M+H]$^+$).

Example 64

(S)-1-(2-Chloro-4-(morpholin-2-yl)phenyl)-3-(5-chloropyridin-2-yl)urea

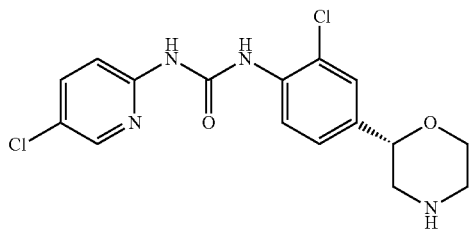 [SMILES: O=C(Nc1ccc(Cl)cn1)Nc1ccc([C@H]2CNCCO2)cc1Cl]

The title compound was obtained in analogy to example 5(h)-(i) using (−)-tert-butyl (S)-2-(4-amino-3-chlorophenyl) morpholine-4-carboxylate (Example 29a) in place of tert-butyl (RS)-2-(4-amino-3-chlorophenyl)morpholine-4-carboxylate and 5-chloropyridin-2-amine (CAS 1072-98-6) in place of 3-aminobenzonitrile in step (h). White solid. MS (ISP): 371.1 ([{$^{37}$Cl}M+H]$^+$), 369.1 ([{$^{37}$Cl$^{35}$Cl}M+H]$^+$), 367.1 ([{$^{35}$Cl}M+H]$^+$).

Example 65

(R)-1-(2-bromo-4-(morpholin-2-yl)phenyl)-3-(6-cyanopyridin-3-yl)urea

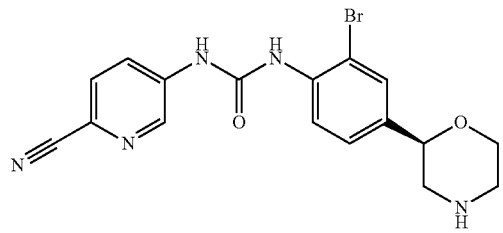 [SMILES: N#Cc1ccc(NC(=O)Nc2ccc([C@@H]3CNCCO3)cc2Br)cn1]

The title compound was obtained in analogy to example 57 using 5-amino-2-pyridinecarbonitrile (CAS 55338-73-3) in place of 3-amino-4-methoxybenzonitrile in step (b). White solid. MS (ISP): 404.1 ([{$^{81}$Br}M+H]$^+$), 402.1 ([{$^{79}$Br}M+H]$^+$).

Example 66

(S)-1-(2-bromo-4-(morpholin-2-yl)phenyl)-3-(6-cyanopyridin-3-yl)urea

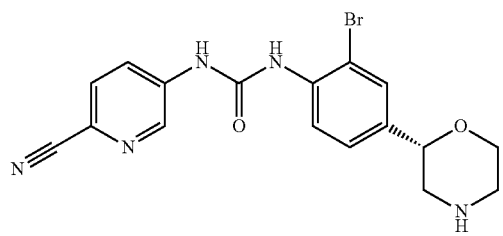 [SMILES: N#Cc1ccc(NC(=O)Nc2ccc([C@H]3CNCCO3)cc2Br)cn1]

The title compound was obtained in analogy to example 57 using tert-butyl (S)-2-(4-aminophenyl)morpholine-4-carboxylate (CAS 1260220-43-6) in place of tert-butyl (R)-2-(4-aminophenyl)morpholine-4-carboxylate in step (a) and 5-amino-2-pyridinecarbonitrile (CAS 55338-73-3) in place of 3-amino-4-methoxybenzonitrile in step (b). White solid. MS (ISP): 404.1 ([{$^{81}$Br}M+H]$^+$), 402.1 ([{$^{79}$Br}M+H]$^+$).

Example 67

1-((R)-2-Bromo-4-morpholin-2-yl-phenyl)-3-(6-chloro-pyridin-3-yl)-urea

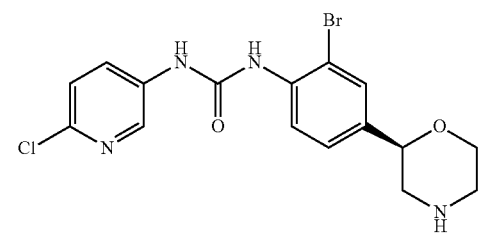 [SMILES: O=C(Nc1ccc(Cl)nc1)Nc1ccc([C@@H]2CNCCO2)cc1Br]

The title compound was obtained in analogy to example 57 using 6-chloro-3-aminopyridine (CAS 5350-93-6) in place of 3-amino-4-methoxybenzonitrile in step (b). Off-white solid.

MS (ISP): 415.2 ([{$^{81}$Br$^{37}$Cl}M+H]$^+$), 413.0 ([{$^{81}$Br$^{35}$Cl or $^{79}$Br$^{37}$Cl}M+H]$^+$), 411.1 ([{$^{79}$Br$^{35}$Cl}M+H]$^+$).

Example 68

1-((S)-2-Bromo-4-morpholin-2-yl-phenyl)-3-(6-chloro-pyridin-3-yl)-urea

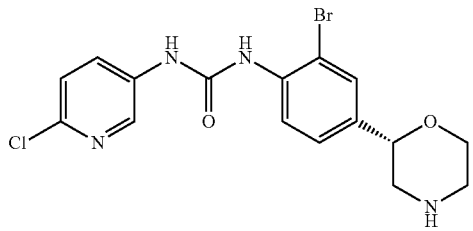 [SMILES: O=C(Nc1ccc(Cl)nc1)Nc1ccc([C@H]2CNCCO2)cc1Br]

The title compound was obtained in analogy to example 57 using tert-butyl (S)-2-(4-aminophenyl)morpholine-4-carboxylate (CAS 1260220-43-6) in place of tert-butyl (R)-2-(4-aminophenyl)morpholine-4-carboxylate in step (a) and 6-chloro-3-aminopyridine (CAS 5350-93-6) in place of 3-amino-4-methoxybenzonitrile in step (b). White solid. MS (ISP): 415.2 ([{$^{81}$Br$^{37}$Cl}M+H]$^+$), 413.1 ([{$^{81}$Br$^{35}$Cl or $^{79}$Br$^{37}$Cl}M+H]$^+$), 411.1 ([{$^{79}$Br$^{35}$Cl}M+H]$^+$).

Example 69

1-((S)-2-Bromo-4-morpholin-2-yl-phenyl)-3-(2-trifluoromethyl-pyrimidin-5-yl)-urea

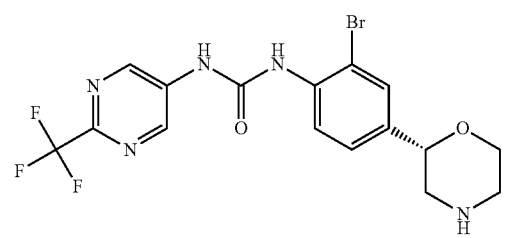 [SMILES: O=C(Nc1cnc(C(F)(F)F)nc1)Nc1ccc([C@H]2CNCCO2)cc1Br]

The title compound was obtained in analogy to example 57 using tert-butyl (S)-2-(4-aminophenyl)morpholine-4-carboxylate (CAS 1260220-43-6) in place of tert-butyl (R)-2-(4-aminophenyl)morpholine-4-carboxylate in step (a) and 5-amino-2-(trifluoromethyl)pyrimidine (CAS 73418-87-8) in place of 3-amino-4-methoxybenzonitrile in step (b). Off-white solid. MS (ISP): 447.9 ([{$^{81}$Br}M+H]$^+$), 446.0 ([{$^{79}$Br}M+H]$^+$).

Example 70

1-((R)-2-Bromo-4-morpholin-2-yl-phenyl)-3-(2-trifluoromethyl-pyrimidin-5-yl)-urea

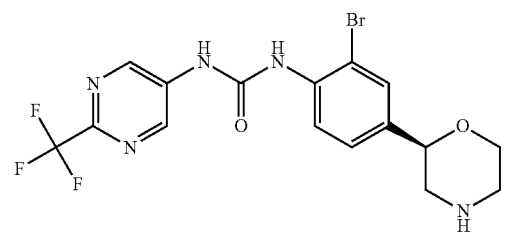 [SMILES: O=C(Nc1cnc(C(F)(F)F)nc1)Nc1ccc([C@@H]2CNCCO2)cc1Br]

The title compound was obtained in analogy to example 57 using 5-amino-2-(trifluoromethyl)pyrimidine (CAS 73418-87-8) in place of 3-amino-4-methoxybenzonitrile in step (b). Off-white solid. MS (ISP): 447.9 ([{$^{81}$Br}M+H]$^+$), 446.1 ([{$^{79}$Br}M+H]$^+$).

Example 71

1-(5-Cyano-2-difluoromethoxy-phenyl)-3-((S)-2-fluoro-4-morpholin-2-yl-phenyl)-urea hydrochloride

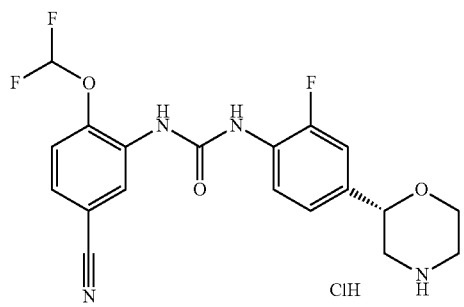 [SMILES: N#Cc1ccc(OC(F)F)c(NC(=O)Nc2ccc([C@H]3CNCCO3)cc2F)c1 ; Cl]

The title compound was obtained in analogy to example 39 using 3-amino-4-(difluoromethoxy)benzonitrile (CAS 1211578-67-4) in step a. White solid. MS (ISP): 407.2 ([M+H]$^+$).

Example 72

1-(5-Cyano-2-difluoromethoxy-phenyl)-3-((R)-2-fluoro-4-morpholin-2-yl-phenyl)-urea hydrochloride

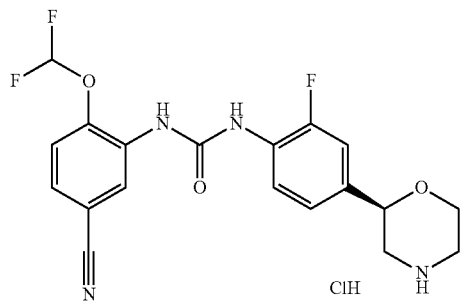 [SMILES: N#Cc1ccc(OC(F)F)c(NC(=O)Nc2ccc([C@@H]3CNCCO3)cc2F)c1 ; Cl]

The title compound was obtained in analogy to example 39 using (+)-(R)-2-(4-amino-3-fluoro-phenyl)-morpholine-4-carboxylic acid tert-butyl ester (example 1 h) and 3-amino-4-(difluoromethoxy)benzonitrile (CAS 1211578-67-4) in step a. White solid. MS (ISP): 407.3 ([M+H]$^+$).

Example 73

(S)-1-(5-Cyano-2-ethoxyphenyl)-3-(2-fluoro-4-(morpholin-2-yl)phenyl)urea hydrochloride

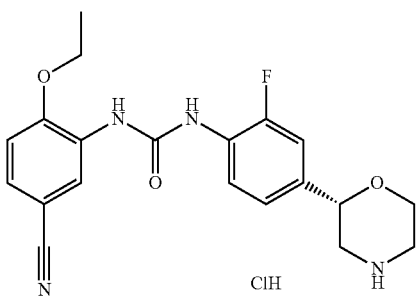 [SMILES: CCOc1ccc(C#N)cc1NC(=O)Nc1ccc([C@H]2CNCCO2)cc1F ; Cl]

The title compound was obtained in analogy to example 39 using 3-amino-4-ethoxybenzonitrile (CAS 72635-79-1) in step a. Off-white solid. MS (ISP): 383.2 ([M+H]⁺).

Example 74

(R)-1-(5-Cyano-2-ethoxyphenyl)-3-(2-fluoro-4-(morpholin-2-yl)phenyl)urea hydrochloride

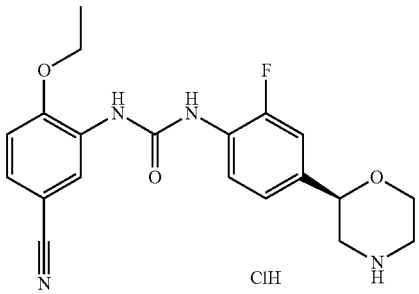 [SMILES: CCOc1ccc(C#N)cc1NC(=O)Nc1ccc([C@@H]2CNCCO2)cc1F ; Cl]

The title compound was obtained in analogy to example 39 using (+)-(R)-2-(4-amino-3-fluoro-phenyl)-morpholine-4-carboxylic acid tert-butyl ester (example 1 h) and 3-amino-4-ethoxybenzonitrile (CAS 72635-79-1) in step a. Off-white solid. MS (ISP): 383.2 ([M+H]⁺).

Example 75

(S)-1-(3-(Difluoromethoxy)phenyl)-N-(2-fluoro-4-(morpholin-2-yl)phenyl)-1H-pyrazole-4-carboxamide

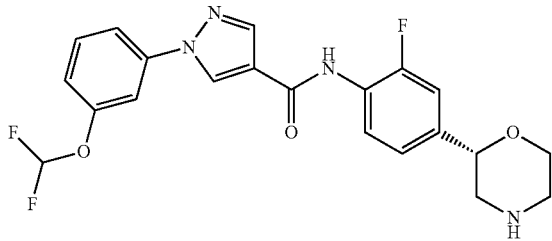 [SMILES: O=C(Nc1ccc([C@H]2CNCCO2)cc1F)c1cnn(-c2cccc(OC(F)F)c2)c1]

a) Ethyl 1-(3-(difluoromethoxy)phenyl)-1H-pyrazole-4-carboxylate (3-(Difluoromethoxy)phenyl)hydrazine hydrochloride (4.2 g, 19.9 mmol; CAS 479581-64-1) was suspended in ethanol (80 ml) and cooled to 0° C. A solution of ethyl 2-formyl-3-oxopropanoate (2.87 g, 19.9 mmol; CAS 80370-42-9) in ethanol (40 ml) was added, and the reaction was stirred overnight. The solvent was removed under reduced pressure and the residue partitioned between sodium bicarbonate solution and ethyl acetate. The organic layers were combined, dried (MgSO₄) and evaporated to yield an orange solid. The solid was suspended in pentane (50 ml) and stirred at 35° C. for 90 min. The suspension was cooled in an ice bath for one hour and the solid was filtered and washed with pentane. After drying 5.12 g (91%) of a yellow solid was obtained MS (ISP): 283.1 ([M+H]⁺).

b) 1-(3-(Difluoromethoxy)phenyl)-1H-pyrazole-4-carboxylic acid

To a solution of ethyl 1-(3-(difluoromethoxy)phenyl)-1H-pyrazole-4-carboxylate (5 g, 17.7 mmol) in a mixture of THF (100 ml), methanol (50 ml) and water (50 ml) lithium hydroxide hydrate (2.23 g, 53.1 mmol) was added. The solution was heated to 80° C. for 2 h. Most of the organic solvent was removed under reduced pressure. Sodium bicarbonate solution was added and the organic layer was separated. The aqueous layer was made acidic by addition of 25% aq. hydrochloric acid (until acidic pH) and the mixture was extracted two times with ethyl acetate. The organic layers were combined, dried (MgSO₄) and evaporated to yield a solid. The solid was stirred in a mixture of heptane and ethyl acetate for 2 h, filtered off and dried to yield 1-(3-(difluoromethoxy)phenyl)-1H-pyrazole-4-carboxylic acid as an off-white solid (3.5 g, 78%) which was used for the next step.

c) (S)-tert-Butyl 2-(4-(1-(3-(difluoromethoxy)phenyl)-1H-pyrazole-4-carboxamido)-3-fluorophenyl)morpholine-4-carboxylate (S)-tert-Butyl 2-(4-amino-3-fluorophenyl)morpholine-4-carboxylate (104 mg, 0.35 mmol), 1-(3-(difluoromethoxy)phenyl)-1H-pyrazole-4-carboxylic acid (107 mg, 0.42 mmol), HBTU (200 mg, 0.525 mmol) and N-methylmorpholine (106 mg, 115 µl, 1.05 mmol) were combined with DMF (4 ml) to give a light yellow solution. The reaction mixture was stirred at room temperature for 17 hours. The reaction mixture was poured into 50 ml of water and extracted with ethyl acetate twice. The combined organic layers were washed with brine, dried over MgSO4 and concentrated in vacuo. The crude material was purified by flash chromatography (20 g Silica gel, 70 to 50% ethyl acetate in heptane) to yield a white solid (110 mg, 59%). MS (ISP): 477.1 (100%, [M-tBu+H]⁺), 533.2 (30%, [M+H]⁺).

d) (S)-1-(3-(Difluoromethoxy)phenyl)-N-(2-fluoro-4-(morpholin-2-yl)phenyl)-1H-pyrazole-4-carboxamide hydrochloride (S)-tert-butyl 2-(4-(1-(3-(difluoromethoxy)phenyl)-1H-pyrazole-4-carboxamido)-3-fluorophenyl)morpholine-4-carboxylate (102 mg, 0.2 mmol) was dissolved in dioxane (0.75 ml) and a solution of HCl in dioxane (4M, 0.75 ml, 3 mmol) was added. The reaction mixture was stirred for 90 min at 60° C. After cooling ether was added, the solid was filtered off, washed with ether and dried in vacuo at 60° C. to afford (S)-1-(3-(difluoromethoxy)phenyl)-N-(2-fluoro-4-(morpholin-2-yl)phenyl)-1H-pyrazole-4-carboxamide hydrochloride (84 mg, 91%) as a white solid. MS (ISP): 433.2 ([M+H]⁺).

Example 76

(S)-1-(4-(Difluoromethoxy)phenyl)-N-(2-fluoro-4-(morpholin-2-yl)phenyl)-1H-pyrazole-4-carboxamide

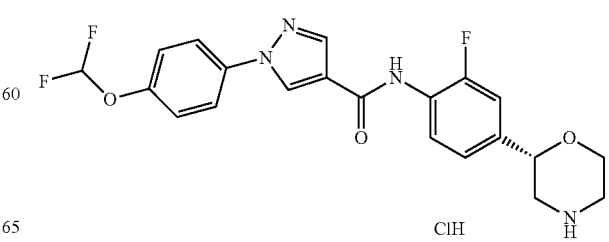

The title compound was obtained in analogy to example 75 using (4-(difluoromethoxy)phenyl)hydrazine hydrochloride instead of (3-(difluoromethoxy)phenyl)hydrazine hydrochloride in step a). White solid. MS (ISP): 433.3 ([M+H]+).

Example 77

(R)-1-(3-(Difluoromethoxy)benzyl)-3-(2-fluoro-4-(morpholin-2-yl)phenyl)urea

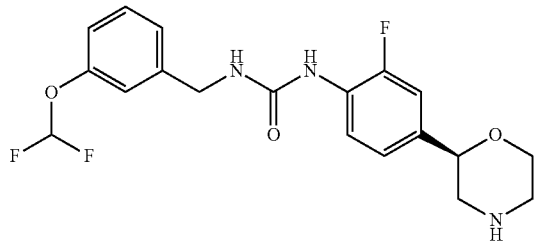 [SMILES: O=C(NCc1cccc(OC(F)F)c1)Nc1ccc([C@@H]2CNCCO2)cc1F]

The title compound was obtained in analogy to example 3 using (3-(difluoromethoxy)phenyl)methanamine (CAS 244022-71-7) in place of 3-aminobenzonitrile in step (a). Colourless amorphous solid. MS (ISP): 396.2 ([M+H]+).

Example 78

(S)-1-(3-(Difluoromethoxy)benzyl)-3-(2-fluoro-4-(morpholin-2-yl)phenyl)urea

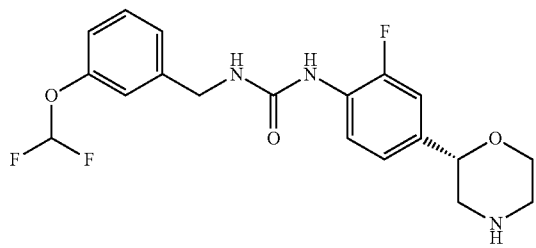 [SMILES: O=C(NCc1cccc(OC(F)F)c1)Nc1ccc([C@H]2CNCCO2)cc1F]

The title compound was obtained in analogy to example 3 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and (3-(difluoromethoxy)phenyl)methanamine (CAS 244022-71-7) in place of 3-aminobenzonitrile in step (a). White solid. MS (ISP): 396.2 ([M+H]+).

Example 79

(S)-4-Cyano-N-(2-fluoro-4-(morpholin-2-yl)phenyl)picolinamide hydrochloride

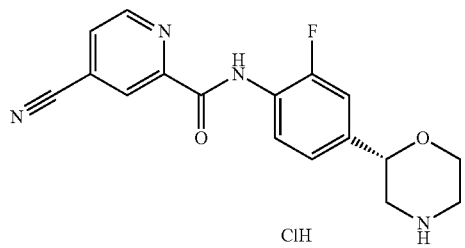 [SMILES: N#Cc1ccnc(C(=O)Nc2ccc([C@H]3CNCCO3)cc2F)c1 ; Cl]

a) (S)-2-{4-[(4-Cyano-pyridine-2-carbonyl)-amino]-3-fluoro-phenyl}-morpholine-4-carboxylic acid tert-butyl ester (−)-(S)-2-(4-Amino-3-fluoro-phenyl)-morpholine-4-carboxylic acid tert-butyl ester (example 1 h, 70 mg, 236 μmol, Eq: 1.00), 4-cyanopicolinic acid (CAS 640296-19-1, 45.5 mg, 307 μmol, Eq: 1.3) and HBTU (134 mg, 354 μmol, Eq: 1.5) were dissolved in DMF (1.25 ml), treated with N-Methylmorpholin (71.7 mg, 77.9 μl, 709 μmol, Eq: 3) and stirred at r.t. for 17 h. The mixture was diluted with water and extracted twice with ethyl acetate. The combined organic layers were washed with brine, dried over MgSO4, filtered off and concentrated under vacuo. The solid residue was diluted with a small volume of MeOH, and filtered, leading to 64 mg of a white solid.

MS (ISP): 371.0 ([M+H—C4H8]+).

b) (S)-4-Cyano-N-(2-fluoro-4-(morpholin-2-yl)phenyl)picolinamide hydrochloride

To a solution of (S)-2-{4-[(4-Cyano-pyridine-2-carbonyl)-amino]-3-fluoro-phenyl}-morpholine-4-carboxylic acid tert-butyl ester (73 mg, 171 μmol, Eq: 1.00) in THF (3 ml) was added 4M-HCl in dioxane (0.642 ml, 2.52 mmol, Eq: 15). The reaction mixture was stirred at 60° C. for 5 h. To the cooled mixture was then added ethyl acetate and the suspension was filtered off and dried under high vacuo to give the target compound as a white solid (53 mg, 85%). MS (ISP): 325.2 ([M+H]+).

Example 80

(R)-4-Cyano-N-(2-fluoro-4-(morpholin-2-yl)phenyl)picolinamide hydrochloride

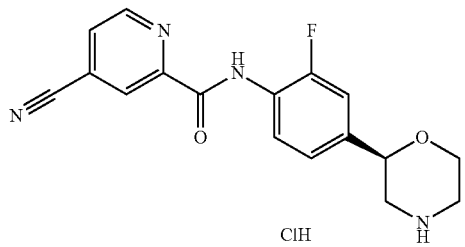 [SMILES: N#Cc1ccnc(C(=O)Nc2ccc([C@@H]3CNCCO3)cc2F)c1 ; Cl]

In analogy to example 79, step a) using (+)-(R)-2-(4-amino-3-fluoro-phenyl)-morpholine-4-carboxylic acid tert-butyl ester (example 1 h) in place of (−)-(S)-2-(4-amino-3-fluoro-phenyl)-morpholine-4-carboxylic acid tert-butyl ester. White solid. MS (ISP): 325.2 ([M+H]+)

Example 81

(S)-6-Cyano-N-(2-fluoro-4-(morpholin-2-yl)phenyl)picolinamide hydrochloride

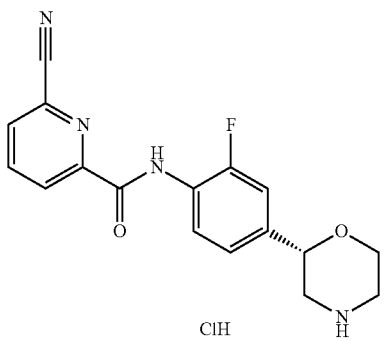 [SMILES: N#Cc1cccc(C(=O)Nc2ccc([C@H]3CNCCO3)cc2F)n1 ; Cl]

In analogy to example 79, step a) using 6-cyano-2-pyridinecarboxylic acid (CAS 872602-74-9). White solid. MS (ISP): 325.3 ([M+H]+)

Example 82

(S)-1-(2,2-Difluorobenzo[d][1,3]dioxol-5-yl)-N-(2-fluoro-4-(morpholin-2-yl)phenyl)-1H-pyrazole-4-carboxamide

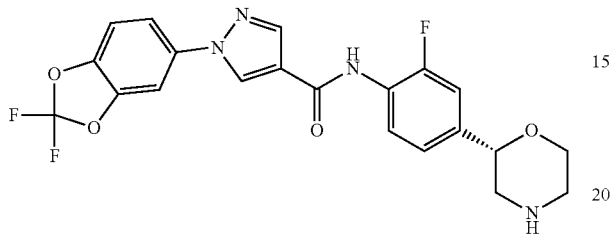

The title compound was obtained in analogy to example 75 using (2,2-difluorobenzo[d][1,3]-dioxol-5-yl)hydrazine hydrochloride instead of (3-(difluoromethoxy)phenyl)hydrazine hydrochloride in step a). Light yellow solid. MS (ISP): 447.2 ([M+H]+).

Example 83

(R)—N-(3-Fluoro-4-(morpholin-2-yl)phenyl)-2-(trifluoromethyl)isonicotinamide hydrochloride

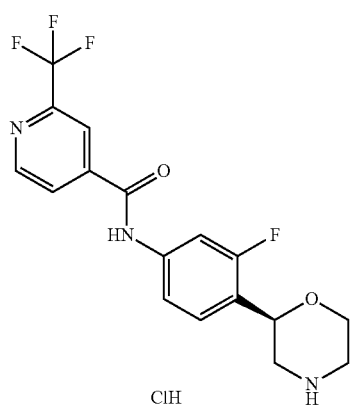 [SMILES: O=C(Nc1ccc([C@@H]2CNCCO2)c(F)c1)c1ccnc(C(F)(F)F)c1 ; Cl]

Step a) (R)-2-{2-Fluoro-4-[(2-trifluoromethyl-pyridine-4-carbonyl)-amino]-phenyl}-morpholine-4-carboxylic acid tert-butyl ester Under N2, 2-(trifluoromethyl)-4-pyridinecarboxylic acid (CAS 131747-41-6) (64.4 mg, 337 µmol, Eq: 1.00) was dissolved in CH$_2$Cl$_2$ (1 ml). 1-chloro-N,N2-trimethypropenylamine (51.8 mg, 51.3 µl, 388 µmol, Eq: 1.15) was added dropwise. After 30 minutes at RT, a solution contained (R)-2-(4-Amino-2-fluoro-phenyl)-morpholine-4-carboxylic acid tert-butyl ester (100 mg, 337 µmol, Eq: 1.00) and ethyldiisopropylamine (109 mg, 140 µl, 842 µmol, Eq: 2.5) in DMF (1.00 ml) was added. The RM was stirred at RT over 1 hour. Control with TLC: the reaction was finished. The RM was extracted with EtOAc and 1M citric acid solution; the organic phase was dried over MgSO4; filtered; concentrated in vacuo. The crude material was purified by flash chromatography (silica gel, 10 g, 10% to 50% EtOAc in heptane) leading to 149 mg (82%) of a white foam. MS (EIC): 468.1 ([M–H]−)

Step b) In Analogy to Example 79, Step b) Using Dioxane Instead of THF and 2 h Instead of 5 h at 60° C.

Yellow solid. MS (ISP): 370.1 ([M+H]+)

Preparation of (R) and (S)-2-(4-Amino-2-fluoro-phenyl)-morpholine-4-carboxylic acid tert-butyl ester a) (RS)-2-(4-Amino-2-fluoro-phenyl)-morpholine-4-carboxylic acid tert-butyl ester In analogy to (RS)-2-(4-Amino-3-fluoro-phenyl)-morpholine-4-carboxylic acid tert-butyl ester (Example 1, steps a-g) using 4-bromo-2-fluorobenzoyl chloride (CAS 151982-51-3) instead of 4-bromo-3-fluorobenzoyl chloride.

Following alternative procedure can be used in step (e) for the preparation of (RS)-2-(4-Bromo-2-fluoro-phenyl)-morpholine-4-carboxylic acid tert-butyl ester a) Under N2, tert-butyl 2-(4-bromo-2-fluoro-phenyl)-2-hydroxyethyl(2-hydroxyethyl)carbamate (7.385 g, 19.5 mmol, Eq: 1.00) and triphenylphosphine (6.15 g, 23.4 mmol, Eq: 1.2) were dissolved in TBME (33 ml). Under ice-bath cooling, DIAD (5.04 g, 4.85 ml, 23.4 mmol, Eq: 1.2) was added (exotherm). The yellow solution was stirred at RT overnight. The RM became a yellow suspension. Control with TLC: the reaction was finished. The solvent was evaporated. TBME was added and the solid was filtered. The filtrate was evaporated. The crude material was purified by flash chromatography (silica gel, 100 g, 5% to 40% EtOAc in heptane).

(+)-(R)-2-(4-Amino-2-fluoro-phenyl)-morpholine-4-carboxylic acid tert-butyl ester & (−)-(S)-2-(4-Amino-2-fluoro-phenyl)-morpholine-4-carboxylic acid tert-butyl ester b) The enantiomers of (RS)-2-(4-amino-2-fluoro-phenyl)-morpholine-4-carboxylic acid tert-butyl ester (5130 mg) were separated using chiral HPLC (column: Chiralpak AD, 5×50 cm; eluent: 15% isopropanol/heptane; pressure: 18 bar; flow rate: 35 ml/min) affording:

(+)-(R)-2-(4-Amino-2-fluoro-phenyl)-morpholine-4-carboxylic acid tert-butyl ester (1780 mg, off white solid), Retention time=83 min (−)-(S)-2-(4-Amino-2-fluoro-phenyl)-morpholine-4-carboxylic acid tert-butyl ester (2070 mg, light yellow solid), Retention time=96 min.

Example 84

(R)-2-Ethoxy-N-(3-fluoro-4-(morpholin-2-yl)phenyl)isonicotinamide hydrochloride

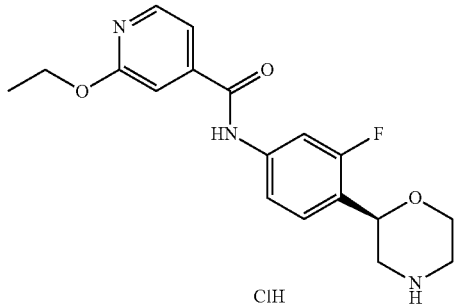 [SMILES: CCOc1cc(C(=O)Nc2ccc([C@@H]3CNCCO3)c(F)c2)ccn1 ; Cl]

In analogy to Example 83, step a) using 2-ethoxy-4-pyridinecarboxylic acid (CAS 91940-86-2) instead of 2-(trifluoromethyl)-4-pyridinecarboxylic acid (CAS 131747-41-6). Light yellow foam. MS (ISP): 346.1 ([M+H]$^+$)

Example 85

(R)-6-Ethoxy-N-(3-fluoro-4-(morpholin-2-yl)phenyl)nicotinamide hydrochloride

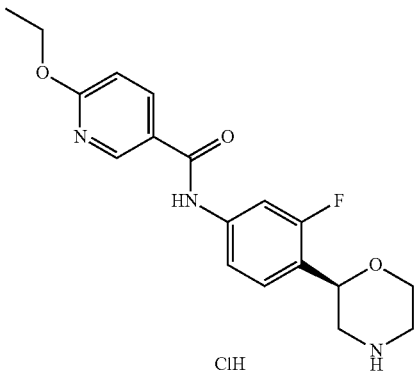 [SMILES: CCOc1ccc(C(=O)Nc2ccc([C@@H]3CNCCO3)c(F)c2)cn1 ; Cl]

In analogy to Example 83, step a) using 6-ethoxy-3-pyridinecarboxylic acid (CAS 97455-65-7) instead of 2-(trifluoromethyl)-4-pyridinecarboxylic acid (CAS 131747-41-6). White solid. MS (ISP): 346.1 ([M+H]$^+$)

Example 86

(R)-1-(4-(Difluoromethoxy)phenyl)-N-(3-fluoro-4-(morpholin-2-yl)phenyl)-1H-pyrazole-4-carboxamide hydrochloride

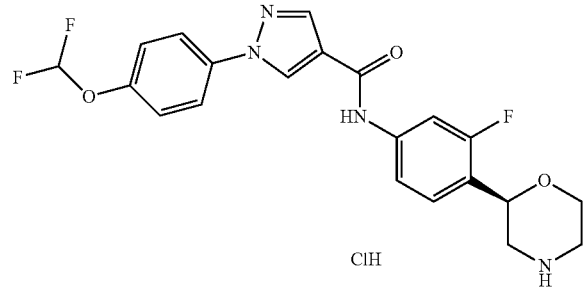 [SMILES: O=C(Nc1ccc([C@@H]2CNCCO2)c(F)c1)c1cnn(-c2ccc(OC(F)F)cc2)c1 ; Cl]

In analogy to Example 83, step a) using 1-(4-difluoromethoxy-phenyl)-1H-pyrazole-4-carboxylic acid instead of 2-(trifluoromethyl)-4-pyridinecarboxylic acid (CAS 131747-41-6). White solid. MS (ISP): 433.3 ([M+H]$^+$)

1-(4-Difluoromethoxy-phenyl)-1H-pyrazole-4-carboxylic acid was obtained in analogy to example 75 steps (a-b) using (4-(difluoromethoxy)phenyl)hydrazine hydrochloride instead of (3-(difluoromethoxy)phenyl)hydrazine hydrochloride in step a).

Example 87

(S)—N-(3-Fluoro-4-(morpholin-2-yl)phenyl)-2-(trifluoromethyl)isonicotinamide hydrochloride

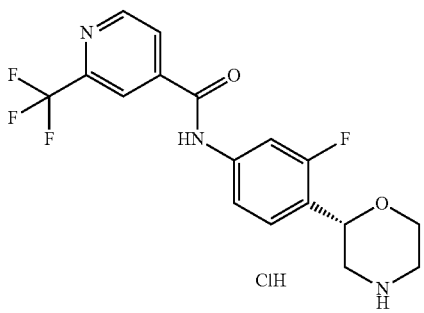 [SMILES: O=C(Nc1ccc([C@H]2CNCCO2)c(F)c1)c1ccnc(C(F)(F)F)c1 ; Cl]

In analogy to Example 83, step a) using (−)-(S)-2-(4-Amino-2-fluoro-phenyl)-morpholine-4-carboxylic acid tert-butyl ester instead of (+)-(R)-2-(4-Amino-2-fluoro-phenyl)-morpholine-4-carboxylic acid tert-butyl ester. Off-white solid. MS (ISP): 370.1 ([M+H]$^+$)

Example 88

(S)-2-Ethoxy-N-(3-fluoro-4-(morpholin-2-yl)phenyl)isonicotinamide hydrochloride

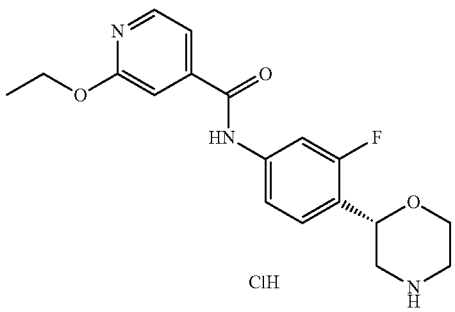 [SMILES: CCOc1cc(C(=O)Nc2ccc([C@H]3CNCCO3)c(F)c2)ccn1 ; Cl]

In analogy to Example 83, step a) using 2-ethoxy-4-pyridinecarboxylic acid (CAS 91940-86-2) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester instead of (+)-(R)-2-(4-Amino-2-fluoro-phenyl)-morpholine-4-carboxylic acid tert-butyl ester.

Yellow foam. MS (ISP): 346.1 ([M+H]$^+$)

Example 89

(S)-6-Ethoxy-N-(3-fluoro-4-(morpholin-2-yl)phenyl) nicotinamide hydrochloride

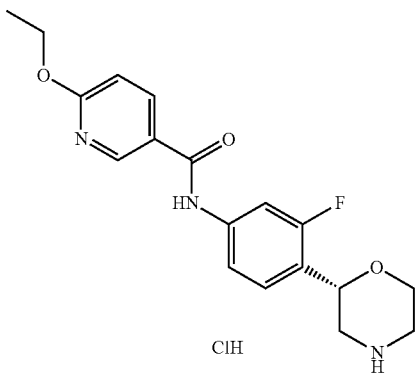 [SMILES: CCOc1ccc(C(=O)Nc2ccc([C@H]3CNCCO3)c(F)c2)cn1 ; Cl]

In analogy to Example 83, step a) using 6-ethoxy-3-pyridinecarboxylic acid (CAS 97455-65-7) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester instead of (+)-(R)-2-(4-Amino-2-fluoro-phenyl)-morpholine-4-carboxylic acid tert-butyl ester. White solid. MS (ISP): 346.1 ([M+H]$^+$)

Example 90

(S)-1-(4-(Difluoromethoxy)phenyl)-N-(3-fluoro-4-(morpholin-2-yl)phenyl)-1H-pyrazole-4-carboxamide hydrochloride

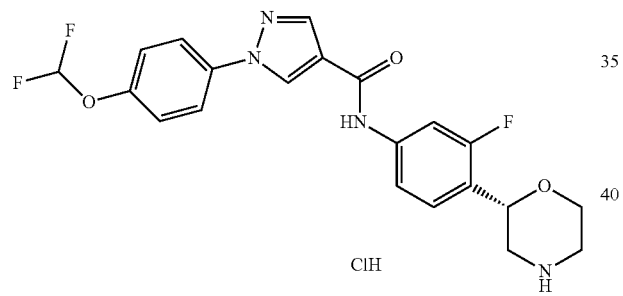

In analogy to Example 86, step a) using (−)-(S)-2-(4-Amino-2-fluoro-phenyl)-morpholine-4-carboxylic acid tert-butyl ester instead of (+)-(R)-2-(4-Amino-2-fluoro-phenyl)-morpholine-4-carboxylic acid tert-butyl ester. White solid. MS (ISP): 449.1 ([M+H]$^+$)

Example 91

(R)—N-(3-Chloro-4-(morpholin-2-yl)phenyl)-2-ethoxyisonicotinamide hydrochloride

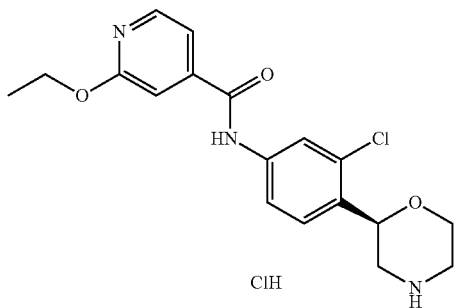 [SMILES: CCOc1cc(C(=O)Nc2ccc([C@@H]3CNCCO3)c(Cl)c2)ccn1 ; Cl]

In analogy to Example 83, step a) using 2-ethoxy-4-pyridinecarboxylic acid (CAS 91940-86-2) instead of 2-(trifluoromethyl)-4-pyridinecarboxylic acid (CAS 131747-41-6) and (+)-(R)-2-(4-Amino-2-chloro-phenyl)-morpholine-4-carboxylic acid tert-butyl ester instead of (+)-(R)-2-(4-Amino-2-fluoro-phenyl)-morpholine-4-carboxylic acid tert-butyl ester. Light yellow foam. MS (ISP): 362.0 ([M+H]$^+$)

Preparation of (R) and (S)-2-(4-Amino-2-chloro-phenyl)-morpholine-4-carboxylic acid tert-butyl ester a) (RS)-2-(4-Amino-2-chloro-phenyl)-morpholine-4-carboxylic acid tert-butyl ester In analogy to (RS)-2-(4-Amino-3-fluoro-phenyl)-morpholine-4-carboxylic acid tert-butyl ester (Example 1, steps a-g) using 4-bromo-2-chlorobenzoyl chloride (CAS 21900-55-0) instead of 4-bromo-3-fluorobenzoyl chloride.

b) (+)-(R)-2-(4-Amino-2-chloro-phenyl)-morpholine-4-carboxylic acid tert-butyl ester & (−)-(S)-2-(4-Amino-2-chloro-phenyl)-morpholine-4-carboxylic acid tert-butyl ester The enantiomers of (RS)-2-(4-amino-2-chloro-phenyl)-morpholine-4-carboxylic acid tert-butyl ester (1640 mg) were separated using chiral HPLC (column: Chiralpak AD, 5×50 cm; eluent: 15% isopropanol/heptane; pressure: 18 bar; flow rate: 35 ml/min) affording: (+)-(R)-2-(4-Amino-2-chloro-phenyl)-morpholine-4-carboxylic acid tert-butyl ester (772 mg, light yellow solid), Retention time=51 min (−)-(S)-2-(4-Amino-2-chloro-phenyl)-morpholine-4-carboxylic acid tert-butyl ester (793 mg, light yellow solid), Retention time=68 min.

Example 92

(R)—N-(3-Chloro-4-(morpholin-2-yl)phenyl)-6-ethoxynicotinamide hydrochloride

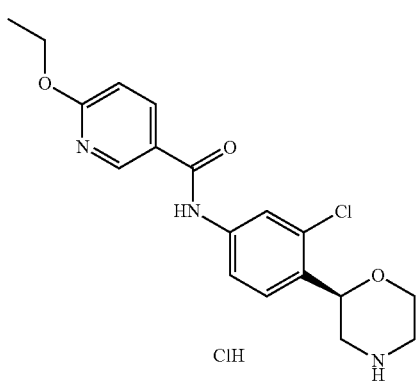 [SMILES: CCOc1ccc(C(=O)Nc2ccc([C@@H]3CNCCO3)c(Cl)c2)cn1 ; Cl]

In analogy to Example 83, step a) using 6-ethoxy-3-pyridinecarboxylic acid (CAS 97455-65-7) instead of 2-(trifluoromethyl)-4-pyridinecarboxylic acid (CAS 131747-41-6) and (+)-(R)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. Off-white solid. MS (ISP): 362.0 ([M+H]$^+$)

Example 93

(R)—N-(3-Chloro-4-(morpholin-2-yl)phenyl)-1-(4-(difluoromethoxy)phenyl)-1H-pyrazole-4-carboxamide hydrochloride

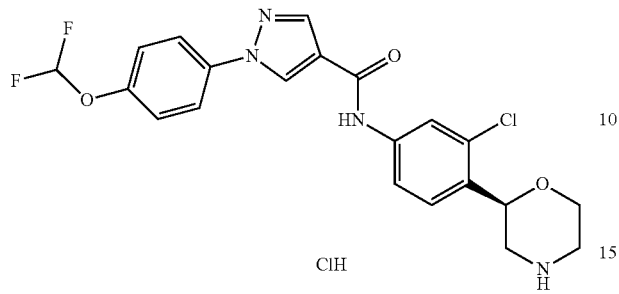

In analogy to Example 86, step a) using (+)-(R)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. White solid. MS (ISP): 449.1 ([M+H]$^+$)

Example 94

(S)—N-(3-Chloro-4-(morpholin-2-yl)phenyl)-2-ethoxyisonicotinamide hydrochloride

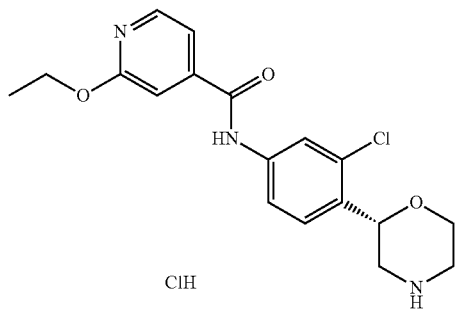 [SMILES: CCOc1cc(C(=O)Nc2ccc([C@H]3CNCCO3)c(Cl)c2)ccn1 ; Cl]

In analogy to Example 83, step a) using 2-ethoxy-4-pyridinecarboxylic acid (CAS 91940-86-2) instead of 2-(trifluoromethyl)-4-pyridinecarboxylic acid (CAS 131747-41-6) and (−)-(S)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. Light yellow foam. MS (ISP): 362.0 ([M+H]$^+$)

Example 95

(S)—N-(3-Chloro-4-(morpholin-2-yl)phenyl)-6-ethoxynicotinamide hydrochloride

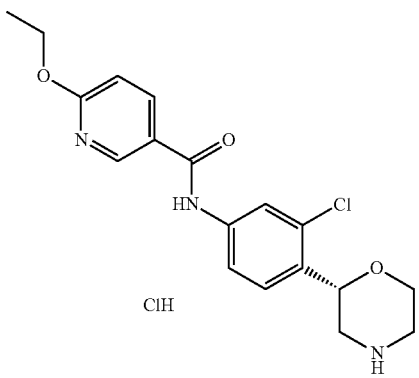 [SMILES: CCOc1ccc(C(=O)Nc2ccc([C@H]3CNCCO3)c(Cl)c2)cn1 ; Cl]

In analogy to Example 83, step a) using 6-ethoxy-3-pyridinecarboxylic acid (CAS 97455-65-7) instead of 2-(trifluoromethyl)-4-pyridinecarboxylic acid (CAS 131747-41-6) and (−)-(S)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. White solid. MS (ISP): 362.0 ([M+H]$^+$)

Example 96

(S)—N-(3-Chloro-4-(morpholin-2-yl)phenyl)-1-(4-(difluoromethoxy)phenyl)-1H-pyrazole-4-carboxamide hydrochloride

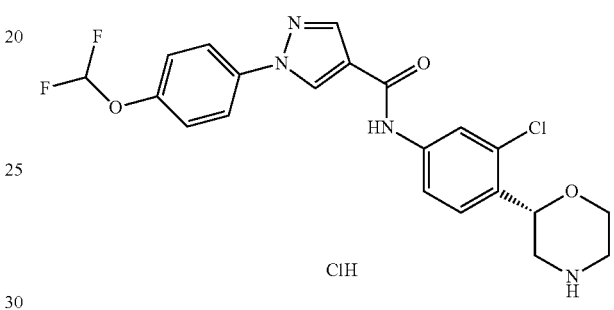

In analogy to Example 86, step a) using (−)-(S)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. White solid. MS (ISP): 449.1 ([M+H]$^+$)

Example 97

(R)—N-(2-Chloro-4-(morpholin-2-yl)phenyl)-6-cyanopicolinamide hydrochloride

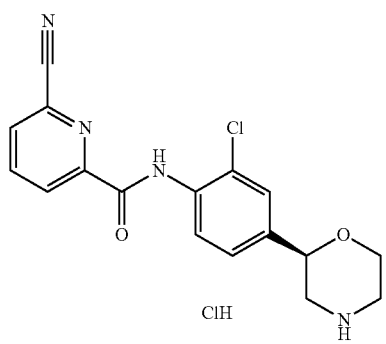 [SMILES: N#Cc1cccc(C(=O)Nc2ccc([C@@H]3CNCCO3)cc2Cl)n1 ; Cl]

In analogy to example 79, step a) using 6-cyano-2-pyridinecarboxylic acid (CAS 872602-74-9) instead of 4-cyanopicolinic acid (CAS 640296-19-1) and (+)-(R)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 98

(S)—N-(2-Chloro-4-(morpholin-2-yl)phenyl)-6-cyanopicolinamide hydrochloride

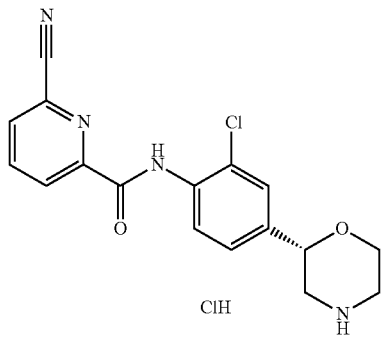 [SMILES: N#Cc1cccc(C(=O)Nc2ccc([C@H]3CNCCO3)cc2Cl)n1 ; Cl]

In analogy to example 79, step a) using 6-cyano-2-pyridinecarboxylic acid (CAS 872602-74-9) instead of 4-cyanopicolinic acid (CAS 640296-19-1) and (−)-(S)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 99

(S)—N-(2-Chloro-4-(morpholin-2-yl)phenyl)-5-cyanopicolinamide hydrochloride

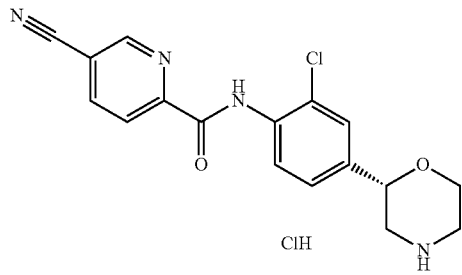 [SMILES: N#Cc1ccc(C(=O)Nc2ccc([C@H]3CNCCO3)cc2Cl)nc1 ; Cl]

In analogy to example 79, step a) using 5-cyano-2-pyridinecarboxylic acid (CAS 53234-55-2) instead of 4-cyanopicolinic acid (CAS 640296-19-1) and (−)-(S)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 100

(R)—N-(2-Chloro-4-(morpholin-2-yl)phenyl)-5-cyanopicolinamide hydrochloride

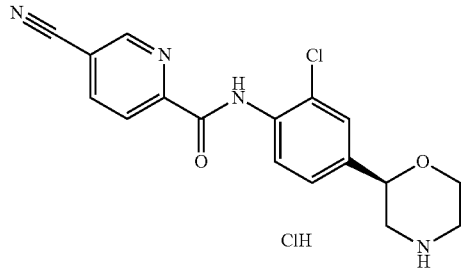 [SMILES: N#Cc1ccc(C(=O)Nc2ccc([C@@H]3CNCCO3)cc2Cl)nc1 ; Cl]

In analogy to example 79, step a) using 5-cyano-2-pyridinecarboxylic acid (CAS 53234-55-2) instead of 4-cyanopicolinic acid (CAS 640296-19-1) and (+)-(R)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 101

(S)—N-(2-Chloro-4-(morpholin-2-yl)phenyl)-6-cyanonicotinamide hydrochloride

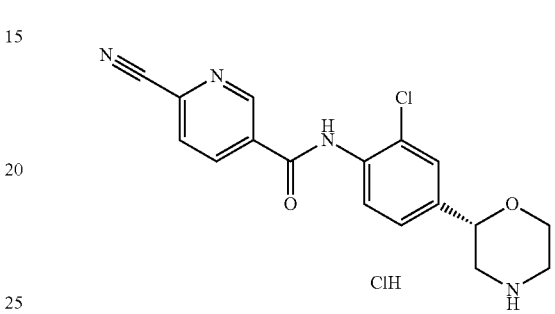

In analogy to example 79, step a) using 6-cyano-3-pyridinecarboxylic acid (CAS 70165-31-0) instead of 4-cyanopicolinic acid (CAS 640296-19-1) and (−)-(S)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 102

(R)—N-(2-Chloro-4-(morpholin-2-yl)phenyl)-6-cyanonicotinamide hydrochloride

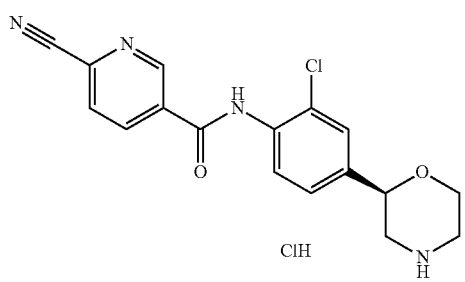 [SMILES: N#Cc1ccc(C(=O)Nc2ccc([C@@H]3CNCCO3)cc2Cl)cn1 ; Cl]

In analogy to example 79, step a) using 6-cyano-3-pyridinecarboxylic acid (CAS 70165-31-0) instead of 4-cyanopicolinic acid (CAS 640296-19-1) and (+)-(R)-2-(4-Amino-3-chloro-phenyl)-morpholine-4-carboxylic acid tert-butyl ester (example 29a) instead of (−)-(S)-2-(4-Amino-3-fluoro-phenyl)-morpholine-4-carboxylic acid tert-butyl ester. White solid. MS (ISP): 341.1 ([M+H]$^+$)

Example 103

(S)—N-(2-Chloro-4-(morpholin-2-yl)phenyl)-1-(4-cyanophenyl)-1H-pyrazole-4-carboxamide hydrochloride

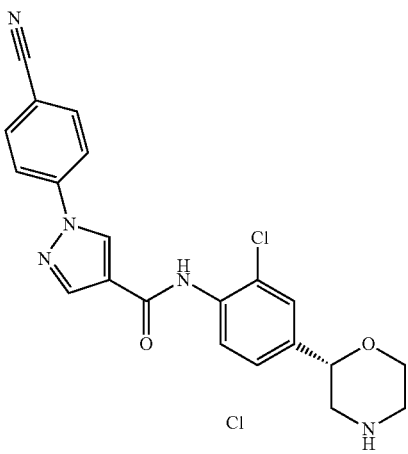 [SMILES: N#Cc1ccc(-n2cc(C(=O)Nc3ccc([C@H]4CNCCO4)cc3Cl)cn2)cc1 ; Cl]

In analogy to example 83, step a) using 1-(4-cyanophenyl)-1H-Pyrazole-4-carboxylic acid (CAS 1152945-21-5)) instead of 2-(trifluoromethyl)-4-pyridinecarboxylic acid (CAS 131747-41-6) and (−)-(S)-2-(4-Amino-3-chloro-phenyl)-morpholine-4-carboxylic acid tert-butyl ester (example 29a) instead of (+)-(R)-2-(4-Amino-2-fluoro-phenyl)-morpholine-4-carboxylic acid tert-butyl ester. White solid. MS (ISP): 408.2 ([M+H]$^+$)

Example 104

(S)-1-(4-(Difluoromethoxy)phenyl)-N-(2-fluoro-4-(morpholin-2-yl)phenyl)-1H-1,2,3-triazole-4-carboxamide

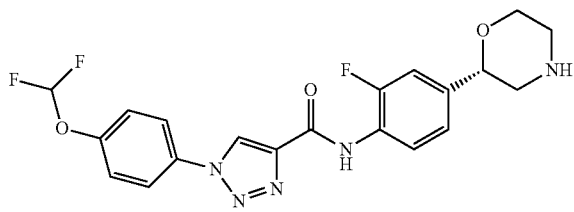 [SMILES: O=C(Nc1ccc([C@H]2CNCCO2)cc1F)c1cn(-c2ccc(OC(F)F)cc2)nn1]

a) Ethyl 1-(4-(difluoromethoxy)phenyl)-1H-1,2,3-triazole-4-carboxylate

In a 20 mL four-necked flask, 4-(difluoromethoxy)aniline (0.5 g, 3.14 mmol) and hydrochloric acid (37% in water, 0.54 ml, 6.6 mmol) were combined with water (5 ml) to give a light yellow solution. Cooled to 0° C. using an ice-bath, sodium nitrite (217 mg, 3.14 mmol) was dissolved in water (1 ml) and added carefully ensuring that the temperature did not increase above 5° C. Sodium azide (204 mg, 3.14 mmol) was dissolved in water (1 ml) and added drop-wise to the orange solution, keeping the temperature below 5° C. The reaction mixture was cooled at 0-5° C. for 1 hour and an orange emulsion was observed. The layers were separated using TBME and the organic layer was washed with brine, dried over sodium sulphate and filtered. The filtrate was concentrated under vacuum to yield 1-azido-4-(difluoromethoxy)benzene as an orange liquid.

In a 50 ml round-bottomed flask, 1-azido-4-(difluoromethoxy)benzene (540 mg, 2.92 mmol) was combined with THF (10 ml) and dimethylsulfoxide (0.16 ml) to give an orange solution. Then ethyl propiolate (858 mg, 0.89 ml, 8.75 mmol), copper (I) iodide (556 mg, 2.92 mmol) and 2,6-lutidine (625 mg, 0.68 ml, 5.83 mmol) were added and the reaction mixture was stirred for 2 hours at room temperature. Water and ethyl acetate were added and the layers were separated. The organic layer was washed with 1 N hydrochloric acid and brine, dried over MgSO$_4$ and filtered. The filtrate was concentrated under vacuum to yield a brown solid, which was adsorbed on silica gel and purified by flash chromatography (20 g Silica gel, 20% ethyl acetate in heptane) yielding 698 mg (84%) of a light yellow solid. MS (ISP): 284.2 ([M+H]$^+$).

b) 1-(4-(Difluoromethoxy)phenyl)-1H-1,2,3-triazole-4-carboxylic acid

To a solution of ethyl 1-(4-(difluoromethoxy)phenyl)-1H-1,2,3-triazole-4-carboxylate (600 mg, 2.12 mmol) in a mixture of THF (7 ml), methanol (7 ml) and water (7 ml) was added lithium hydroxide hydrate (267 mg, 6.36 mmol). The solution was heated to 70° C. for 3 h. Most of the organic solvent was removed under reduced pressure. Water was added and the solution was extracted with methyl tert-butyl ether to remove non-acid material. Then 25% aq. hydrochloric acid was added to reach acidic pH. The product precipitated and the mixture was extracted three times with ethyl acetate. The organic layers were combined, dried (MgSO$_4$) and evaporated to yield a light yellow solid (583 mg, 99%). MS (ISP): 253.9 ([M−H]$^+$); 509.2 ([2M−H]$^+$).

c) (S)-tert-butyl 2-(4-(1-(4-(difluoromethoxy)phenyl)-1H-1,2,3-triazole-4-carboxamido)-3-fluorophenyl)morpholine-4-carboxylate Under argon, 1-(4-(difluoromethoxy)phenyl)-1H-1,2,3-triazole-4-carboxylic acid (68.9 mg, 0.27 mmol) was suspended in dichloromethane (1.3 ml). Then 1-chloro-N,N''-trimethylpropenylamine (41.5 mg, 41 µl, 0.31 mmol) was added drop-wise and the reaction mixture was stirred for 15 minutes at room temperature to form the acid chloride.

(S)-tert-Butyl 2-(4-amino-3-fluorophenyl)morpholine-4-carboxylate (80 mg, 0.27 mmol) was dissolved in dichloromethane (1.3 ml). Ethyl diisopropylamine (87.2 mg, 112 µl, 0.675 mmol) was added. To this solution, the acid chloride was added drop-wise and the reaction mixture was stirred at room temperature for 3 hours.

The reaction mixture was extracted with dichloromethane and ammonium chloride solution; the organic phase was dried over MgSO4, filtered and concentrated in vacuo. The crude material was purified by flash chromatography (Silica gel, 10% to 30% EtOAc in heptane). The solid (100 mg) was recrystallized from ethyl acetate/heptane to yield a white solid (65 mg, 45%). MS (ISP): 478.1 (100%, [M−tBu+H]$^+$), 534.3 (10%, [M+H]$^+$).

d) (S)-1-(4-(Difluoromethoxy)phenyl)-N-(2-fluoro-4-(morpholin-2-yl)phenyl)-1H-1,2,3-triazole-4-carboxamide hydrochloride (S)-tert-Butyl 2-(4-(1-(4-(difluoromethoxy)phenyl)-1H-1,2,3-triazole-4-carboxamido)-3-fluorophenyl)morpholine-4- carboxylate (62 mg, 0.116 mmol) was dissolved in dioxane (0.6 ml) and a solution of HCl in dioxane (4M, 0.35 ml, 1.39 mmol) was added. The reaction mixture was stirred for 2 h at 60° C. After cooling ether was added, the solid was filtered off, washed with ether and dried in vacuo to afford (S)-1-(4-(difluoromethoxy)phenyl)-N-(2-fluoro-4-(morpholin-2-yl)phenyl)-1H-1,2,3-triazole-4-carboxamide hydrochloride (53 mg, 97%) as a white solid. MS (ISP): 434.4 ([M+H]$^+$).

Example 105

(S)—N-(3-Chloro-4-(morpholin-2-yl)phenyl)-1-(4-cyanophenyl)-1H-pyrazole-4-carboxamide hydrochloride

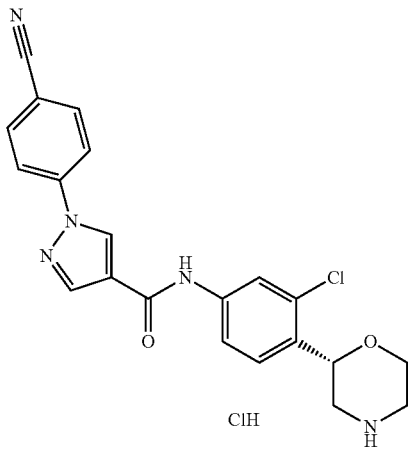 [SMILES: N#Cc1ccc(-n2cc(C(=O)Nc3ccc([C@H]4CNCCO4)c(Cl)c3)cn2)cc1 ; Cl]

In analogy to example 83, step a) using 1-(4-cyanophenyl)-1H-Pyrazole-4-carboxylic acid (CAS 1152945-21-5) instead of 2-(trifluoromethyl)-4-pyridinecarboxylic acid (CAS 131747-41-6) and (−)-(S)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester. Yellow solid. MS (ISP): 408.2 ([M+H]$^+$)

Example 106

(S)-4-Chloro-6-cyano-N-(2-fluoro-4-(morpholin-2-yl)phenyl)picolinamide hydrochloride

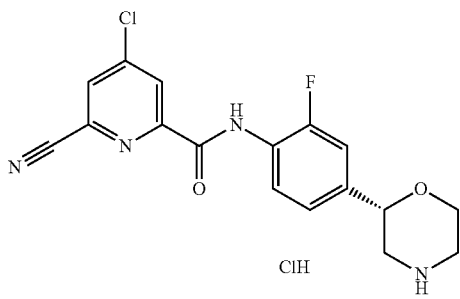 [SMILES: N#Cc1cc(Cl)cc(C(=O)Nc2ccc([C@H]3CNCCO3)cc2F)n1 ; Cl]

In analogy to Example 83, step a) using 4-chloro-6-cyano-2-pyridine carboxylic acid (CAS 1060812-13-6) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (example 1 step h) instead of (+)-(R)-2-(4-Amino-2-fluoro-phenyl)-morpholine-4-carboxylic acid tert-butyl ester. White solid. MS (ISP): 359.1 ([M+H]$^+$)

Example 107

(S)-2-Cyano-N-(3-fluoro-4-(morpholin-2-yl)phenyl)-6-methoxyisonicotinamide hydrochloride

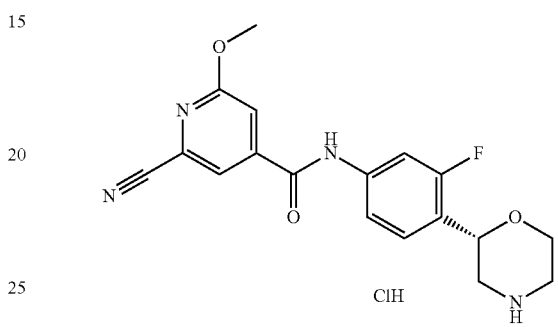

In analogy to Example 83, step a) using 2-Cyano-6-methoxy-isonicotinic acid instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester instead of (+)-(R)-2-(4-Amino-2-fluoro-phenyl)-morpholine-4-carboxylic acid tert-butyl ester. White solid. MS (ISP): 357.1 ([M+H]$^+$)

Preparation of 2-Cyano-6-methoxy-isonicotinic acid a) Methyl 2-cyano-6-methoxyisonicotinate Under N2, methyl 2-chloro-6-methoxyisonicotinate (CAS 42521-10-8) (3.97 g, 19.7 mmol, Eq: 1.00), zinc cyanide (2.77 g, 23.6 mmol, Eq: 1.2) and Tetrakis-triphenylphosphin-palladium (1.14 g, 985 μmol, Eq: 0.05) were mixed in DMF (67.5 ml). The RM was stirred under microwave at 160° C. for 30 minutes. Control with LC-MS: the reaction was finished.

The RM was partitioned between EtOAc and water; extracted; the organic phase was dried over MgSO4; filtered; concentrated in vacuo. The crude material was purified by flash chromatography (silica gel, 300 g, 5% to 30% EtOAc in heptane) leading to 2.48 g (66%) of desired product. Light yellow solid. MS (ISP): 193.1 ([M+H]$^+$)

b) 2-Cyano-6-methoxy-isonicotinic acid

Under N2, methyl 2-cyano-6-methoxyisonicotinate (0.433 g, 2.25 mmol, Eq: 1.00) was dissolved in THF (25.0 ml) and Methanol (3.03 ml). At 0° C., 1M LiOH in H2O (2.82 ml, 2.82 mmol, Eq: 1.25) was added and the RM was stirred at 0° C. for 30 minutes. Control with TLC: the reaction was finished. The reaction mixture was acidified with 1M HCl. The mixture was diluted with H2O and extracted with EtOAc. The organic phase was dried over MgSO4; filtered; concentrated in vacuo. Light yellow solid. MS (EIC): 176.8 ([M−H]$^-$)

Example 108

(S)-1-(4-Cyano-2-fluorophenyl)-N-(3-fluoro-4-(morpholin-2-yl)phenyl)-1H-pyrazole-4-carboxamide hydrochloride

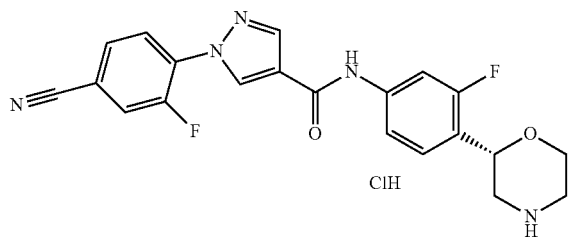 [SMILES: N#Cc1ccc(-n2cc(C(=O)Nc3ccc([C@H]4CNCCO4)c(F)c3)cn2)c(F)c1 ; Cl]

In analogy to example 79, step a) using 1-(4-Cyano-2-fluoro-phenyl)-1H-pyrazole-4-carboxylic acid (CAS 1283184-05-3) instead of 4-cyanopicolinic acid (CAS 640296-19-1) and (−)-(S)-2-(4-Amino-2-fluoro-phenyl)-morpholine-4-carboxylic acid tert-butyl ester (prepared in example 83) instead of (−)-(S)-2-(4-Amino-3-fluoro-phenyl)-morpholine-4-carboxylic acid tert-butyl ester. Step b) Instead of THF, Dioxane was used and the reaction mixture stirred for 2 hours at room temperature. Then 5 ml dioxane was added, the suspension stirred for 5 min, filtered off and the solid residue washed with ether and dried under high vacuo. Off-white solid. MS (ISP): 410.3 ([M+H—Cl]$^+$)

Example 109

(S)—N-(3-Chloro-4-(morpholin-2-yl)phenyl)-1-(4-cyano-2-fluorophenyl)-1H-pyrazole-4-carboxamide hydrochloride

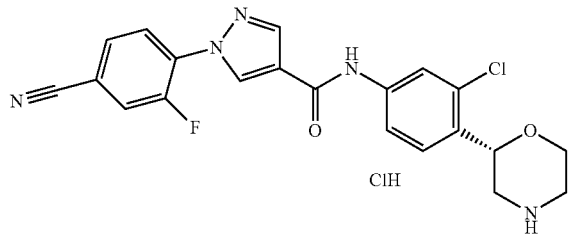 [SMILES: N#Cc1ccc(-n2cc(C(=O)Nc3ccc([C@H]4CNCCO4)c(Cl)c3)cn2)c(F)c1 ; Cl]

In analogy to example 79, step a) using 1-(4-Cyano-2-fluoro-phenyl)-1H-pyrazole-4-carboxylic acid (CAS 1283184-05-3) instead of 4-cyanopicolinic acid (CAS 640296-19-1) and (−)-(S)-2-(4-Amino-2-chloro-phenyl)-morpholine-4-carboxylic acid tert-butyl ester (prepared in example 91) instead of (−)-(S)-2-(4-Amino-3-fluoro-phenyl)-morpholine-4-carboxylic acid tert-butyl ester.

Step b) Instead of THF, Dioxane was used and the reaction mixture stirred for 2 hours at room temperature. Then 5 ml dioxane was added, the suspension stirred for 5 min, filtered off and the solid residue washed with ether and dried under high vacuo. Off-white solid. MS (ISP): 426.2 ([M+H—Cl]$^+$)

Example 110

(S)-1-(4-Cyano-2-fluorophenyl)-N-(2-fluoro-4-(morpholin-2-yl)phenyl)-1H-pyrazole-4-carboxamide hydrochloride

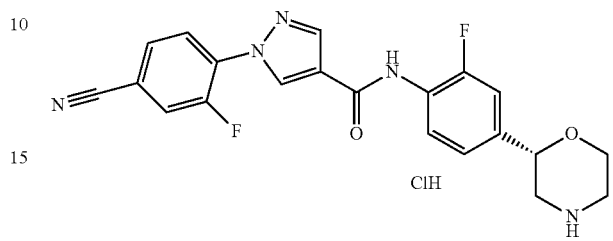

In analogy to example 79, step a) using 1-(4-Cyano-2-fluoro-phenyl)-1H-pyrazole-4-carboxylic acid (CAS 1283184-05-3) instead of 4-cyanopicolinic acid (CAS 640296-19-1). Step b) Instead of THF, Dioxane was used and the reaction mixture stirred for 2 hours at room temperature. Then 5 ml dioxane was added, the suspension stirred for 5 min, filtered off and the solid residue washed with ether and dried under high vacuo. Off-white solid. MS (ISP): 410.3 ([M+H—Cl]$^+$)

Example 111

(S)-1-(4-Cyanophenyl)-N-(2-fluoro-4-(morpholin-2-yl)phenyl)-1H-pyrazole-4-carboxamide hydrochloride

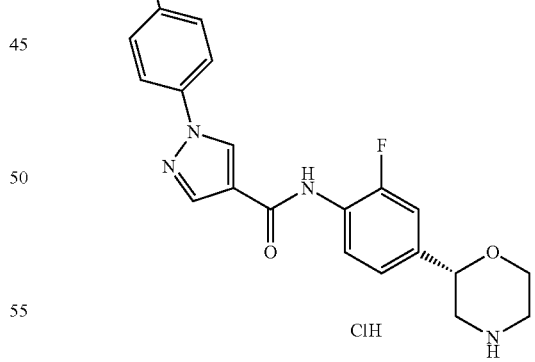

In analogy to example 83, step a) using 1-(4-cyanophenyl)-1H-Pyrazole-4-carboxylic acid (CAS 1152945-21-5) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (preparation described in example 1-h) instead of (+)-(R)-2-(4-Amino-2-fluoro-phenyl)-morpholine-4-carboxylic acid tert-butyl ester. Yellow solid. MS (ISP): 390.3 ([M−H]$^+$)

Example 112

(S)—N-(3-Chloro-4-(morpholin-2-yl)phenyl)-2-cyano-6-methylisonicotinamide hydrochloride

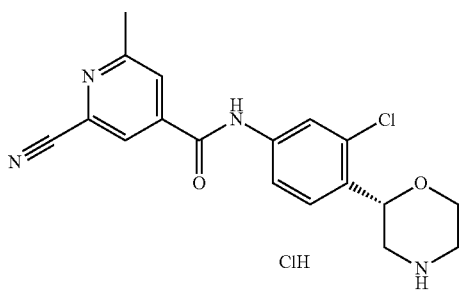 [SMILES: Cc1cc(C(=O)Nc2ccc([C@H]3CNCCO3)c(Cl)c2)cc(C#N)n1 ; Cl]

In analogy to example 83, step a) using 2-Cyano-6-methyl-isonicotinic acid instead of 2-(trifluoromethyl)-4-pyridinecarboxylic acid (CAS 131747-41-6) and (−)-(S)-2-(4-Amino-2-chloro-phenyl)-morpholine-4-carboxylic acid tert-butyl ester (preparation described in example 91) instead of (+)-(R)-2-(4-Amino-2-fluoro-phenyl)-morpholine-4-carboxylic acid tert-butyl ester.

Step b) 2 h at r.t. instead of 60° C. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Yellow foam. MS (ISP): 357.1 ([M+H]$^+$)

Preparation of 2-Cyano-6-methyl-isonicotinic acid a) Methyl 2-cyano-6-methylisonicotinate Under N2, methyl 2-chloro-6-methylisonicotinate (CAS 3998-90-1) (1.000 g, 5.39 mmol, Eq: 1.00), zinc cyanide (759 mg, 6.47 mmol, Eq: 1.2) and Tetrakis-triphenylphosphin-palladium (623 mg, 539 μmol, Eq: 0.1) were mixed in DMF (17 ml). The RM was stirred under microwave at 160° C. for 30 minutes. Control with TLC: the reaction was finished. The RM was partitioned between EtOAc and water; extracted; the organic phase was dried over MgSO4; filtered; concentrated in vacuo. The crude material was purified by flash chromatography (silica gel, 100 g, 5% to 30% EtOAc in heptane). Purple solid. MS (ISP): 177.2 ([M+H]$^+$)

b) Under N2, methyl 2-cyano-6-methylisonicotinate (0.490 g, 2.78 mmol, Eq: 1.00) was dissolved in Tetrahydrofuran (25 ml) and Methanol (3.03 ml). At 0° C., 1M LiOH in H2O (3.48 ml, 3.48 mmol, Eq: 1.25) was added and the RM was stirred at 0° C. for 30 minutes. Control with TLC: the reaction was finished. The reaction mixture was acidified with 1M HCl. The mixture was diluted with H2O and extracted with EtOAc. The organic phase was dried over MgSO4; filtered; concentrated in vacuo. Pink solid. MS (EIC): 160.8 ([M+H]$^+$)

Example 113

(S)-2-Cyano-N-(2-fluoro-4-(morpholin-2-yl)phenyl)-6-methylisonicotinamide hydrochloride

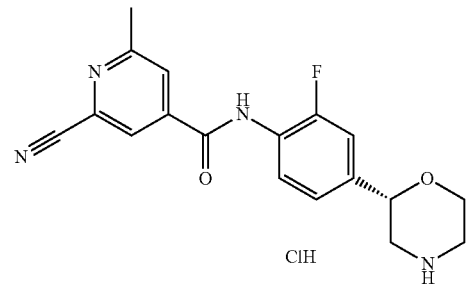 [SMILES: Cc1cc(C(=O)Nc2ccc([C@H]3CNCCO3)cc2F)cc(C#N)n1 ; Cl]

In analogy to example 83, step a) using 2-Cyano-6-methyl-isonicotinic acid (described in example 112) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (preparation described in example 1-h) instead of (+)-(R)-2-(4-Amino-2-fluoro-phenyl)-morpholine-4-carboxylic acid tert-butyl ester.

Step b) 2 h at r.t. instead of 60° C. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Yellow gum. MS (ISP): 341.1 ([M+H]$^+$)

Example 114

(S)—N4-(3-Fluoro-4-(morpholin-2-yl)phenyl)-6-methylpyridine-2,4-dicarboxamide hydrochloride

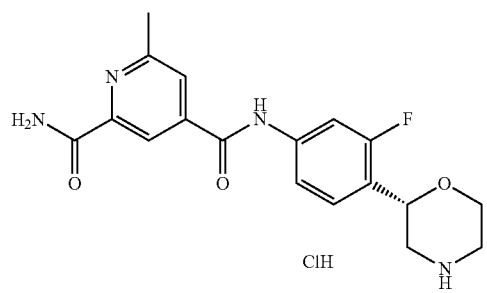 [SMILES: Cc1cc(C(=O)Nc2ccc([C@H]3CNCCO3)c(F)c2)cc(C(N)=O)n1 ; Cl]

Obtained as a side product of example 115 during the deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

Example 115

(S)-2-Cyano-N-(3-fluoro-4-(morpholin-2-yl)phenyl)-6-methylisonicotinamide hydrochloride

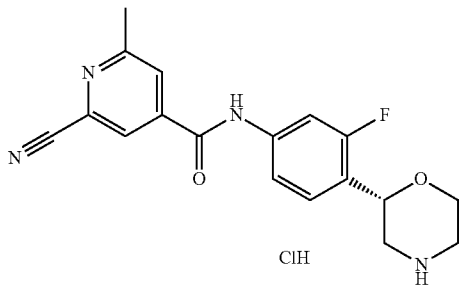 [SMILES: Cc1cc(C(=O)Nc2ccc([C@H]3CNCCO3)c(F)c2)cc(C#N)n1 ; Cl]

In analogy to example 83, step a) using 2-Cyano-6-methylisonicotinic acid (described in example 112) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester.

Step b) 2 h at r.t. instead of 60° C. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Yellow foam. MS (ISP): 341.1 ([M+H]$^+$)

Example 116

(S)-6-Chloro-N4-(3-fluoro-4-(morpholin-2-yl)phenyl)pyridine-2,4-dicarboxamide hydrochloride

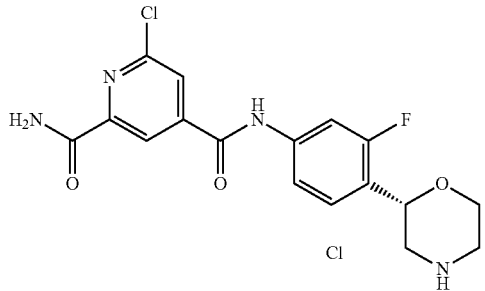 [SMILES: NC(=O)c1cc(C(=O)Nc2ccc([C@H]3CNCCO3)c(F)c2)cc(Cl)n1 ; Cl]

In analogy to example 83, step a) using 2-chloro-6-Cyano-4-pyridinecarboxylic acid (CAS 1060812-14-7) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester.

Step b) 2 h at r.t. instead of 60° C.

Formed as a side product of deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. White solid. MS (ISP): 379.2 ([M+H]$^+$)

Example 117

(S)-6-Ethyl-N4-(3-fluoro-4-(morpholin-2-yl)phenyl)pyridine-2,4-dicarboxamide hydrochloride

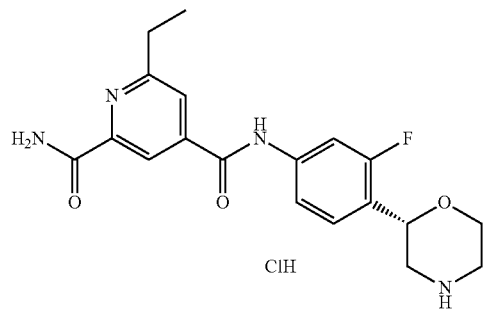 [SMILES: CCc1cc(C(=O)Nc2ccc([C@H]3CNCCO3)c(F)c2)cc(C(N)=O)n1 ; Cl]

In analogy to example 83, step a) using 2-ethyl-6-cyano-4-pyridinecarboxylic acid instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester.

Step b) 2 h at r.t. instead of 60° C.

Formed as a side product of deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo.

Light yellow solid. MS (ISP): 373.1 ([M+H]$^+$)

Preparation of 2-ethyl-6-cyano-4-pyridinecarboxylic acid a) 2-Ethyl-4-(methoxycarbonyl)pyridine 1-oxide Under N2, methyl 2-chloroisonicotinate (CAS 58481-11-1) (1.000 g, 5.83 mmol, Eq: 1.00) was dissolved in THF (35.0 ml) and NMP (4.00 ml). Iron III acetylacetonate (106 mg, 291 μmol, Eq: 0.05) (red solution) was added. At 0° C., ethylmagnesium bromide 1M in THF (11.7 ml, 11.7 mmol, Eq: 2) was added dropwise. The RM became dark brown. The RM was stirred at RT over 30 minutes. Control with TLC: the reaction was finished. 50 ml sat. NH4Cl-solution and 10 ml water were added. The RM was extracted. The water layer was extracted with DCM. The combined organics layers were dried over MgSO4; filtered; concentrated in vacuo (200 mbar). The crude material was purified by flash chromatography (silica gel, 70 g, DCM).

Under N2, the residue was diluted in DCM (20 ml). m-CPBA (1.51 g, 8.74 mmol, Eq: 1.50) was added and the RM was stirred at RT overnight. Control with TLC: the reaction was finished. The solvent was evaporated. The crude material was purified by flash chromatography (silica gel, 100 g, 35% to 100% EtOAc in heptane; then DCM; then MeOH). Brown oil. MS (ISP): 182.1 ([M+H]+)

b) Methyl 2-cyano-6-ethylisonicotinate

Under N2, 2-ethyl-4-(methoxycarbonyl)pyridine 1-oxide (0.165 g, 911 µmol, Eq: 1.00) was dissolved in Acetonitrile (4 ml). Dimethylcarbamylchloride (108 mg, 92.1 µl, 1.00 mmol, Eq: 1.1), triethylamine (175 mg, 239 µl, 1.73 mmol, Eq: 1.9) and Trimethylsilylcyanid (280 mg, 355 µl, 2.82 mmol, Eq: 3.10) were added and the RM was stirred at 90° C. overnight. The RM became an orange solution. Control with TLC: the reaction was finished. At RT, the RM was partitioned between water and EtOAc. The organic phase was dried over MgSO4; filtered; concentrated in vacuo: 350 mg; NMR: T205185. The crude material was purified by flash chromatography (silica gel, 20 g, 5% to 50% EtOAc in heptane). Light yellow oil.

c) 2-ethyl-6-cyano-4-pyridinecarboxylic acid

Under N2, methyl 2-cyano-6-ethylisonicotinate (0.233 g, 1.23 mmol, Eq: 1.00) was diluted in THF (12.1 ml) and MeOH (1.46 ml). At 2-3° C., 1M LiOH in water (1.53 ml, 1.53 mmol, Eq: 1.25) was added dropwise (over 3 min) The RM was stirred at 2-3° C. for 30 minutes. Control with TLC: the reaction was finished. The reaction mixture was acidified with 1M HCl. The mixture was diluted with H2O and extracted with EtOAc. The organic phase was dried over MgSO4; filtered; concentrated in vacuo. White solid. MS (EIC): 174.9 ([M−H]−)

Example 118

(S)—N4-(3-Chloro-4-(morpholin-2-yl)phenyl)-6-methylpyridine-2,4-dicarboxamide hydrochloride

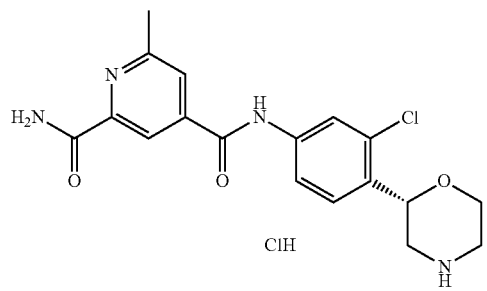 [SMILES: Cc1cc(C(=O)Nc2ccc([C@H]3CNCCO3)c(Cl)c2)cc(C(N)=O)n1 ; Cl]

Formed as a side product of example 112, deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Off-white solid. MS (ISP): 375.1 ([M+H]+)

Example 119

(S)—N4-(2-Fluoro-4-(morpholin-2-yl)phenyl)-6-methylpyridine-2,4-dicarboxamide hydrochloride

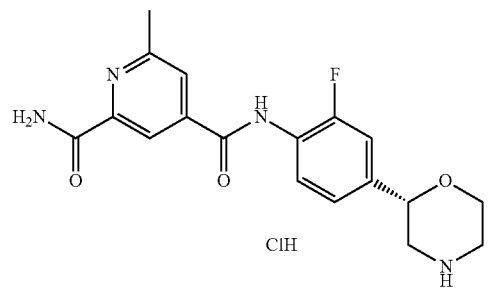 [SMILES: Cc1cc(C(=O)Nc2ccc([C@H]3CNCCO3)cc2F)cc(C(N)=O)n1 ; Cl]

In analogy to example 83, step a) using 2-Cyano-6-methyl-isonicotinic acid instead (described in example 112) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (described in example 1 h) instead of (+)-(R)-2-(4-Amino-2-fluoro-phenyl)-morpholine-4-carboxylic acid tert-butyl ester.

Step b) 2 h at r.t. instead of 60° C.

Formed as a side product of deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo.

Light yellow solid. MS (ISP): 359.1 ([M+H]+)

Example 120

(S)—N4-(2-Fluoro-4-(morpholin-2-yl)phenyl)-6-methoxypyridine-2,4-dicarboxamide hydrochloride

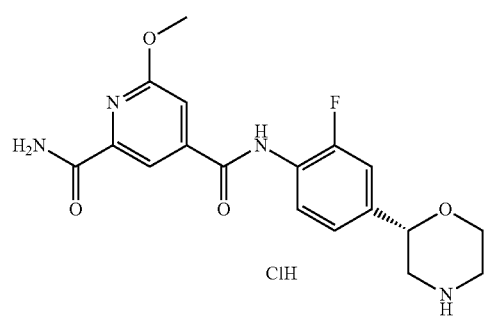 [SMILES: COc1cc(C(=O)Nc2ccc([C@H]3CNCCO3)cc2F)cc(C(N)=O)n1 ; Cl]

Formed as a side product of deprotection step (step b) in example 121. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. White foam. MS (ISP): 375.1 ([M+H]$^+$)

Example 121

(S)-2-Cyano-N-(2-fluoro-4-(morpholin-2-yl)phenyl)-6-methoxyisonicotinamide hydrochloride

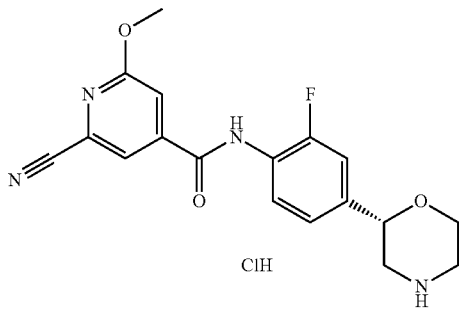 [SMILES: COc1cc(C(=O)Nc2ccc([C@H]3CNCCO3)cc2F)cc(C#N)n1 ; Cl]

In analogy to example 83, step a) using 2-Cyano-6-methoxy-isonicotinic acid (described in example 107) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (described in example 1 h) instead of (+)-(R)-2-(4-Amino-2-fluoro-phenyl)-morpholine-4-carboxylic acid tert-butyl ester.

Step b) 2 h at r.t. instead of 60° C.

Formed as the main product of deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo.

White solid. MS (ISP): 357.1 ([M+H]$^+$)

Example 122

(S)—N4-(2-Chloro-4-(morpholin-2-yl)phenyl)-6-methylpyridine-2,4-dicarboxamide hydrochloride

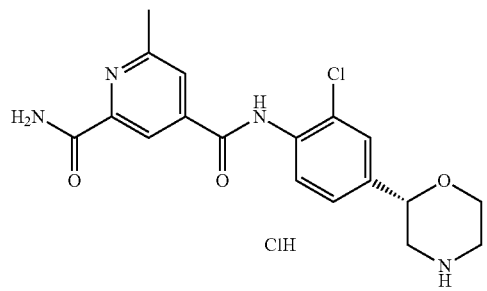 [SMILES: Cc1cc(C(=O)Nc2ccc([C@H]3CNCCO3)cc2Cl)cc(C(N)=O)n1 ; Cl]

Formed as a side product of deprotection step (step b) in example 123. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.) The pure fractions were concentrated and the residue was dissolved in ether, acidified with 1M HCl in ether; filtered off and dried in high vacuo. Yellow solid. MS (ISP): 375.1 ([M+H]$^+$)

Example 123

(S)—N-(2-Chloro-4-(morpholin-2-yl)phenyl)-2-cyano-6-methylisonicotinamide hydrochloride

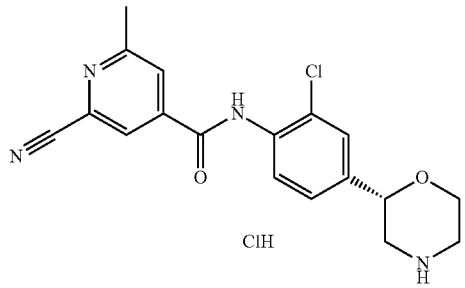 [SMILES: Cc1cc(C(=O)Nc2ccc([C@H]3CNCCO3)cc2Cl)cc(C#N)n1 ; Cl]

In analogy to example 83, step a) using 2-Cyano-6-methylisonicotinic acid (described in example 112) instead of 2-(trifluoromethyl)-4-pyridinecarboxylic acid (CAS 131747-41-6) and (−)-(S)-2-(4-Amino-3-chloro-phenyl)-morpholine-4-carboxylic acid tert-butyl ester (described in example 29a) instead of (+)-(R)-2-(4-Amino-2-fluoro-phenyl)-morpholine-4-carboxylic acid tert-butyl ester.

Step b) 2 h at r.t. instead of 60° C.

Formed as the main product of deprotection step (step b). The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Yellow gum. MS (ISP): 357.1 ([M+H]$^+$)

Example 124

(S)—N-(2-Chloro-4-(morpholin-2-yl)phenyl)-2-cyano-6-methoxyisonicotinamide hydrochloride

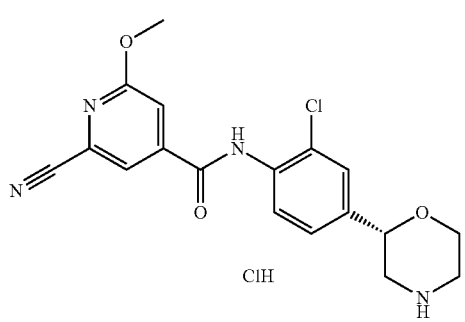 [SMILES: COc1cc(C(=O)Nc2ccc([C@H]3CNCCO3)cc2Cl)cc(C#N)n1 ; Cl]

In analogy to example 83, step a) using 2-Cyano-6-methoxy-isonicotinic acid (described in example 107) instead of 2-(trifluoromethyl)-4-pyridinecarboxylic acid (CAS 131747-41-6) and (−)-(S)-2-(4-Amino-3-chloro-phenyl)-morpholine-4-carboxylic acid tert-butyl ester (described in example 29a) instead of (+)-(R)-2-(4-Amino-2-fluoro-phenyl)-morpholine-4-carboxylic acid tert-butyl ester.

Step b) 2 h at r.t. instead of 60° C. The reaction mixture was extracted with EtOAc/0.5M Na2CO3; the organic layers were dried with MgSO4; filtered-off and concentrated in vacuo. The residue was chromatographed (preparative HPLC) using following conditions: column Gemini NX C18 5u 110A (100×30 mm), eluent A: H2O+0.1% Et3N B: gradient 20% B à 100% B in 12 min. flow: 40 ml/min, r.t.)

The pure fractions were concentrated and the residue was dissolved in ether, acidified with 1M HCl in ether; filtered off and dried in high vacuo. Off white foam. MS (ISP): 373.0 ([M+H]+)

Example 125

(S)—N-(2-Fluoro-4-(morpholin-2-yl)phenyl)-1-(6-(trifluoromethyl)pyrazin-2-yl)-1H-pyrazole-4-carboxamide hydrochloride

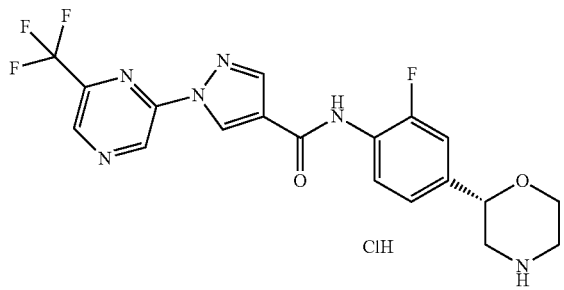 [SMILES: O=C(Nc1ccc([C@H]2CNCCO2)cc1F)c1cnn(-c2cncc(C(F)(F)F)n2)c1 ; Cl]

In analogy to example 83, step a) using 1-(6-Trifluoromethyl-pyrazin-2-yl)-1H-pyrazole-4-carboxylic acid instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (described in example 1 h) instead of (+)-(R)-2-(4-Amino-2-fluoro-phenyl)-morpholine-4-carboxylic acid tert-butyl ester.

Step b) 3 h instead of 2 h at 60° C. White solid. MS (ISP): 437.2 ([M+H]+)

Preparation of 1-(6-Trifluoromethyl-pyrazin-2-yl)-1H-pyrazole-4-carboxylic acid a) Ethyl 1-(6-(trifluoromethyl)pyrazin-2-yl)-1H-pyrazole-4-carboxylate Under N2, 2-iodo-6-(trifluoromethyl)pyrazine (CAS 141492-94-6) (0.137 g, 500 μmol, Eq: 1.00), ethyl 1H-pyrazole-4-carboxylate (CAS 37622-90-5) (70.1 mg, 500 μmol, Eq: 1.00) and potassium carbonate (138 mg, 1.00 mmol, Eq: 2) were combined in DMSO (2.4 ml). The orange solution was stirred at 120° C. over 1 hour. Control with TLC: the reaction was finished. At RT, the RM was partitioned between water and EtOAc; extracted; the organic layer was washed with water and brine; dried over MgSO4; filtered; concentrated in vacuo. The crude material was purified by flash chromatography (silica gel, 20 g, 5% to 25% EtOAc in heptane).

b) 1-(6-Trifluoromethyl-pyrazin-2-yl)-1H-pyrazole-4-carboxylic acid

Under N2, ethyl 1-(6-(trifluoromethyl)pyrazin-2-yl)-1H-pyrazole-4-carboxylate (155 mg, 542 μmol, Eq: 1.00) was dissolved in DMF (9.3 ml) and Water (9.3 ml). Potassium carbonate (150 mg, 1.08 mmol, Eq: 2) was added and the RM was stirred at 70° C. overnight. Control with LC-MS: Pr/SM: 74/26. Potassium carbonate (150 mg, 1.08 mmol, Eq: 2) was added and the RM was stirred at 70° C. overnight. Control with LC-MS: SM/Pr:4/96. At RT, the RM was partitioned between 1M K2CO3 and EtOAc; extracted; the water layer was acidified with 1M HCl; extracted with EtOAc; the organic phase was dried over MgSO4; filtered; concentrated in vacuo leading to 132 mg off-white solid.

Example 126

(S)—N-(2-Chloro-4-(morpholin-2-yl)phenyl)-1-(6-(trifluoromethyl)pyrazin-2-yl)-1H-pyrazole-4-carboxamide hydrochloride

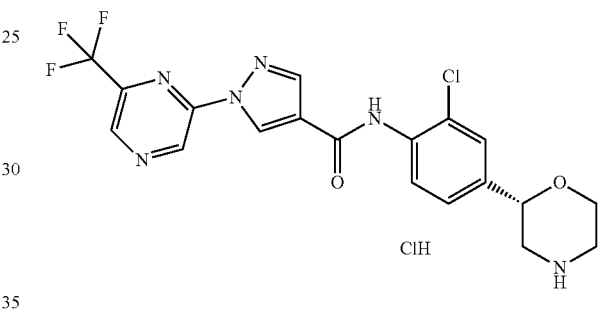

In analogy to example 83, step a) using 1-(6-Trifluoromethyl-pyrazin-2-yl)-1H-pyrazole-4-carboxylic acid (prepared as described in example 125) instead of 2-(trifluoromethyl)-4-pyridinecarboxylic acid (CAS 131747-41-6) and (−)-(S)-2-(4-Amino-3-chloro-phenyl)-morpholine-4-carboxylic acid tert-butyl ester (described in example 29a) instead of (+)—(R)-2-(4-Amino-2-fluoro-phenyl)-morpholine-4-carboxylic acid tert-butyl ester.

Step b) 3 h instead of 2 h at 60° C. Light yellow solid. MS (ISP): 453.2 ([M+H]+)

Example 127

(S)—N-(3-Fluoro-4-(morpholin-2-yl)phenyl)-1-(6-(trifluoromethyl)pyrazin-2-yl)-1H-pyrazole-4-carboxamide hydrochloride

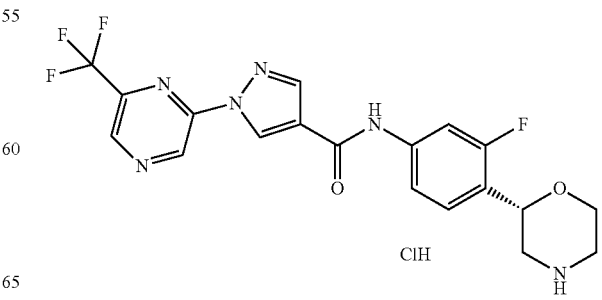

In analogy to example 83, step a) using 1-(6-Trifluoromethyl-pyrazin-2-yl)-1H-pyrazole-4-carboxylic acid (prepared as described in example 125) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)—(R)-2-(4-Amino-2-fluoro-phenyl)-morpholine-4-carboxylic acid tert-butyl ester.

Step b) 3 h instead of 2 h at 60° C. White solid. MS (ISP): 437.2 ([M+H]+)

Example 128

(S)—N-(3-Chloro-4-(morpholin-2-yl)phenyl)-1-(6-(trifluoromethyl)pyrazin-2-yl)-1H-pyrazole-4-carboxamide hydrochloride

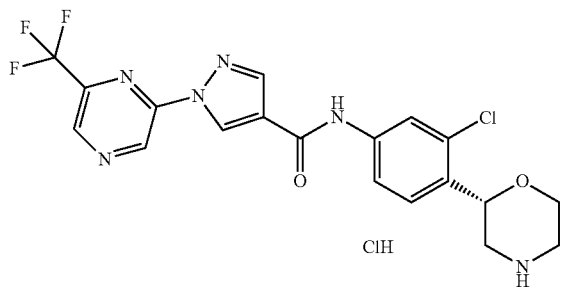 [SMILES: O=C(Nc1ccc([C@H]2CNCCO2)c(Cl)c1)c1cnn(-c2cncc(C(F)(F)F)n2)c1 ; Cl]

In analogy to example 83, step a) using 1-(6-Trifluoromethyl-pyrazin-2-yl)-1H-pyrazole-4-carboxylic acid (prepared as described in example 125) instead of 2-(trifluoromethyl)-4-pyridinecarboxylic acid (CAS 131747-41-6) and (−)-(S)-2-(4-Amino-2-chloro-phenyl)-morpholine-4-carboxylic acid tert-butyl ester (described in example 91) instead of (+)—(R)-2-(4-Amino-2-fluoro-phenyl)-morpholine-4-carboxylic acid tert-butyl ester.

Step b) 3 h instead of 2 h at 60° C. White solid. MS (ISP): 453.2 ([M+H]+)

Example 129

(S)—N-(3-Fluoro-4-(morpholin-2-yl)phenyl)-1-(6-(trifluoromethyl)pyrimidin-4-yl)-1H-pyrazole-4-carboxamide hydrochloride

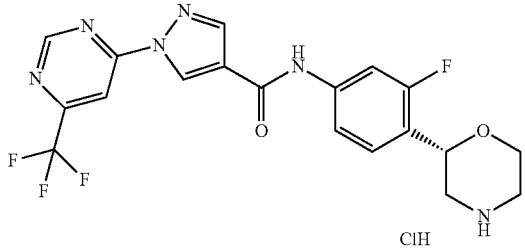 [SMILES: O=C(Nc1ccc([C@H]2CNCCO2)c(F)c1)c1cnn(-c2cc(C(F)(F)F)ncn2)c1 ; Cl]

Step a) (S)-tert-butyl 2-(2-fluoro-4-(1H-pyrazole-4-carboxamido)phenyl)morpholine-4-carboxylate 1H-pyrazole-4-carboxylic acid (CAS 37718-11-9) (97.5 mg, 844 μmol, Eq: 1.00) was dissolved in methanol (6 ml). (S)-tert-butyl 2-(4-amino-2-fluorophenyl)morpholine-4-carboxylate (prepared as described in example 83) (0.250 g, 844 μmol, Eq: 1.00) was added. At 0° C., a solution of 4-(4,6-dimethoxy-1,3,5-triazin-2-yl)-4-methylmorpholin-4-ium chloride (303 mg, 1.1 mmol, Eq: 1.3) in Methanol (5 ml) was added over 1 hour. The RM was stirred at 50° C. over 3 hours. After cooling down to RT, the solvent was evaporated and the residue was purified by flash chromatography (silica gel, 50 g, 10% to 100% EtOAc in heptane). White solid (0.25 g, 74%). MS (EIC): 413.2 ([M+Na]+)

Step b) (S)-tert-butyl 2-(2-fluoro-4-(1-(6-(trifluoromethyl)pyrimidin-4-yl)-1H-pyrazole-4-carboxamido)phenyl)morpholine-4-carboxylate Under N2, (S)-tert-butyl 2-(2-fluoro-4-(1H-pyrazole-4-carboxamido)phenyl)morpholine-4-carboxylate (60 mg, 154 μmol, Eq: 1.00), 4-chloro-6-(trifluoromethyl)-pyrimidine (CAS 37552-81-1) (28 mg, 154 μmol, Eq: 1.00) and were combined in DMSO (2 ml). The orange solution was stirred at 120° C. over 1 hour. Control with TLC: the reaction was finished. At RT, the RM was partitioned between water and EtOAc; extracted; the organic layer was washed with water and brine; dried over MgSO4; filtered; concentrated in vacuo. The crude material was purified by flash chromatography (silica gel, 10 g, 15% to 60% EtOAC in heptane). Yellow solid (41 mg). MS: 535.7 ([M−H]−)

Step c) (S)—N-(3-fluoro-4-(morpholin-2-yl)phenyl)-1-(6-(trifluoromethyl)pyrimidin-4-yl)-1H-pyrazole-4-carboxamide hydrochloride In analogy to example 83, step b). White solid. MS (ISP): 453.2 ([M+H]+)

Example 130

(S)—N-(3-Fluoro-4-(morpholin-2-yl)phenyl)-1-(6-(trifluoromethyl)pyridin-3-yl)-1H-pyrazole-4-carboxamide hydrochloride

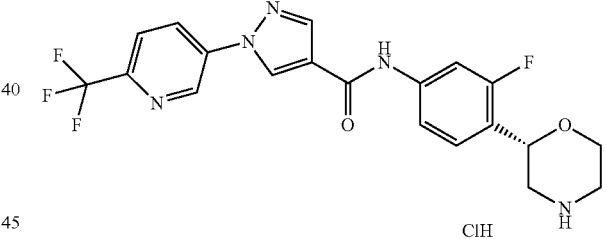

In analogy to example 129, step b) using 5-bromo-2-(trifluoromethyl)-pyridine (CAS 436799-92-5) instead of 4-chloro-6-(trifluoromethyl)-pyrimidine (CAS 37552-81-1) and heating 17 h (instead of 1 h) at 120° C. White solid. MS (ISP): 436.4 ([M+H]+)

Example 131

(S)-1-(5-Cyanopyrazin-2-yl)-N-(3-fluoro-4-(morpholin-2-yl)phenyl)-1H-pyrazole-4-carboxamide hydrochloride

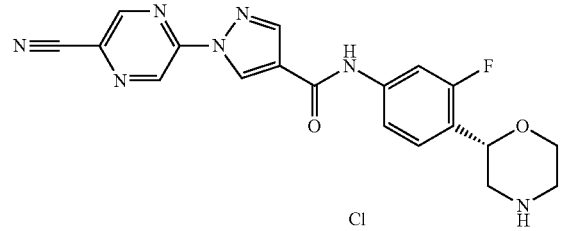 [SMILES: N#Cc1cnc(-n2cc(C(=O)Nc3ccc([C@H]4CNCCO4)c(F)c3)cn2)cn1 ; Cl]

In analogy to example 129, step b) using 5-bromo-2-Pyrazinecarbonitrile (CAS 221295-04-1) instead of 4-chloro-6-(trifluoromethyl)-pyrimidine (CAS 37552-81-1) and reaction being performed at r.t. (instead at 120° C.). White solid. MS (ISP): 394.4 ([M+H]+)

Example 132

(S)—N-(3-Fluoro-4-(morpholin-2-yl)phenyl)-1-(2-(trifluoromethyl)pyrimidin-4-yl)-1H-pyrazole-4-carboxamide hydrochloride

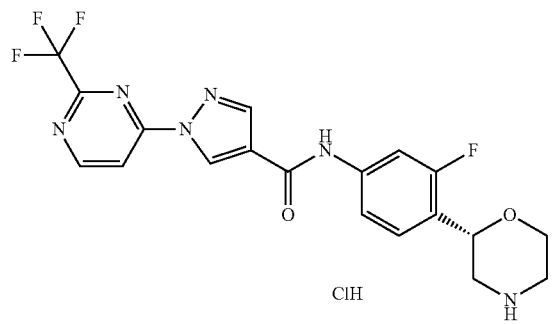 [SMILES: O=C(Nc1ccc([C@H]2CNCCO2)c(F)c1)c1cnn(-c2ccnc(C(F)(F)F)n2)c1 ; Cl]

In analogy to example 129, step b) using 4-chloro-2-(trifluoromethyl)-pyrimidine (CAS 1514-96-1) instead of 4-chloro-6-(trifluoromethyl)-pyrimidine (CAS 37552-81-1). White solid. MS (ISP): 419.5 ([M+H]+)

Example 133

(S)-4-Chloro-6-cyano-N-(3-fluoro-4-(morpholin-2-yl)phenyl)picolinamide hydrochloride

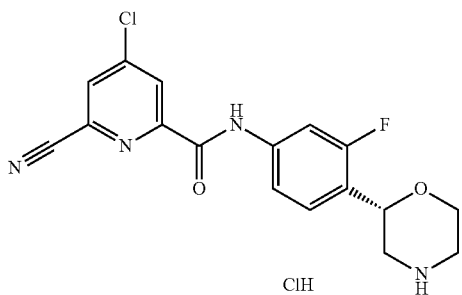 [SMILES: N#Cc1cc(Cl)cc(C(=O)Nc2ccc([C@H]3CNCCO3)c(F)c2)n1 ; Cl]

In analogy to example 83, step a) using 4-chloro-6-cyano-2-pyridine carboxylic acid (CAS 1060812-13-6) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester.
Step b) As described in example 79 step (b). White solid. MS (ISP): 361.1 ([M+H]+)

Example 134

(S)—N-(3-Fluoro-4-(morpholin-2-yl)phenyl)-1-(5-(trifluoromethyl)pyrazin-2-yl)-1H-pyrazole-4-carboxamide hydrochloride

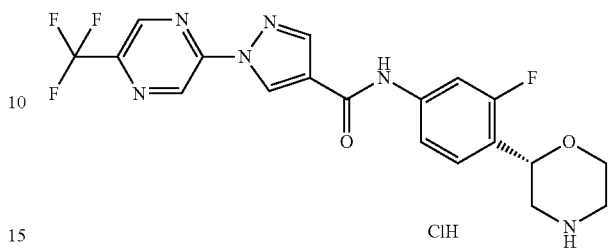

In analogy to example 129, step b) using 2-chloro-5-(trifluoromethyl)-pyrazine (CAS 799557-87-2) instead of 4-chloro-6-(trifluoromethyl)-pyrimidine (CAS 37552-81-1). White solid. MS (ISP): 435.0 ([M+H]+)

Example 135

(S)-5-Cyano-N-(2-fluoro-4-(morpholin-2-yl)phenyl)-6-methylpicolinamide hydrochloride

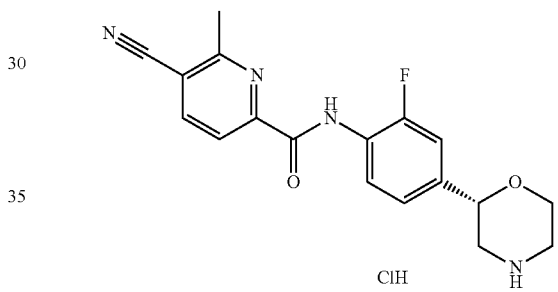

In analogy to example 83, step a) using 5-cyano-6-methyl-2-pyridinecarboxylic acid (CAS 855916-58-4) instead of 2-(trifluoromethyl)-4-pyridinecarboxylic acid (CAS 131747-41-6) and (−)-(S)-2-(4-Amino-3-fluoro-phenyl)-morpholine-4-carboxylic acid tert-butyl ester (described in example 1 h) instead of (+)-(R)-2-(4-Amino-2-fluoro-phenyl)-morpholine-4-carboxylic acid tert-butyl ester. White solid. MS (ISP): 340.9 ([M+H]+)

Example 136

(S)-5-Cyano-N-(3-fluoro-4-(morpholin-2-yl)phenyl)-6-methylpicolinamide hydrochloride

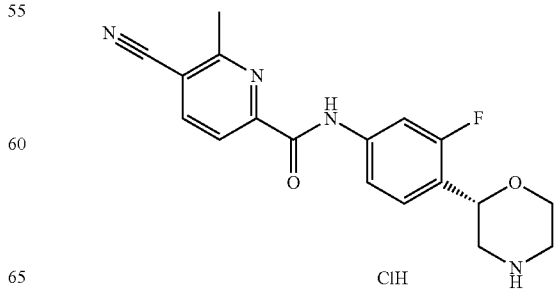

In analogy to example 83, step a) using 5-cyano-6-methyl-2-pyridinecarboxylic acid (CAS 855916-58-4) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester. White solid. MS (ISP): 340.9 ([M+H]$^+$)

Example 137

(S)—N-(3-Fluoro-4-(morpholin-2-yl)phenyl)-5-(trifluoromethyl)pyrazine-2-carboxamide hydrochloride

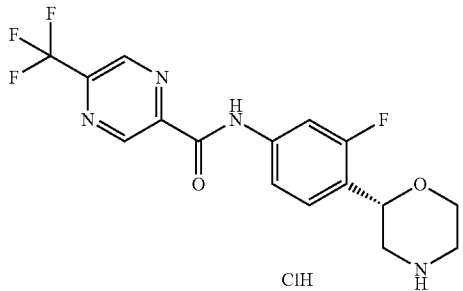 [SMILES: O=C(Nc1ccc([C@H]2CNCCO2)c(F)c1)c1cnc(C(F)(F)F)cn1 ; Cl]

In analogy to example 83, step a) using 5-(trifluoromethyl)-2-pyrazinecarboxylic acid (CAS 1060814-50-7) instead of 2-(trifluoromethyl)-4-pyridinecarboxylic acid (CAS 131747-41-6) and (−)-(S)-2-(4-Amino-2-fluoro-phenyl)-morpholine-4-carboxylic acid tert-butyl ester (described in example 83) instead of (+)-(R)-2-(4-Amino-2-fluoro-phenyl)-morpholine-4-carboxylic acid tert-butyl ester. White solid. MS (ISP): 370.9 ([M+H]$^+$)

Example 138

(S)-6-Ethoxy-N-(2-fluoro-4-(morpholin-2-yl)phenyl) nicotinamide

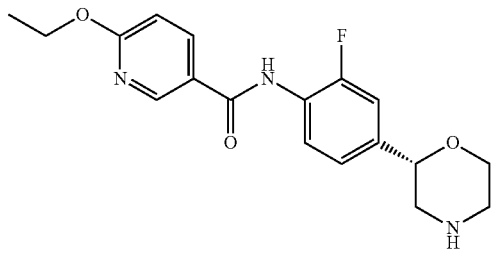 [SMILES: CCOc1ccc(C(=O)Nc2ccc([C@H]3CNCCO3)cc2F)cn1]

The title compound was obtained in analogy to example 23 using (−)-(S)-2-(4-amino-3-fluoro-phenyl)-morpholine-4-carboxylic acid tert-butyl ester in place of (+)-(R)-2-(4-amino-3-fluoro-phenyl)-morpholine-4-carboxylic acid tert-butyl ester and 6-ethoxy-nicotinic acid (CAS 97455-65-7) in place of 1-methyl-3-phenyl-1H-pyrazole-5-carboxylic acid in step (a). White solid. MS (ISP): 346.2 ([M+H]$^+$).

The compounds of formula I and their pharmaceutically usable addition salts possess valuable pharmacological properties. Specifically, compounds of the present invention have a good affinity to the trace amine associated receptors (TAARs), especially TAAR1.

The compounds were investigated in accordance with the test given hereinafter.

Materials and Methods

Construction of TAAR Expression Plasmids and Stably Transfected Cell Lines

For the construction of expression plasmids the coding sequences of human, rat and mouse TAAR 1 were amplified from genomic DNA essentially as described by Lindemann et al. [14]. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described by Lindemann et al. (2005). For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hrs post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Radioligand Binding Assay on Rat TAAR1

Membrane Preparation and Radioligand Binding.

HEK-293 cells stably expressing rat TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated K$_d$ value, that was usually around 2.3 nM, resulting in the binding of approximately 0.2% of the radioligand and a specific binding representing approximately 85% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×K$_d$ in nM and 500 µl of the membranes (resuspended at 50 µg protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

Radioligand Binding Assay on Mouse TAAR1

Membrane Preparation and Radioligand Binding.

HEK-293 cells stably expressing mouse TAAR1 were maintained at 37° C. and 5% CO$_2$ in DMEM high glucose medium, containing fetal calf serum (10%, heat inactivated for 30 min at 56° C.), penicillin/streptomycin (1%), and 375 µg/ml geneticin (Gibco). Cells were released from culture flasks using trypsin/EDTA, harvested, washed twice with ice-cold PBS (without Ca$^{2+}$ and Mg$^{2+}$), pelleted at 1'000 rpm for 5 min at 4° C., frozen and stored at −80° C. Frozen pellets were suspended in 20 ml HEPES-NaOH (20 mM, pH 7.4) containing 10 mM EDTA and homogenized with a Polytron (PT 6000, Kinematica) at 14'000 rpm for 20 s. The homogenate was centrifuged at 48'000×g for 30 min at 4° C. Subsequently, the supernatant was removed and discarded, and the pellet resuspended in 20 ml HEPES-NaOH (20 mM, pH 7.4) containing 0.1 mM EDTA using the Polytron (20 s at 14'000 rpm). This procedure was repeated and the final pellet resuspended in HEPES-NaOH containing 0.1 mM EDTA and homogenized using the Polytron. Typically, aliquots of 2 ml membrane portions were stored at −80° C. With each new membrane batch the dissociation constant (K$_d$) was determined via a saturation curve. The TAAR1 radioligand $^3$[H]-(S)-4-[(ethyl-phenyl-amino)-methyl]-4,5-dihydro-oxazol-2-ylamine (described in WO 2008/098857) was used at a concentration equal to the calculated K$_d$ value, that was usually around 0.7 nM, resulting in the binding of approximately 0.5% of the radioligand and a specific binding representing approximately 70% of the total binding. Nonspecific binding was defined as the amount of $^3$[H]-(S)-4-[(ethyl-phenyl-amino)-methyl]-4,5-dihydro-oxazol-2-ylamine bound in the presence of 10 µM unlabeled ligand. All compounds were tested at a broad range of concentrations (10 pM to 10 µM) in duplicates. The test compounds (20 µl/well) were transferred into a 96 deep well plate (TreffLab), and 180 µl of HEPES-NaOH (20 mM, pH 7.4) containing MgCl$_2$ (10 mM) and CaCl$_2$ (2 mM) (binding buffer), 300 µl of the radioligand $^3$[H]-(S)-4-[(ethyl-phenyl-amino)-methyl]-4,5-dihydro-oxazol-2-ylamine at a concentration of 3.3×K$_d$ in nM and 500 µl of the membranes (resuspended at 60 ng protein per ml) added. The 96 deep well plates were incubated for 1 hr at 4° C. Incubations were terminated by rapid filtration through Unifilter-96 plates (Packard Instrument Company) and glass filters GF/C (Perkin Elmer) presoaked for 1 hr in polyethylenimine (0.3%) and washed 3 times with 1 ml of cold binding buffer. After addition of 45 µl of Microscint 40 (PerkinElmer) the Unifilter-96 plate was sealed and after 1 hr the ratioactivity counted using a TopCount Microplate Scintillation Counter (Packard Instrument Company).

The compounds show a K$_i$ value (µM) in mouse or rat on TAAR1 (in µM) as shown in the table below.

| Example | Ki (µM) mouse/rat |
|---|---|
| 1 | 0.001/ 0.0051 |
| 2 | 0.0012/ 0.0009 |
| 3 | 0.0016/ 0.0015 |
| 4 | 0.0017/ 0.0028 |
| 5 | 0.0012/ 0.0013 |
| 6 | 0.0012/ 0.0017 |
| 7 | 0.0015/ 0.0016 |
| 8 | 0.0026/ 0.0039 |
| 9 | 0.0017/ 0.0105 |
| 10 | 0.0033/ 0.0033 |
| 11 | 0.0035/ 0.0095 |
| 12 | 0.0026/ 0.0006 |
| 13 | 0.0011/ 0.0024 |
| 14 | 0.0016/ 0.0039 |
| 15 | 0.0074/ 0.0544 |
| 16 | 0.0031/ 0.0679 |
| 17 | 0.0151/ 0.0128 |
| 18 | 0.0012/ 0.0033 |
| 19 | 0.0014/ 0.0034 |
| 20 | 0.0012/ 0.005 |
| 21 | 0.0032/ 0.0022 |
| 22 | 0.002/ 0.0036 |
| 23 | 0.0254/ 0.0033 |
| 24 | 0.0032/ 0.007 |
| 25 | 0.0034/ 0.0127 |
| 26 | 0.0012/ 0.002 |
| 27 | 0.0028/ 0.0038 |
| 28 | 0.014/ 0.0059 |
| 29 | 0.0017/ 0.0036 |
| 30 | 0.032/ 0.0012 |
| 31 | 0.0017/ 0.0012 |
| 32 | 0.0029/ 0.0012 |
| 33 | 2.0771/ 1.5112 |
| 34 | 0.0024/ 0.0229 |
| 35 | 0.0082/ 0.1109 |
| 36 | 0.0139/ 0.4883 |
| 37 | 0.0015/ 0.0053 |
| 38 | 0.0029/ 0.0191 |
| 39 | 0.003/ 0.0085 |

| Example | Ki (μM) mouse/rat |
|---|---|
| 40 | 0.0043/0.1204 |
| 41 | 0.0015/0.009 |
| 42 | 0.028/3.989 |
| 43 | 0.0164/0.3672 |
| 44 | 0.0044/0.0059 |
| 45 | 0.0023/0.0044 |
| 46 | 0.0016/0.0064 |
| 47 | 0.002/0.0012 |
| 48 | 0.0022/0.0018 |
| 49 | 0.0021/0.0015 |
| 50 | 0.0018/0.0014 |
| 51 | 0.0067/0.0126 |
| 52 | 0.0049/0.0058 |
| 53 | 0.0015/0.0017 |
| 54 | 0.003/0.0018 |
| 55 | 0.0012/0.0014 |
| 56 | 0.002/0.0035 |
| 57 | 0.0039/0.0127 |
| 58 | 0.0038/0.0161 |
| 59 | 0.0018/0.001 |
| 60 | 0.0008/0.001 |
| 61 | 0.0018/0.0025 |
| 62 | 0.0031/0.0028 |
| 63 | 0.0014/0.0007 |
| 64 | 0.0015/0.003 |
| 65 | 0.0037/0.0218 |
| 66 | 0.0033/0.0161 |
| 67 | 0.0016/0.0038 |
| 68 | 0.001/0.0081 |
| 69 | 0.0086/0.018 |
| 70 | 0.0056/0.0103 |
| 71 | 0.0018/0.0012 |
| 72 | 0.0019/0.001 |
| 73 | 0.0018/0.0019 |
| 74 | 0.0031/0.0039 |
| 75 | 0.0014/0.0011 |
| 76 | 0.0016/0.0018 |
| 77 | 0.001/0.0064 |
| 78 | 0.0012/0.0039 |
| 79 | 0.0022/0.1963 |
| 80 | 0.005/0.0325 |
| 81 | 0.0097/0.9593 |
| 82 | 0.0013/0.0016 |
| 83 | 0.006/0.0075 |
| 84 | 0.0036/0.0047 |
| 85 | 0.0033/0.0067 |
| 86 | 0.0023/0.0007 |
| 87 | 0.0105/0.0202 |
| 88 | 0.0034/0.0458 |
| 89 | 0.0024/0.0254 |
| 90 | 0.0006/0.0007 |
| 91 | 0.0053/0.003 |
| 92 | 0.0048/0.0045 |
| 93 | 0.0005/0.0012 |
| 94 | 0.0033/0.0381 |
| 95 | 0.0033/0.035 |
| 96 | 0.0013/0.0006 |
| 97 | 0.0824/0.184 |
| 98 | 0.0276/0.565 |
| 99 | 0.0063/0.1544 |
| 100 | 0.012/0.0202 |
| 101 | 0.017/0.524 |
| 102 | 0.0259/0.4099 |
| 103 | 0.0052/0.0031 |
| 104 | 0.0019/0.034 |
| 105 | 0.0032/0.0027 |
| 106 | 0.0063/0.0938 |
| 107 | 0.0093/0.0065 |
| 108 | 0.0054/0.0059 |
| 109 | 0.0026/0.0038 |
| 110 | 0.0088/0.0152 |
| 111 | 0.0074/0.0086 |
| 112 | 0.0259/0.0248 |
| 113 | 0.0481/0.0654 |
| 114 | 0.0649/0.2654 |
| 115 | 0.029/0.0343 |

-continued

| Example | Ki (μM) mouse/rat |
|---------|-------------------|
| 116 | 0.0512/0.1623 |
| 117 | 0.0284/0.045 |
| 118 | 0.0416/0.2636 |
| 119 | 0.0844/0.6868 |
| 120 | 0.0851/0.4256 |
| 121 | 0.0145/0.0158 |
| 122 | 0.1404/0.758 |
| 123 | 0.0413/0.0474 |
| 124 | 0.0235/0.0231 |
| 125 | 0.0182/0.0076 |
| 126 | 0.0202/0.0047 |
| 127 | 0.007/0.0016 |
| 128 | 0.0088/0.0025 |
| 129 | 0.0073/0.0025 |
| 130 | 0.0075/0.0038 |
| 131 | 0.0254/0.0144 |
| 132 | 0.008/0.0036 |
| 133 | 0.0095/0.018 |
| 134 | 0.0048/0.004 |
| 135 | 0.0105/0.5783 |
| 136 | 0.0075/0.0585 |
| 137 | 0.0067/0.0301 |
| 138 | 0.0042/0.3082 |

The compounds of formula I and the pharmaceutically acceptable salts of the compounds of formula I can be used as pharmaceuticals, e.g. in the form of pharmaceutical compositions. The pharmaceutical compositions can be administered orally, e.g. in the form of tablets, coated tablets, dragées, hard and soft gelatin capsules, solutions, emulsions or suspensions. The administration can, however, also be effected rectally, e.g. in the form of suppositories, or parenterally, e.g. in the form of injectable solutions.

The compounds of formula I can be processed with pharmaceutically inert, inorganic or organic carriers for the production of pharmaceutical compositions. Lactose, corn starch or derivatives thereof, talc, stearic acids or its salts and the like can be used, for example, as such carriers for tablets, coated tablets, dragées and hard gelatin capsules. Suitable carriers for soft gelatin capsules are, for example, vegetable oils, waxes, fats, semi-solid and liquid polyols and the like. Depending on the nature of the active substance no carriers are however usually required in the case of soft gelatin capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical compositions can, moreover, contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The invention also provides pharmaceutical compositions containing a compound of formula I or a pharmaceutically acceptable salt thereof and a therapeutically inert carrier and a process for their production, which comprises bringing one or more compounds of formula I and/or pharmaceutically acceptable acid addition salts and, if desired, one or more other therapeutically valuable substances into a galenical administration form together with one or more therapeutically inert carriers.

The most preferred indications in accordance with the present invention are those which include disorders of the central nervous system, for example the treatment or prevention of depression, psychosis, Parkinson's disease, anxiety, attention deficit hyperactivity disorder (ADHD) and diabetes.

The dosage at which compounds of the invention can be administered can vary within wide limits and will, of course, have to be adjusted to the individual requirements in each particular case. In the case of oral administration the dosage for adults can vary from about 0.01 mg to about 1000 mg per day of a compound of formula I or of the corresponding amount of a pharmaceutically acceptable salt thereof. The daily dosage can be administered as single dose or in divided doses and, in addition, the upper limit can also be exceeded when this is found to be indicated.

Tablet Formulation

Wet Granulation

| | | mg/tablet | | |
|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | |
|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

The invention claimed is:
1. The compound having formula ID

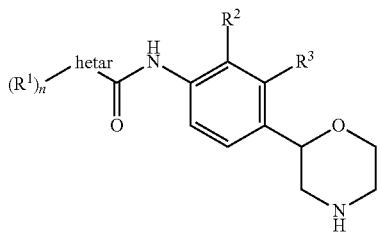

wherein
Hetar is selected from the group consisting of 1H-indazole-3-yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or a pharmaceutically suitable acid addition salt thereof;
$R^1$ is hydrogen,
halogen,
cyano,
lower alkyl,
lower alkyl substituted by halogen,
lower alkoxy,
lower alkoxy substituted by halogen or $C(O)NH_2$,
phenyl optionally substituted by halogen, cyano or lower alkoxy substituted by halogen, 2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl,
5-cyanopyrazin-2-yl, or
2-(trifluoromethyl)pyrimidin-4-yl;
n is 1 or 2;
$R^2$ is halogen or cyano and $R^3$ is hydrogen, or
$R^2$ is hydrogen and $R^3$ is halogen or cyano;
or a pharmaceutically suitable acid addition salt thereof.

2. The compound of claim 1, selected from the group consisting of
6-fluoro-1H-indazole-3-carboxylic acid ((R)-2-fluoro-4-morpholin-2-yl-phenyl)-amide;
6-fluoro-1H-indazole-3-carboxylic acid ((S)-2-fluoro-4-morpholin-2-yl-phenyl)-amide;
1-(4-fluoro-phenyl)-1H-pyrazole-3-carboxylic acid ((R)-2-fluoro-4-morpholin-2-yl-phenyl)-amide;
1-(4-fluoro-phenyl)-1H-pyrazole-3-carboxylic acid ((S)-2-fluoro-4-morpholin-2-yl-phenyl)-amide;
2-methyl-5-phenyl-2H-pyrazole-3-carboxylic acid ((S)-2-fluoro-4-morpholin-2-yl-phenyl)-amide;
(RS)—N-(2-chloro-4-(morpholin-2-yl)phenyl)-1-(4-fluorophenyl)-1H-pyrazole-4-carboxamide;
(R)—N-(2-fluoro-4-(morpholin-2-yl)phenyl)-1-(4-fluorophenyl)-1H-pyrazole-4-carboxamide;
(S)—N-(2-fluoro-4-(morpholin-2-yl)phenyl)-1-(4-fluorophenyl)-1H-pyrazole-4-carboxamide;
2-methyl-5-phenyl-2H-pyrazole-3-carboxylic acid ((R)-2-fluoro-4-morpholin-2-yl-phenyl)-amide; and
2-chloro-N—((R)-2-fluoro-4-morpholin-2-yl-phenyl)-6-methoxy-isonicotinamide.

3. The compound of claim 1, selected from the group consisting of
2-chloro-N—((S)-2-fluoro-4-morpholin-2-yl-phenyl)-6-methoxy-isonicotinamide;
(RS)—N-(2-cyano-4-(morpholin-2-yl)phenyl)-1-(4-fluorophenyl)-1H-pyrazole-3-carboxamide;
(S)—N-(2-chloro-4-(morpholin-2-yl)phenyl)-1-(4-fluorophenyl)-1H-pyrazole-3-carboxamide;
(R)—N-(2-chloro-4-(morpholin-2-yl)phenyl)-1-(4-fluorophenyl)-1H-pyrazole-3-carboxamide;
(S)—N-(2-chloro-4-(morpholin-2-yl)phenyl)-1-(4-fluorophenyl)-1H-pyrazole-4-carboxamide;
(R)—N-(2-chloro-4-(morpholin-2-yl)phenyl)-1-(4-fluorophenyl)-1H-pyrazole-4-carboxamide;
(R)-6-chloro-N-(2-chloro-4-(morpholin-2-yl)phenyl) nicotinamide;
(S)-6-chloro-N-(2-chloro-4-(morpholin-2-yl)phenyl) nicotinamide;
and
(S)-1-(3-(difluoromethoxy)phenyl)-N-(2-fluoro-4-(morpholin-2-yl)phenyl)-1H-pyrazole-4-carboxamide.

4. The compound of claim 1, selected from the group consisting of
(S)-1-(4-(difluoromethoxy)phenyl)-N-(2-fluoro-4-(morpholin-2-yl)phenyl)-1H-pyrazole-4-carboxamide;
(S)-4-cyano-N-(2-fluoro-4-(morpholin-2-yl)phenyl)picolinamide;
(R)-4-cyano-N-(2-fluoro-4-(morpholin-2-yl)phenyl)picolinamide;
(S)-6-cyano-N-(2-fluoro-4-(morpholin-2-yl)phenyl)picolinamide,
(S)-1-(2,2-difluorobenzo[d][1,3]dioxol-5-yl)-N-(2-fluoro-4-(morpholin-2-yl)phenyl)-1H-pyrazole-4-carboxamide;
(R)—N-(3-fluoro-4-(morpholin-2-yl)phenyl)-2-(trifluoromethyl)isonicotinamide;
(R)-2-ethoxy-N-(3-fluoro-4-(morpholin-2-yl)phenyl) isonicotinamide;
(R)-6-ethoxy-N-(3-fluoro-4-(morpholin-2-yl)phenyl) nicotinamide;
(R)-1-(4-(difluoromethoxy)phenyl)-N-(3-fluoro-4-(morpholin-2-yl)phenyl)-1H-pyrazole-4-carboxamide; and
(S)—N-(3-fluoro-4-(morpholin-2-yl)phenyl)-2-(trifluoromethyl)isonicotinamide.

5. The compound of claim 1, selected from the group consisting of
(S)-2-ethoxy-N-(3-fluoro-4-(morpholin-2-yl)phenyl) isonicotinamide;
(S)-6-ethoxy-N-(3-fluoro-4-(morpholin-2-yl)phenyl) nicotinamide;
(S)-1-(4-(difluoromethoxy)phenyl)-N-(3-fluoro-4-(morpholin-2-yl)phenyl)-1H-pyrazole-4-carboxamide;
(R)—N-(3-chloro-4-(morpholin-2-yl)phenyl)-2-ethoxyisonicotinamide;
(R)—N-(3-chloro-4-(morpholin-2-yl)phenyl)-6-ethoxynicotinamide;
(R)—N-(3-chloro-4-(morpholin-2-yl)phenyl)-1-(4-(difluoromethoxy)phenyl)-1H-pyrazole-4-carboxamide;
(S)—N-(3-chloro-4-(morpholin-2-yl)phenyl)-2-ethoxyisonicotinamide;
(S)—N-(3-chloro-4-(morpholin-2-yl)phenyl)-6-ethoxynicotinamide;
(S)—N-(3-chloro-4-(morpholin-2-yl)phenyl)-1-(4-(difluoromethoxy)phenyl)-1H-pyrazole-4-carboxamide;
and
(R)—N-(2-chloro-4-(morpholin-2-yl)phenyl)-6-cyanopicolinamide.

6. The compound of claim 1, selected from the group consisting of
- (S)—N-(2-chloro-4-(morpholin-2-yl)phenyl)-6-cyanopicolinamide,
- (S)—N-(2-chloro-4-(morpholin-2-yl)phenyl)-5-cyanopicolinamide;
- (R)—N-(2-chloro-4-(morpholin-2-yl)phenyl)-5-cyanopicolinamide;
- (S)—N-(2-chloro-4-(morpholin-2-yl)phenyl)-6-cyanonicotinamide
- (R)—N-(2-chloro-4-(morpholin-2-yl)phenyl)-6-cyanonicotinamide;
- (S)—N-(2-chloro-4-(morpholin-2-yl)phenyl)-1-(4-cyanophenyl)-1H-pyrazole-4-carboxamide;
- (S)-1-(4-(difluoromethoxy)phenyl)-N-(2-fluoro-4-(morpholin-2-yl)phenyl)-1H-1,2,3-triazole-4-carboxamide;
- (S)—N-(3-chloro-4-(morpholin-2-yl)phenyl)-1-(4-cyanophenyl)-1H-pyrazole-4-carboxamide;
- (S)-4-chloro-6-cyano-N-(2-fluoro-4-(morpholin-2-yl)phenyl)picolinamide; and
- (S)-2-cyano-N-(3-fluoro-4-(morpholin-2-yl)phenyl)-6-methoxyisonicotinamide.

7. The compound of claim 1, selected from the group consisting of
- (S)-1-(4-cyano-2-fluorophenyl)-N-(3-fluoro-4-(morpholin-2-yl)phenyl)-1H-pyrazole-4-carboxamide;
- (S)—N-(3-chloro-4-(morpholin-2-yl)phenyl)-1-(4-cyano-2-fluorophenyl)-1H-pyrazole-4-carboxamide;
- (S)-1-(4-cyano-2-fluorophenyl)-N-(2-fluoro-4-(morpholin-2-yl)phenyl)-1H-pyrazole-4-carboxamide;
- (S)-1-(4-cyanophenyl)-N-(2-fluoro-4-(morpholin-2-yl)phenyl)-1H-pyrazole-4-carboxamide;
- (S)—N-(3-chloro-4-(morpholin-2-yl)phenyl)-2-cyano-6-methylisonicotinamide;
- (S)-2-cyano-N-(2-fluoro-4-(morpholin-2-yl)phenyl)-6-methylisonicotinamide;
- (S)—N4-(3-fluoro-4-(morpholin-2-yl)phenyl)-6-methylpyridine-2,4-dicarboxamide;
- (S)-2-cyano-N-(3-fluoro-4-(morpholin-2-yl)phenyl)-6-methylisonicotinamide;
- (S)-6-chloro-N4-(3-fluoro-4-(morpholin-2-yl)phenyl)pyridine-2,4-dicarboxamide; and
- (S)-6-ethyl-N4-(3-fluoro-4-(morpholin-2-yl)phenyl)pyridine-2,4-dicarboxamide.

8. The compound of claim of 1, selected from the group consisting of
- (S)—N4-(3-chloro-4-(morpholin-2-yl)phenyl)-6-methylpyridine-2,4-dicarboxamide;
- (S)—N4-(2-fluoro-4-(morpholin-2-yl)phenyl)-6-methylpyridine-2,4-dicarboxamide;
- (S)—N4-(2-fluoro-4-(morpholin-2-yl)phenyl)-6-methoxypyridine-2,4-dicarboxamide;
- (S)-2-cyano-N-(2-fluoro-4-(morpholin-2-yl)phenyl)-6-methoxyisonicotinamide;
- (S)—N4-(2-chloro-4-(morpholin-2-yl)phenyl)-6-methylpyridine-2,4-dicarboxamide;
- (S)—N-(2-chloro-4-(morpholin-2-yl)phenyl)-2-cyano-6-methylisonicotinamide;
- (S)—N-(2-chloro-4-(morpholin-2-yl)phenyl)-2-cyano-6-methoxyisonicotinamide;
- (S)—N-(2-fluoro-4-(morpholin-2-yl)phenyl)-1-(6-(trifluoromethyl)pyrazin-2-yl)-1H-pyrrazole-4-carboxamide;
- (S)—N-(2-chloro-4-(morpholin-2-yl)phenyl)-1-(6-(trifluoromethyl)pyrazin-2-yl)-1H-pyrazole-4-carboxamide; and
- (S)—N-(3-fluoro-4-(morpholin-2-yl)phenyl)-1-(6-(trifluoromethyl)pyrazin-2-yl)-1H-pyrazole-4-carboxamide.

9. The compound of claim 1, selected from the group consisting of
- (S)—N-(3-chloro-4-(morpholin-2-yl)phenyl)-1-(6-(trifluoromethyl)pyrazin-2-yl)-1H-pyrazole-4-carboxamide;
- (S)—N-(3-fluoro-4-(morpholin-2-yl)phenyl)-1-(6-(trifluoromethyl)pyrimidin-4-yl)-1H-pyrazole-4-carboxamide;
- (S)—N-(3-fluoro-4-(morpholin-2-yl)phenyl)-1-(6-(trifluoromethyl)pyridin-3-yl)-1H-pyrazole-4-carboxamide;
- (S)-1-(5-cyanopyrazin-2-yl)-N-(3-fluoro-4-(morpholin-2-yl)phenyl)-1H-pyrazole-4-carboxamide;
- (S)—N-(3-fluoro-4-(morpholin-2-yl)phenyl)-1-(2-(trifluoromethyl)pyrimidin-4-yl)-1H-pyrazole-4-carboxamide;
- (S)-4-chloro-6-cyano-N-(3-fluoro-4-(morpholin-2-yl)phenyl)picolinamide;
- (S)—N-(3-fluoro-4-(morpholin-2-yl)phenyl)-1-(5-(trifluoromethyl)pyrazin-2-yl)-1H-pyrazole-4-carboxamide;
- (S)-5-cyano-N-(2-fluoro-4-(morpholin-2-yl)phenyl)-6-methylpicolinamide;
- (S)-5-cyano-N-(3-fluoro-4-(morpholin-2-yl)phenyl)-6-methylpicolinamide;
- (S)—N-(3-fluoro-4-(morpholin-2-yl)phenyl)-5-(trifluoromethyl)pyrazine-2-carboxamide and
- (S)-6-ethoxy-N-(2-fluoro-4-(morpholin-2-yl)phenyl) nicotinamide.

10. The compound of claim 1 in which Hetar is pyridine-4-yl.

11. The compound of claim 10 which is S—N-(3-fluoro-4-(morpholin-2-yl)-phenyl)-2-trifluoromethyl) isonicotinamide.

12. A pharmaceutical composition comprising a therapeutically effective amount of a compound of formula ID

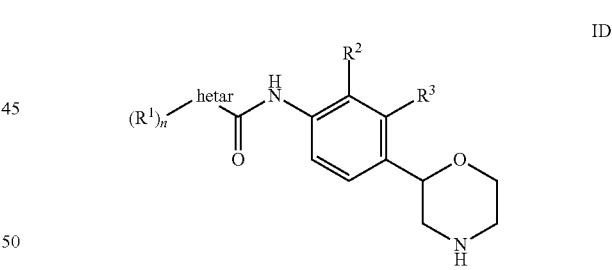

wherein
Hetar is selected from the group consisting of 1H-indazole-3yl, pyridine-2-yl, pyridine-3-yl, pyridine-4-yl, pyrimidine-5-yl, 1H-pyrazole-3-yl, 1H-pyrazole-4-yl and 1H-pyrazole-5-yl;
or a pharmaceutically suitable acid addition salt thereof;
$R^1$ is hydrogen,
halogen,
cyano,
lower alkyl,
lower alkyl substituted by halogen,
lower alkoxy,
lower alkoxy substituted by halogen or $C(O)NH_2$,
phenyl optionally substituted by halogen, cyano or lower alkoxy substituted by halogen, 2,2-difluorobenzo[d][1,3]dioxol-5-yl,
6-(trifluoromethyl)pyrazin-2-yl,
5-(trifluoromethyl)pyrazin-2-yl,
6-(trifluoromethyl)pyrimidin-4-yl,
6-(trifluoromethyl)pyridin-3-yl,
5-cyanopyrazin-2-yl, or
2-(trifluoromethyl)pyrimidin-4-yl;

n is 1 or 2;

$R^2$ is halogen or cyano and $R^3$ is hydrogen, or $R^2$ is hydrogen and $R^3$ is halogen or cyano;

Or a pharmaceutically suitable acid addition salt thereof.

13. The composition of claim 12 in which Hetar is pyridine-4-yl.

* * * * *